(12) United States Patent
Forsell

(10) Patent No.: US 11,234,713 B2
(45) Date of Patent: Feb. 1, 2022

(54) HIP JOINT INSTRUMENT AND METHOD

(71) Applicant: Peter Forsell, Bouveret (CH)

(72) Inventor: Peter Forsell, Bouveret (CH)

( * ) Notice: Subject to any disclaimer, the term of this patent is extended or adjusted under 35 U.S.C. 154(b) by 379 days.

(21) Appl. No.: 16/297,818

(22) Filed: Mar. 11, 2019

(65) Prior Publication Data

US 2019/0269419 A1 Sep. 5, 2019

Related U.S. Application Data

(63) Continuation of application No. 15/005,060, filed on Jan. 25, 2016, now Pat. No. 10,226,259.

(51) Int. Cl.
| | | |
|---|---|---|
| *A61F 2/32* | (2006.01) | |
| *A61F 2/36* | (2006.01) | |
| *A61B 17/16* | (2006.01) | |
| *A61F 2/34* | (2006.01) | |
| *A61F 2/30* | (2006.01) | |

(52) U.S. Cl.
CPC .......... *A61B 17/1615* (2013.01); *A61B 17/16* (2013.01); *A61B 17/1617* (2013.01); *A61B 17/1622* (2013.01); *A61B 17/1624* (2013.01); *A61B 17/1662* (2013.01); *A61B 17/1666* (2013.01); *A61B 17/1668* (2013.01); *A61F 2/34* (2013.01); *A61F 2/3601* (2013.01); *A61F 2/3603* (2013.01); *A61F 2002/305* (2013.01); *A61F 2002/30469* (2013.01); *A61F 2002/30471* (2013.01); *A61F 2002/30495* (2013.01); *A61F 2002/30594* (2013.01); *A61F 2002/30616* (2013.01); *A61F 2002/30818* (2013.01); *A61F 2220/0025* (2013.01)

(58) Field of Classification Search
CPC ...... A61F 2/32; A61F 2/34; A61F 2/36; A61F 2/3609; A61F 2/3621; A61F 2002/3208; A61F 2002/3216; A61F 2002/3225; A61F 2002/3233; A61F 2002/3241; A61F 2002/3401; A61F 2002/3403; A61F 2002/3404; A61F 2002/3406; A61F 2002/3408; A61F 2002/3409; A61F 2002/3411; A61F 2002/3412; A61F 2002/3432
USPC ........... 623/22.11–22.15; 606/86 R; 604/264
See application file for complete search history.

(56) References Cited

U.S. PATENT DOCUMENTS

| | | | | |
|---|---|---|---|---|
| 4,731,088 A | * | 3/1988 | Collier | ................ A61F 2/30742 623/22.13 |
| 6,991,656 B2 | * | 1/2006 | Mears | .............. A61B 17/00234 623/22.4 |

(Continued)

*Primary Examiner* — Jessica Weiss

(57) ABSTRACT

A method of treating a hip joint of a human patient using a pelvic drill comprising a driving member, a bone contacting and an operating device for operating said driving member. The method comprise the steps of cutting the skin of the human patient, dissecting an area of the pelvic bone on the opposite side from the acetabulum, creating a hole in said dissected area using said pelvic drill, said hole passing through the pelvic bone and into the hip joint of the human patient, and providing at least one hip joint surface to the hip joint, through said hole in the pelvic bone of the human patient. In one embodiment the method includes inserting a needle or tube like instrument into the patient's body for filling a part of the patient's body with gas and thereby expanding a cavity within the body.

13 Claims, 38 Drawing Sheets

(56) References Cited

U.S. PATENT DOCUMENTS

| | | | | |
|---|---|---|---|---|
| 2003/0050704 A1* | 3/2003 | Keynan | ................. | A61B 17/72 623/22.12 |
| 2007/0173946 A1* | 7/2007 | Bonutti | ................ | A61B 17/025 623/20.14 |
| 2009/0005871 A1* | 1/2009 | White | ................. | A61B 17/562 623/17.11 |

* cited by examiner

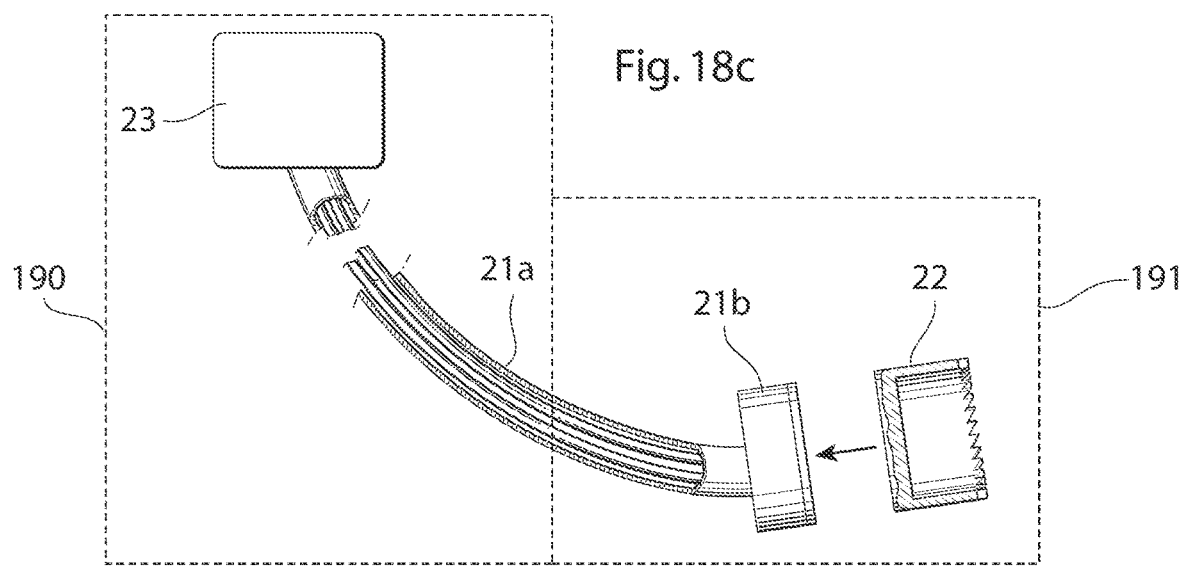
Fig. 18c
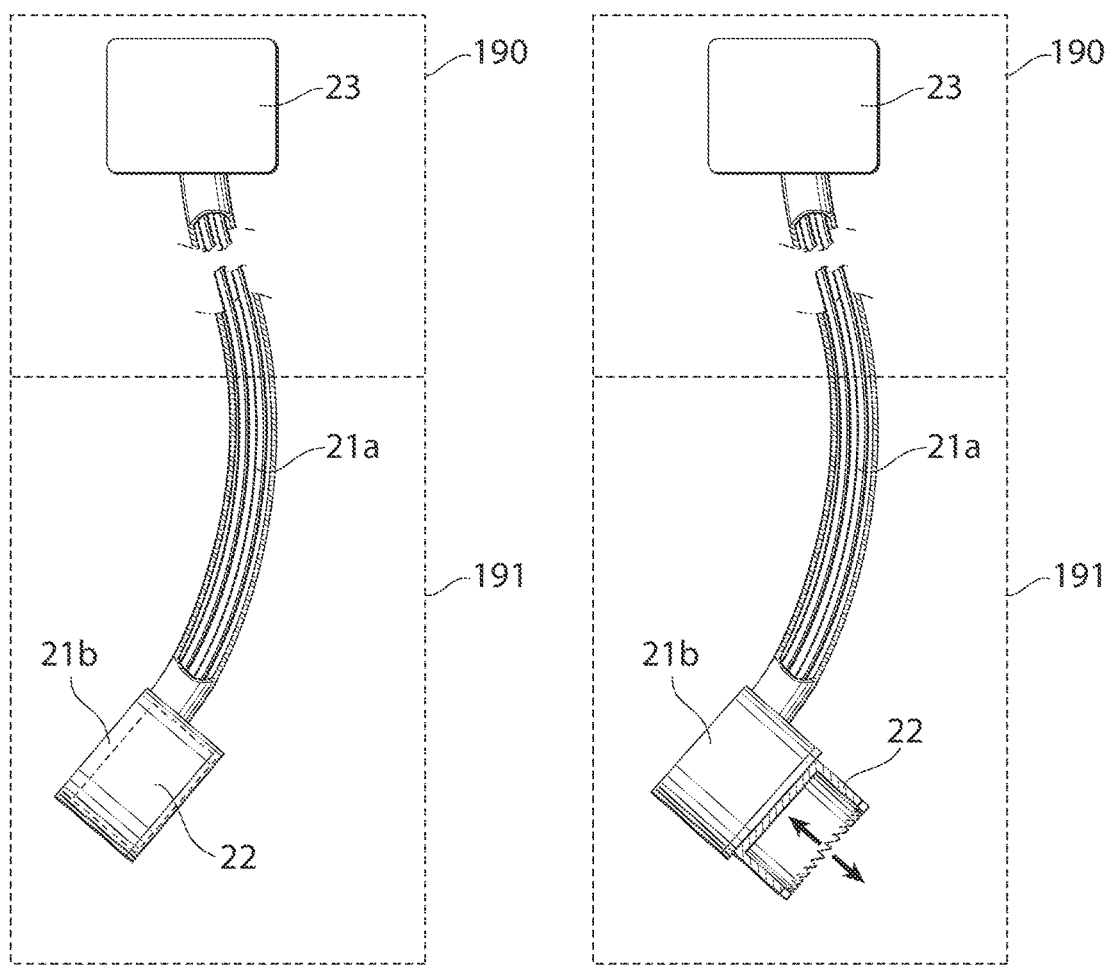
Fig. 18d
Fig. 18e

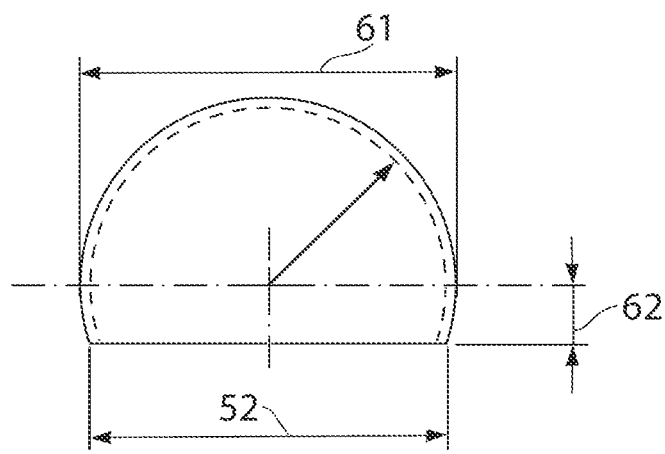
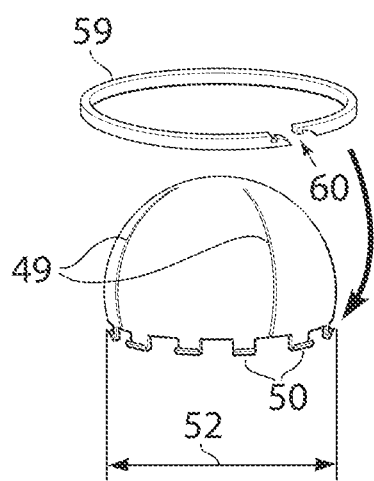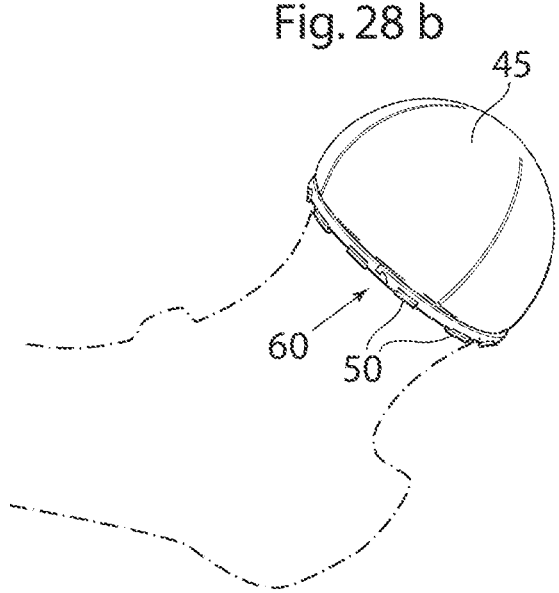

Fig. 31 a  Fig. 31 b  Fig. 31 c
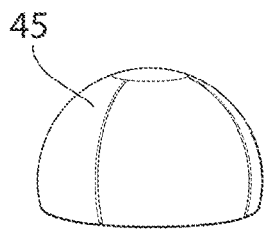 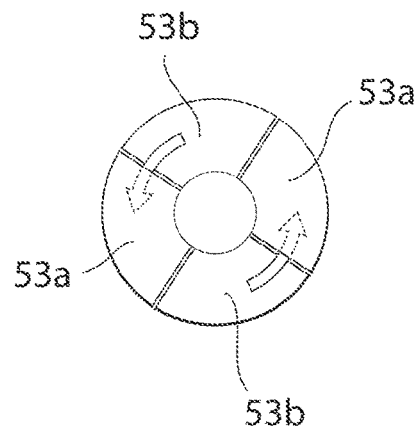 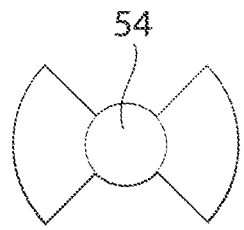
Fig. 31 d  Fig. 31 e
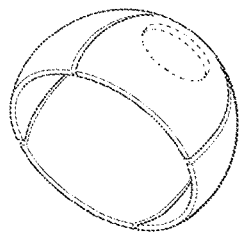 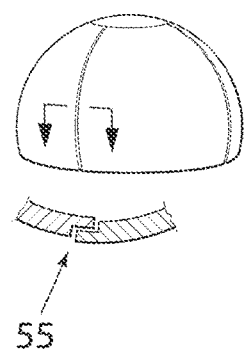
Fig. 32 a  Fig. 32 b
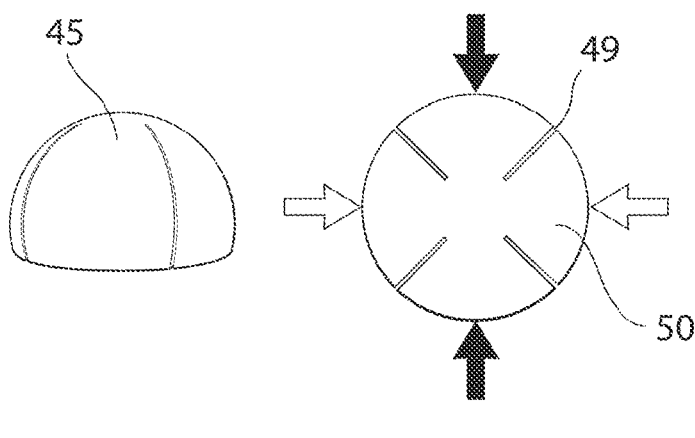 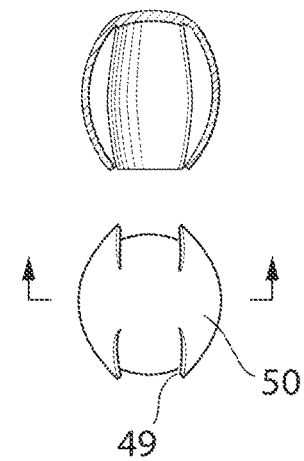

Fig. 33 a
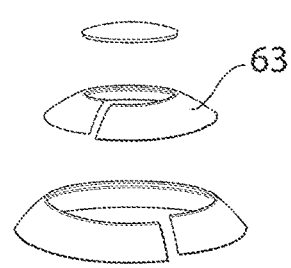
Fig. 33 b
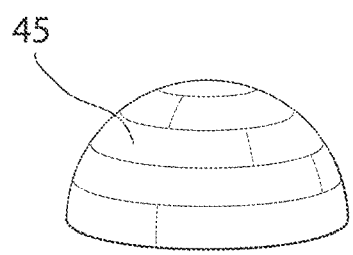
Fig. 33 c
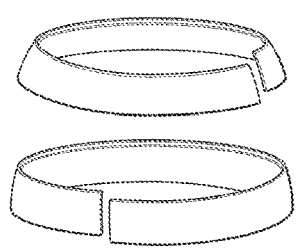
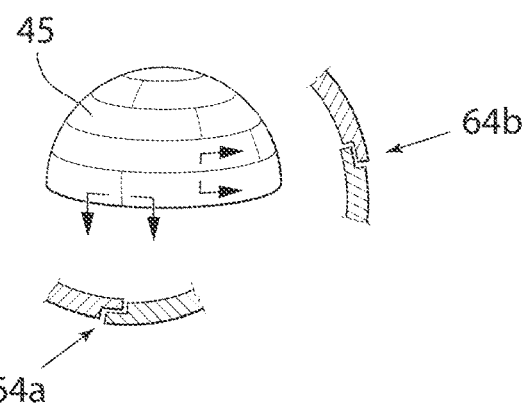
Fig. 34 a
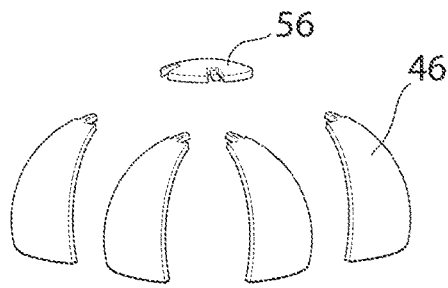
Fig. 34 b
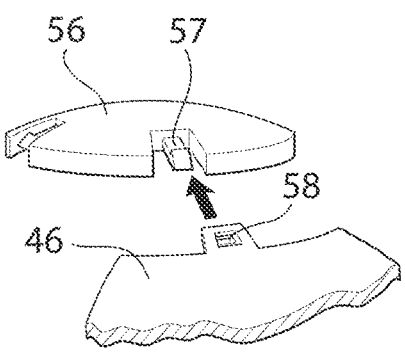
Fig. 34 c
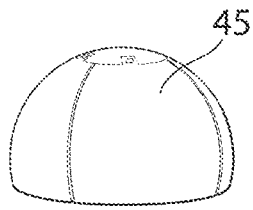

Fig. 44
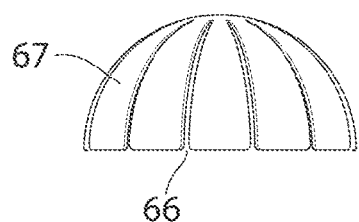
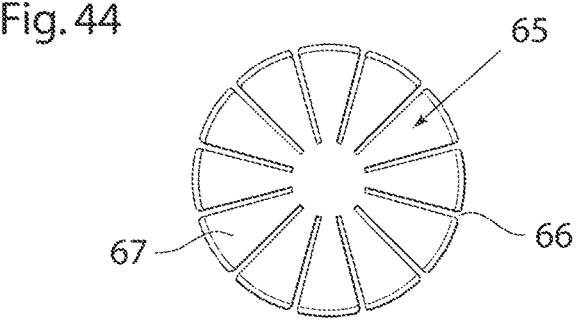
Fig. 45 a
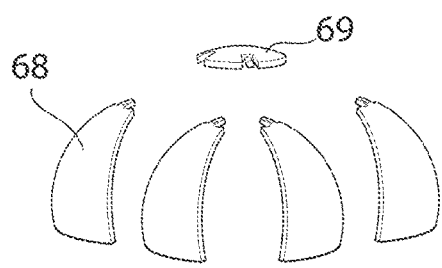
Fig. 45 b
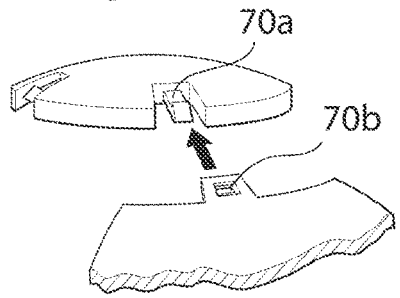
Fig. 45 c
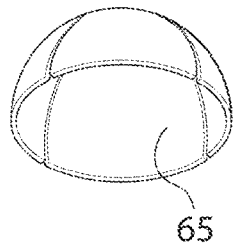
Fig. 46 a
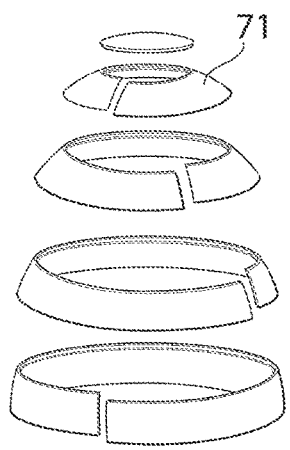
Fig. 46 b
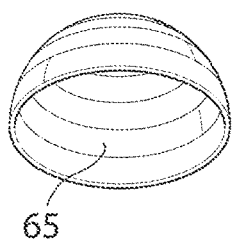
Fig. 46 c
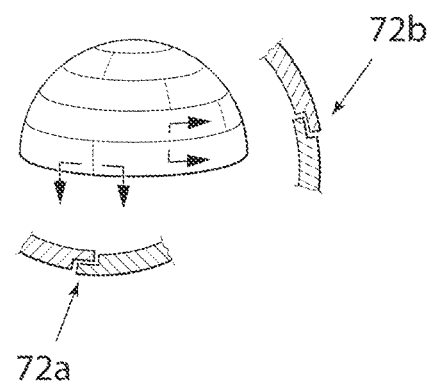

Fig. 47 a
Fig. 47 b
Fig. 47 c
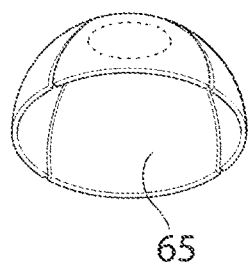
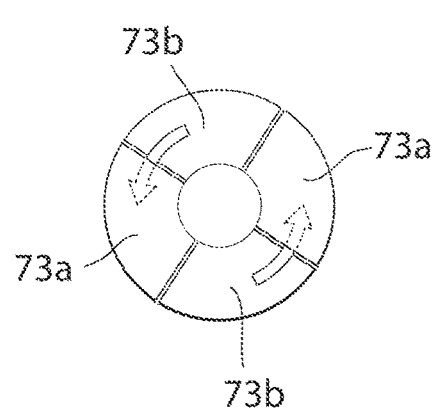
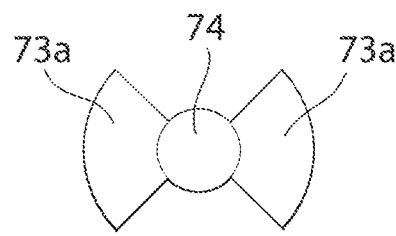
Fig. 47 d
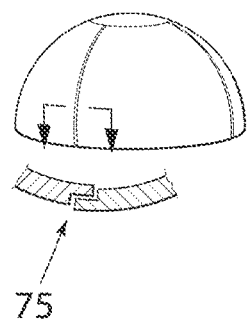
Fig. 48 a
Fig. 48 b
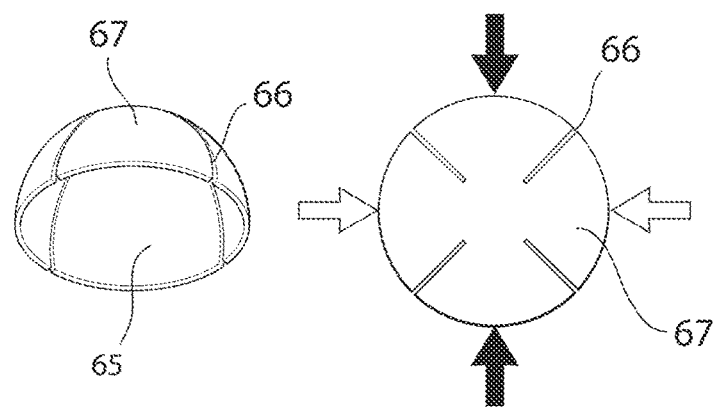
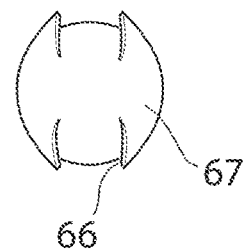

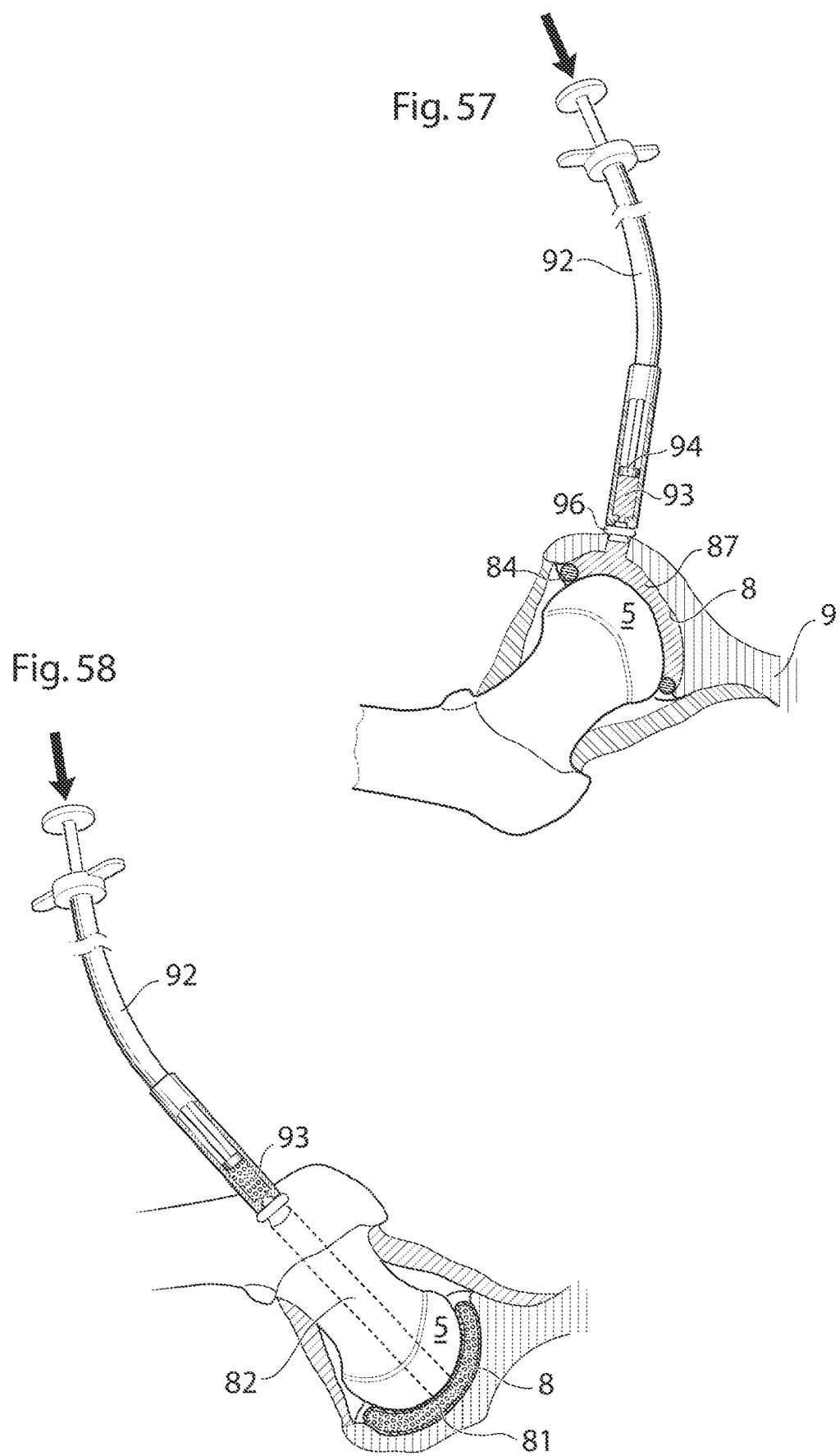

HIP JOINT INSTRUMENT AND METHOD

This application is a continuation of U.S. patent application Ser. No. 15/005,060 filed 25 Jan. 2016, which is a continuation of U.S. patent application Ser. No. 13/383,289 filed 10 Jan. 2012 which is the U.S. national phase of International Application No. PCT/SE2010/050824, filed 12 Jul. 2010, which designated the U.S. and claims the benefit of U.S. Provisional No. 61/229,755, filed 30 Jul. 2009; 61/229,738 filed 30 Jul. 2009; 61/229,739 filed 30 Jul. 2009; 61/229,743 filed 30 Jul. 2009; 61/229,745 filed 30 Jul. 2009; 61/229,746 filed 30 Jul. 2009; 61/229,747 filed 30 Jul. 2009; 61/229,748 filed 30 Jul. 2009; 61/229,751 filed 30 Jul. 2009; 61/229,752 filed 30 Jul. 2009; 61/229,761 filed 30 Jul. 2009; 61/229,767 filed 30 Jul. 2009; 61/229,778 filed 30 Jul. 2009; 61/229,786 filed 30 Jul. 2009; 61/229,789 filed 30 Jul. 2009; 61/229,796 filed 30 Jul. 2009; 61/229,735 filed 30 Jul. 2009; and which claims priority to Swedish Application Nos.: 0900981-2 filed 10 Jul. 2009; 0900957-2 filed 10 Jul. 2009; 0900958-0 filed 10 Jul. 2009; 0900959-8 filed 10 Jul. 2009; 0900960-6 filed 10 Jul. 2009; 0900962-2 filed 10 Jul. 2009; 0900963-0 filed 10 Jul. 2009; 0900965-5 filed 10 Jul. 2009; 0900966-3 filed 10 Jul. 2009; 0900968-9 filed 10 Jul. 2009; 0900969-7 filed 10 Jul. 2009; 0900970-5 filed 10 Jul. 2009; 0900972-1 filed 10 Jul. 2009; 0900973-9 filed 10 Jul. 2009; 0900974-7 filed 10 Jul. 2009; 0900976-2 filed 10 Jul. 2009 and 0900978-8 filed 10 Jul. 2009, the entire contents of each of which are hereby incorporated by reference.

FIELD OF INVENTION

The present invention relates generally to a surgical instrument for use in a surgical or laparoscopic/arthroscopic method of treating hip osteoarthritis in a human patient.

BACKGROUND

Hip joint Osteoarthritis is a syndrome in which low-grade inflammation results in pain in the hip joints, caused by abnormal wearing of the Cartilage that acts as a cushion inside of the hip joint. This abnormal wearing of the cartilage also results in a decrease of the joints lubricating fluid called Synovial fluid. Hip joint Osteoarthritis is estimated to affect 80% of all people above 65 years of age, in more or less serious forms.

The present treatment for hip osteoarthritis comprises NSAID drugs, local injections of Hyaluronic acid or Glucocorticoid to help lubricating the hip joint, and replacing parts of the hip joint with a prosthesis through hip joint surgery.

The replacing of parts of the hip joint is one of the most common surgeries to date performed on hundreds of thousands of patients in the world annually. The most common method comprises placing a metal prosthesis in Femur and a plastic bowl in Acetabulum. This operation is done through a lateral incision in the hip and upper thigh and through, Fascia Lata and the lateral muscles of the thigh. To get access to the joint, the supporting Fibrous Capsule attached to Femur and Ilium needs to be penetrated, making it difficult to get a fully functional joint after the surgery. Femur is then cut at the neck with a bone saw and the prosthesis is placed in femur either with bone cement or without bone cement. Acetabulum is slightly enlarged using an Acetabular reamer, and the plastic bowl is positioned using screws or bone cement.

The surgery typically requires one week of hospitalization due to the increased risk of infection. The recovery process is on average about 6 weeks, but even after this period the patient should not perform any physical activates that places large strain on the joint.

It would therefore be desirable to have a surgical instrument that would make it possible to spare the Fibrous Capsule and reduce the removal of healthy Femur bone. It would further be preferable to have a method of operating that could shorten the time for recovery of the patient, and reducing the amount of affected large blood vessels, thus reducing the risk of blood clots.

SUMMARY

A pelvic drill for creating a through-going hole in the pelvic bone of a human patient is provided. The pelvic drill comprises an internal portion adapted to be placed inside the body of a patient, when in use, and an external portion adapted to be kept outside of the body of the patient when in use. The pelvic drill further comprises: a driving member, a bone contacting organ in connection with the driving member being a part of the internal portion and being adapted for bone and/or cartilage drilling in the pelvic bone, an operating device adapted to operate said driving member, wherein said bone contacting organ is adapted to create the hole in the acetabulum area, starting from the abdominal side of the pelvic bone of the human patient. By the creation of a hole in the pelvic bone, the hip joint can be accessed from the abdominal side of the pelvic bone, without injuring the hip joint capsule.

In one embodiment, the pelvic drill is adapted to be operated by the operating device from the abdominal side of the pelvic bone of the human patient. The operating device could be a part of the external portion or a part of the internal portion.

According to one embodiment the driving member is adapted to be operated on the abdominal side of the pelvic bone.

According to one embodiment, the pelvic drill could comprise at least one bend such that the internal portion of the pelvic drill can be introduced through the skin of the patient and moved down the pelvic bone to a position on the opposite side of the acetabulum for creating a hole in the pelvic bone from the abdominal side thereof and further into the hip joint.

The bend in any of the embodiment could have an angle in the interval 10-20 degrees or 20-30 degrees or 30-40 degrees or 40-50 degrees or 50-60 degrees.

According to one embodiment, the external portion of the pelvic drill could further comprise a handle, and the length of the pelvic drill is adapted to reach from the handle and to the area of the pelvic bone opposite to the acetabulum for creating a hole in the pelvic bone.

According to another embodiment of the pelvic drill, the distance between the end of the handle and the bend is in the interval 10-20 cm or in the interval 20-30 cm or in the interval 30-40 cm or in the interval 40-50 cm.

According to yet another embodiment, the distance between the bend and the bone contacting organ is in the interval 2-4 cm or in the interval 4-6 cm or in the interval 6-8 cm or in the interval 10-12 cm or in the interval 12-14 cm.

According to yet another embodiment, the internal portion comprises a plurality of connectable parts adapted to be connected after insertion into the patient for forming the internal portion of the medical device.

According to one embodiment, the internal portion comprises a first part comprising the bone contacting organ, and a second part comprising the driving member, and wherein the first and second parts are adapted to be connected after insertion into the body of the patient for at least partially forming the internal portion of the pelvic drill.

A further object is to provide a surgical instrument for operating hip osteoarthritis. The surgical instrument is adapted to create a hole in the pelvic bone of a human patient placed in the acetabulum area from the abdominal side of the pelvic bone. Said hole enables the surgeon to reach the hip joint from the abdominal, inguinal or pelvic areas.

According to one embodiment the surgical instrument comprises a driving member, a bone contacting organ in connection with said driving member and operating device adapted to operate said driving member. According to this embodiment the bone contacting organ is adapted to create said hole in the acetabulum area starting from the abdominal side of the pelvic bone of the human patient through repetitive or continuous movement.

According to one embodiment, an opposite-acetabulum instrument, i.e. an instrument adapted to operate on the pelvic bone on the opposite side from acetabulum is provided.

According to the second embodiment, the instrument comprises, a driving member, a bone contacting organ in connection with said driving member and an operating device adapted to operate said driving member. The bone contacting organ is adapted to create a hole in bone and to create the hole in the acetabulum area of the human patient through repetitive or continuous movement. The instrument is furthermore adapted to be operated starting from the abdominal side of the pelvic bone of the human patient.

According to one embodiment the surgical instrument is adapted to be operated by said operating device from the abdominal side of the pelvic bone of the human patient, or operated by said operating device from the hip side of the pelvic bone of the human patient.

According to another embodiment the surgical instrument is adapted to be operated with the bone contacting organ starting to create said hole from the abdominal side of the pelvic bone of the human patient, which could be performed by operating said operating device from the outside of the human body. The operating device could also be operated from the outside of the human body from the same side of said human body as the acetabulum of the pelvic bone or from the outside of the human body from the opposite side of said human body as the acetabulum of the pelvic bone.

According to yet another embodiment the driving member is adapted to follow a hole in the pelvic bone from the opposite side of the acetabulum, to the abdominal side of the pelvic bone, further penetrating the femoral bone, lateral out from the femoral bone and further out from the human body, all on the same side of the human body. The driving member is further adapted to be operated by said operating device from outside of said human body, in the position lateral of the femoral bone.

According to yet another embodiment the driving member is adapted to go from a starting point in the pelvic bone on the opposite side of the acetabulum, further back contra-lateral and proximal on the abdominal side of the pelvic bone, further penetrating the pelvic bone or the abdominal wall on the opposite side of the human body, lateral out on the opposite side of the human body, compared to the starting point. The driving member is adapted to be operated by said operating device from outside of said human body, in the position contra-lateral and proximal of the starting point in the human body.

At least a part of the driving member could be adapted to be operated from the abdominal side of the pelvic bone.

The surgical instrument according to any of the embodiments could be adapted to be curved in such a way that it is adapted to be introduced through the skin and further down the pelvic bone on the opposite side of the acetabulum for creating the hole in the pelvic bone from the abdominal side thereof and further into the hip joint.

According to one embodiment the surgical instrument could be adapted to be a special laparoscopic/arthroscopic instrument introduced into the abdomen and further down to the pelvic bone on the opposite side of the acetabulum and adapted to create the hole. The instrument could further comprises a handle, placed outside the abdominal wall when in use. The length of the instrument could be adapted to reach from the handle and into the hip joint via the, by said instrument, surgically created hole in the pelvic bone. The longitudinal extension of the instrument could comprise at least one bend, for the instrument to reach, when used as a special laparoscopic/arthroscopic instrument, to create the hole into the hip joint, thus said instrument being adapted to reach from the handle end into the abdomen and further down to the pelvic bone on the opposite side of the acetabulum, and after creating said hole, further into the hip joint through the hole reaching the hip joint end of said instrument.

According to yet another embodiment the surgical instrument could be adapted to be a special pelvic instrument introduced into the pelvic region and further to the pelvic bone on the opposite side of the acetabulum and adapted to create the hole in the pelvic bone. The instrument could further comprising a handle, placed outside the skin above the pelvic region when in use, wherein the length of the instrument could be adapted to reach from the handle and into the hip joint and wherein the longitudinal extension of said instrument is comprising at least one bend, for the instrument to reach, when used as special pelvic instrument to create said hole into the hip joint, from the handle into the pelvic region and further down to the pelvic bone on the opposite side of the acetabulum and after creating said hole, further into the hip joint through the hole reaching the hip joint end of said instrument.

According to yet another embodiment the surgical instrument could be adapted to be a special retroperitoneal instrument introduced into the body just above the inguinal region following the pelvic bone down to the opposite side of the acetabulum and adapted to create said hole in the pelvic bone. The instrument could further comprise a handle, placed outside the skin above the pelvic region when in use. The length of the instrument could be adapted to reach from the handle and into the hip joint and the longitudinal extension of the instrument could comprise at least one bend, for the instrument to reach, when used as special retroperitoneal instrument to create the hole into the hip joint, from the handle end following the pelvic bone and further down to the pelvic bone on the opposite side of the acetabulum and introduced into the hip joint through the hole reaching the hip joint end of said instrument.

According to one embodiment of the surgical instrument, the distance between the end of said handle or operating device and said bend is at least 10 cm. According to yet another embodiment of the surgical instrument, the distance between the end of said handle and said bend is at least 20 cm. According to one embodiment of the surgical instrument, the distance between the end of said handle and said bend is at least 30 cm. According to one embodiment of the surgical instrument, the distance between the end of said handle and said bend is at least 40 cm. According to one embodiment of the surgical instrument, the distance between the end of said handle and said bend is at least 50 cm.

The surgical instrument according to any one of the embodiments herein, could be adapted to have a bend with an angle of at least 10 degrees, or a bend is bent with an angle of at least 20 degrees or a bend with an angle of at least 30 degrees, or a bend with an angle of at least 40 degrees, or a bend with an angle of at least 50 degrees, or a bend with an angle of at least 60 degrees.

The surgical instrument according to any one of the embodiments herein, could be adapted to have a distance between said bend and the hip joint end or gripping end of said instrument being at least 2 cm, or being at least 4 cm, or being at least 6 cm, or being at least 8 cm, or being at least 10 cm, or being at least 12 cm, or being at least 14 cm.

Comprising an Angle

The instrument according to the first or second embodiment can further be adapted to be bent by means of a fixed angle, an adjustable angle, a parallel displaced part or section, at least one gear wheel or at least one universal joint.

In the embodiment where the surgical instrument is further adapted to be bent by means of an adjustable angle it is conceivable that said adjustable angle comprises an angle adjusting member adapted to adjust the angle of said bone contacting organ in relation to the pelvic bone of the human patient.

The Driving Member

The driving member in any of the embodiment above could be adapted to comprise at least one of: at least one worm gear, at least one chain, at least one driving belt, at least one universal joint, and at least one gear wheel.

The Operating Device

The operating device according to any of the embodiments above could be adapted to be electrically operated, in which case the operating device could comprise at least one electrical motor, or hydraulically operated, in which case the operating device could comprise at least one hydraulic motor. It is also conceivable that said operating device is battery powered, in which case a battery could be integrated in the instrument.

Additional Parts

Furthermore the instrument according to any of the embodiment above could comprise at least one of: a handle portion, a device for measurement of the depth of said hole, at least one camera, at least one light source, a device for measurement of torque or a stabilizing drill.

The construction of the instrument according to any of the embodiments above could be such that the instrument is adapted to make a bone plug, in which case the instrument could further comprise a gripping device for gripping said bone plug.

According to another embodiment the instrument according to any of the embodiments above is adapted to make small pieces of bone when creating said hole, in which case the instrument would further comprise a device for transport of said small pieces of bone.

According to yet another embodiment the instrument according to any of the embodiments above is further adapted to drill in cartilage. It is also conceivable that said bone contacting organ can be replaced by a reaming organ adapted to ream the acetabulum or the caput femur, in which case the reaming organ could be expandable and adapted for insertion through a hole smaller than the area possible to ream using said expandable reamer.

The Surgical and Laparoscopic/Arthroscopic Method

A second object is to provide a surgical and a laparoscopic/arthroscopic method for treating a hip joint of a human patient using the instrument according to any of the embodiments. The hip joint comprises a caput femur located on the very top of the femur bone and an acetabulum, which is a part of the pelvic bone, the caput femur is in connection with the acetabulum.

The idea is to perform an operation in the hip joint through a hole in the pelvic bone, however some of the aspects can be performed using conventional surgery entering the hip joint through the hip joint capsule, or by entering through the femur bone.

The surgical method comprises the steps of cutting the skin of the human patient, dissecting an area of the pelvic bone on the opposite side from acetabulum, creating a hole in the dissected area which passes through the pelvic bone and into the hip joint using the instrument according to any of the embodiments above, and providing at least one hip joint surface into the hip joint, through the hole in the pelvic bone. The hip joint surface could comprise the medical device according to any of the embodiments above.

According to one embodiment, the step of cutting the skin of the human patient could be performed in the abdominal wall, the inguinal area, the pelvic region or the abdominal region of the patient.

The laparoscopic/arthroscopic method comprises the steps of inserting a needle or a tube like instrument into the abdominal region, pelvic region or inguinal region of the patient's body, using the needle or tube like instrument to fill the patient's body with gas, placing at least two laparoscopic/arthroscopic trocars in the patient's body, and inserting a camera through one of the laparoscopic/arthroscopic trocars into the patient's body. At least one dissecting tool is inserted through one of said at least two laparoscopic/arthroscopic trocars after which an area of the pelvic bone on the opposite side from the acetabulum is dissected. Furthermore the method comprises the steps of creating a hole in said dissected area that passes through the pelvic bone and into the hip joint of the human patient using the instrument according to any of the embodiments above, and providing at least one hip joint surface to the hip joint, through the hole in the pelvic bone. The hip joint surface could comprise the medical device according to any of the embodiments above.

According to one embodiment, the step of inserting a needle or tube like instrument is performed in the abdominal wall, the inguinal area, the pelvic region or the abdominal region of the patient.

The step of dissecting an area of the pelvic bone performed in both the surgical and the laparoscopic/arthroscopic method could be performed in the abdominal cavity, an area between peritoneum and the pelvic bone, an area of the pelvic bone and surrounding tissue, the pelvic area or an area of the pelvic bone that comprises the inguinal area. Dissecting a combination of the above mentioned areas is also conceivable.

Further Steps of the Operation

The surgical or laparoscopic/arthroscopic method could further comprise the step of reaming the caput femur and/or the acetabulum, e.g. by means of an expandable reamer.

According to one embodiment the artificial hip joint surface could be fixated to the pelvic bone or to the caput femur after the step of providing the hip joint surface. The fixation could be done by means of mechanical fixating members, such as screws or plates, adhesive, bone cement, or a combination thereof. When the artificial hip joint surface has been placed in the hip joint, the surgical or laparoscopic/arthroscopic method could further comprise the step of closing the hole in the pelvic bone using a bone plug, a prosthetic part, bone cement, or a combination thereof.

According to another embodiment the artificial hip joint surface is provided by means of a mould placed in the hip joint through a hole in the pelvic bone, the hip joint capsule or the femur bone. Said artificial hip joint surface could comprise an artificial acetabulum surface and/or an artificial caput femur surface. After the mould has been inserted into the hip joint a fluid is injected which serves as an artificial caput femur surface after hardening. It is conceivable that said mould is resorbable by the human body or made of a material adapted to melt.

According to one embodiment the artificial hip joint surface is provided by injecting a fluid into a sealed area of the hip joint. Said artificial hip joint surface could comprise an artificial acetabulum surface and/or an artificial caput femur surface. The sealed area is sealed by means of at least one sealing member placed in the hip joint through a hole in the pelvic bone, the hip joint capsule or the femur bone. It is conceivable that said at least one sealing member is resorbable by the human body or made of a material adapted to melt.

After the steps of the surgical method have been performed, the instruments are withdrawn and the skin is closed using sutures or staples.

Acetabulum Surfaces

According to one embodiment the surgical or laparoscopic/arthroscopic method comprises the step of providing an artificial acetabulum surface connecting with the pelvic bone, and carrying the load placed on the caput femur from the weight of said patient by the connection with the pelvic bone. It is conceivable that the diameter of the hole is larger than the largest diameter of the artificial acetabulum surface thus allowing the artificial acetabulum surface to pass through the hole in its entirety, however it is also conceivable that said hole is smaller than the largest diameter of the artificial acetabulum surface thus hindering the artificial acetabulum surface from passing through the hole, which makes it possible for the edges of said hole to carry the load placed on the acetabulum from the weight of the patient.

According to one embodiment the artificial acetabulum surface could comprise at least one supporting member which in turn could comprise at least one screw, adhesive, at least one plate, bone cement, a section of the artificial acetabulum surface or a combination of the mentioned alternatives. It is also conceivable that the supporting member comprises a first and second part. The second part is displaceable in relation to the first part and adapted to carry a load by the connection with the pelvic bone, and carries the load when displaced.

According to one embodiment the artificial acetabulum surface comprises at least two acetabulum surface parts. The at least two artificial acetabulum surface parts are adapted to be connected to each other after insertion in a hip joint of a human patient to form an artificial acetabulum surface. The two artificial caput femur surface parts could be adapted to be mechanically connected using at least one of, screws, form fitting, welding, and/or adhesive. The artificial acetabulum being severable enables the insertion of the artificial acetabulum surface through a hole smaller than the artificial acetabulum surface, which makes it possible for the edges of said hole to carry the load placed on the acetabulum from the weight of the patient. The surgical or laparoscopic/arthroscopic method could comprise the steps of inserting said parts through said hole into the hip joint of a human patient, mounting said parts together or moving said parts in relation to each other after insertion in the hip joint and thereby forming an artificial acetabulum surface.

According to another embodiment the artificial acetabulum surface could be adapted to have a varying largest diameter for insertion through a hole in the pelvic bone from the opposite side from acetabulum. Since the largest diameter of the artificial acetabulum surface is adapted to vary between being both smaller and larger than the hole in the pelvic bone, the hole could having a diameter smaller than the largest diameter of the artificial acetabulum surface.

The surgical or laparoscopic/arthroscopic method could comprise the step of inserting the artificial acetabulum surface adapted to have a varying largest diameter through the hole in the pelvic bone. In this embodiment it is conceivable that the artificial acetabulum surface is adapted to be flexible in its construction, thus enabling the insertion of said artificial acetabulum surface through a hole in the pelvic bone that is smaller than said largest diameter of the artificial acetabulum surface. The flexible part of the artificial acetabulum surface could further be adapted to expand after insertion through the hole making the largest diameter of the artificial acetabulum surface larger than the diameter of the hole in the pelvic bone, thus hindering the artificial acetabulum surface from passing through the hole.

According to one embodiment the surgical or laparoscopic/arthroscopic method comprises using an artificial acetabulum surface having at least one first size related to an insertion through a hole, a first hole being smaller than said first size artificial acetabulum surface do not allow passage of the artificial acetabulum surface through said hole. The artificial acetabulum surface is adapted to vary said first size, for allowing insertion through said first hole in the pelvic bone from the opposite side from acetabulum of the human patient, said artificial acetabulum surface is adapted to change said first size to at least one second size, being smaller than said first hole for allowing said insertion through said first hole of said artificial acetabulum surface, including the method step of: Varying the size of the artificial acetabulum surface between being both smaller and larger than said first hole in the pelvic bone.

According to yet another embodiment the artificial acetabulum surface is created using a mould or a sealed area possible to use as mould. The method could further comprise the step of injecting a fluid into said mould or sealed area, the fluid serves as an artificial acetabulum surface when it hardens.

The mould or sealing members could be made of a resorbable material and be placed in the hip joint through at least one of the hip joint capsule, the pelvic bone, or the femur bone. The mould or sealing members could be placed in the hip joint using manual manipulation or an instrument adapted therefor.

The surgical or laparoscopic/arthroscopic method could comprise the step of reaming the acetabulum or the caput femur, in which case the reamer could be expandable for reaming an area larger than the hole through which the reamer is inserted.

The step of creating a hole in the pelvic bone could be performed using an instrument comprising a driving member, a bone contacting organ in connection with said driving member, an operating device adapted to operate said driving member. The bone contacting organ is adapted to create a hole in the acetabulum area starting from the abdominal side of the pelvic bone of the human patient through repetitive or continuous movement. The surgical instrument could further comprise a bend comprising at least one of the following: a fixed angle, an adjustable angle, or a parallel displaced part or section. The bone contacting organ of the surgical instrument could further be adapted to be replaceable to a bone contacting organ adapted to ream at least one of the acetabulum and the caput femur.

Caput Femur Surface

The surgical or laparoscopic/arthroscopic method could further comprise the step of placing an artificial caput femur surface onto caput femur on the opposite side of collum femur and, when mounted in the joint, in the acetabulum cup or an artificial replacement therefor. The artificial caput femur surface, comprises at least one first beyond part of said artificial caput femur surface adapted to cover and/or go into the bone of the caput femur on at least a part of the caput femur beyond the maximum diameter of the caput femur, away from the acetabulum cup towards said collum femur, when mounted on the caput femur in it's functional position in the joint. The at least one first beyond part have a closest perpendicular distance to said centre axis, which is smaller than the distance between the periphery of said maximum diameter of the caput femur and said centre axis. The method further comprises the step of mounting said artificial caput femur surface, including the first beyond part thereof, on the caput femur in said functional position. This creates a more stable position of said artificial caput femur surface.

According to one embodiment, an artificial caput femur surface is adapted to be in connection with the acetabulum surface. It is conceivable that the diameter of the hole is larger than the largest diameter of the caput femur thus allowing the caput femur to pass through the hole. However it is also conceivable that said hole is smaller than the largest diameter of the caput femur thus hindering the caput femur from passing through the hole.

The artificial caput femur surface could comprises at least two caput femur surface parts adapted to be connected to each other after insertion in a hip joint to form an artificial caput femur surface. According to one embodiment the at least two artificial caput femur surface parts are inserted through a hole in the pelvic bone from the opposite side from acetabulum, said hole having a diameter less than the largest diameter of said artificial caput femur surface. The mechanical connection that connects the parts of the artificial caput femur surface could be created using screws, form fitting, welding, sprints, band, adhesive or some other mechanical connecting member. The surgical or laparoscopic/arthroscopic method could comprise the steps of: mounting said at least two artificial caput femur surface parts on caput femur to form an assembled medical device. The assembled medical device could be hollow. The method further comprises the steps of fixating said assembled medical device to the caput femur and surrounding, at least partly, the caput femur beyond said maximum diameter of the caput femur towards collum femur, the shape of said assembled medical device mechanically stabilizing the device when mounted on the caput femur.

According to another embodiment the artificial caput femur surface could be adapted to have a varying largest diameter for insertion through a hole in the pelvic bone from the opposite side from acetabulum of the human patient. Since the largest diameter of the artificial caput femur surface is adapted to vary between being both smaller and larger than the hole in the pelvic bone, the hole could have a diameter smaller than the largest diameter of the artificial caput femur surface.

The surgical or laparoscopic/arthroscopic method could comprise the step of inserting the artificial caput femur surface adapted to have a varying largest diameter through the hole in the pelvic bone. In this embodiment it is conceivable that the artificial caput femur surface is adapted to be flexible in its construction, thus enabling the insertion of said artificial caput femur surface through a hole in the pelvic bone that is smaller than said largest diameter of the artificial caput femur surface. The flexible part of the artificial caput femur surface could further be adapted to expand after insertion through the hole making the largest diameter of the artificial caput femur surface larger than the diameter of the hole in the pelvic bone, thus hindering the artificial caput femur surface from passing through the hole.

According to one embodiment the surgical or laparoscopic/arthroscopic method further comprises the step of introducing said hollow medical device onto the caput femur, having a diameter or cross sectional distance of said opening larger than the diameter of the caput femur and having at least the smallest distance of said opening diameter or cross sectional distance becoming smaller than said maximum diameter of the caput femur, after mounting said device on the caput femur and in a functional position thereon.

According to another embodiment the method further comprises using at least one slit for varying said opening diameter or opening cross sectional distance, thus allowing the device to be introduced and mounted on the caput femur. The varying diameter according to any of the embodiments can be changed in relation to the mounting of said device onto the caput femur. The changing of said opening could include at least one of the following steps: Increasing an at least partly diameter or cross sectional distance to be able to mount said device on the caput femur, decreasing said at least partly diameter or cross sectional distance, to enable a stable position of the device on the caput femur when mounted thereon.

According to yet another embodiment the surgical or laparoscopic/arthroscopic method comprises the step of providing an artificial caput femur comprising at least two artificial caput femur surface parts. The method further comprises the step of inserting said at least two artificial caput femur surface parts through said hole in the pelvic bone from the opposite side from acetabulum of a human patient, said hole having a diameter less than the largest diameter of the caput femur. The at least two artificial caput femur surface parts could be adapted to be mechanically connected using at least one of the following: at least one screw, form fitting, welding, adhesive, at least one sprint, at least one band or wire, or other mechanical connecting members.

According to one embodiment the surgical or laparoscopic/arthroscopic method comprises providing an artificial caput femur surface adapted to have a varying largest diameter for insertion through a hole in the pelvic bone from the opposite side from acetabulum of the human patient. The hole has a diameter less than the largest diameter of said artificial caput femur surface of the human patient. The method further comprises the step of varying said largest diameter of said artificial caput femur surface between being both smaller and larger than the hole in the pelvic bone. The method steps could be performed by inserting said artificial caput femur surface through said hole in the pelvic bone and expanding said flexible construction of said artificial caput femur surface after said insertion through said hole making said artificial caput femur surface larger than the caput femur, thus not allowing passage through said hole in the pelvic bone.

According to one embodiment the surgical or laparoscopic/arthroscopic method comprises providing an artificial caput femur surface, wherein said artificial caput femur surface is hollow and has a greatest internal cross-sectional area and an opening with an area less than said greatest internal cross-sectional area of said artificial caput femur surface, when mounted on the caput femur of the human patient. The artificial caput femur surface further comprises at least one slit allowing the mounting of said artificial caput femur surface on the caput femur, which requires an opening area larger than the largest cross-sectional area of caput femur, and decreasing the size of said opening area to become smaller than said greatest internal cross-sectional area of said hollow medical device after said mounting on the caput femur.

According to one embodiment the artificial caput femur surface is frustum spherical.

According to one embodiment the surgical or laparoscopic/arthroscopic method comprises the steps of inserting said at least two artificial caput femur surface parts into the hip joint of the human patient and mounting said at least two artificial caput femur surface parts on the hip joint of the human patient to form said artificial caput femur surface, wherein said artificial caput femur surface is mechanically fixated to the caput femur by means of said mounting on the caput femur so that said artificial caput femur surface can not be removed without dismounting said at least two artificial caput femur surface parts.

According to another embodiment the artificial caput femur surface is created inside of the hip joint using a mould or a sealed area. The method further comprises the step of injecting a fluid into a sealed area, the fluid serving as an artificial caput femur surface when it hardens.

According to one embodiment the surgical or laparoscopic/arthroscopic method comprises the step of placing a mould in the hip joint. In this embodiment it is further conceivable that said mould is placed in the hip joint through at least one of, the hip joint capsule, the pelvic bone, or the femur bone using an instrument adapted therefor. This instrument could be equipped with a fixed angle, an adjustable angle or a parallel displaced part or section for improved reach.

According to another embodiment the above mentioned surgical or laparoscopic/arthroscopic method comprises the step of placing at least one sealing member in the hip joint. In this embodiment it is further conceivable that the mould is placed in the hip joint through at least one of, the hip joint capsule, the pelvic bone or the femur bone using an instrument adapted therefor. This instrument could be equipped with a fixed angle, an adjustable angle or a parallel displaced part or section for improved reach.

According to above mentioned embodiments the artificial caput femur or acetabulum surface could comprises at least two artificial acetabulum/caput femur surface parts. According to these embodiments the surgical or laparoscopic/arthroscopic method could comprise the step of inserting these at least two artificial acetabulum/caput femur surface parts, in which case a surgical instrument adapted therefor could be used. Said instrument could be adapted to insert the parts through at least one of, the hip joint capsule, the pelvic bone, or the femur bone. It is furthermore conceivable that said instrument is equipped with a fixed angle, an adjustable angle or a parallel displaced part or section for improved reach.

According to one embodiment, the driving member and bone contacting organ together from an elongated member, wherein said elongated member is adapted to be supported at first supporting point in the femoral bone and in a second supporting point in a pelvic bone.

According to one embodiment, an operation device is connected to give force to said driving member outside the body, lateral on the opposite side of said hip joint outside the opposite side ilium pelvic bone outside the body.

According to one embodiment, the elongated member is adapted to receive said force from an operation device in the abdomen.

According to one embodiment, the elongated member is adapted to receive said force from an operation device outside the body, lateral of the proximal femoral bone.

According to one embodiment, said driving member and bone contacting organ together from an elongated member, placing said elongated member achieving a first supporting point for the bone contacting organ in the femoral bone and a second supporting point in a pelvic bone.

According to one embodiment, the method could comprise the steps of connecting an operation device giving force to said driving member from outside the body, lateral on the opposite side of said hip joint outside the opposite side ilium pelvic bone outside the body.

According to one embodiment, said elongated member is receiving said force from an operation device in the abdomen.

According to one embodiment, said elongated member is adapted to receive said force from an operation device outside the body, lateral of the proximal femoral bone.

Please note that any embodiment or part of embodiment as well as any method or part of method could be combined in any way. All examples herein should be seen as part of the general description and therefore possible to combine in any way in general terms.

BRIEF DESCRIPTION OF DRAWINGS

The embodiments are now described, by way of example, with reference to the accompanying drawings, in which:

FIG. 18c shows an embodiment of the instrument being a pelvic drill, FIGS. 18d and 18e shows an embodiment of the instrument being a pelvic drill FIG. 27 shows an artificial caput femur surface in section, FIG. 28a shows an artificial caput femur surface according to a first embodiment, FIG. 28b shows an artificial caput femur surface when fixated to the caput femur, FIG. 32a shows an artificial caput femur surface 45 according to a fifth embodiment, FIG. 32b shows an artificial caput femur surface 45 in section, FIG. 33a,b,c shows an artificial caput femur surface 45 according to a sixth embodiment, FIG. 34a,b,c shows an artificial caput femur surface 45 according to a seventh embodiment.

FIG. 44 shows an artificial acetabulum surface according to a first embodiment, FIG. 45a shows an artificial acetabulum surface according to a second embodiment, FIG. 45b shows an artificial acetabulum surface according to the second embodiment in further detail, FIG. 45c shows an artificial acetabulum surface when assembled, FIG. 46a shows an artificial acetabulum surface according to a third embodiment, FIG. 46b shows an artificial acetabulum surface according to the third embodiment when assembled, FIG. 46c shows a connection function of the artificial acetabulum surface according to the third embodiment, FIG. 47a shows an artificial acetabulum surface according to a fourth embodiment, FIG. 47b shows the function of the artificial acetabulum surface according to the fourth embodiment, FIG. 47c shows an artificial acetabulum surface according to a fourth embodiment in its folded state, FIG. 47d shows the connection function of the artificial acetabulum surface according to a fourth embodiment, FIG. 48a shows an artificial acetabulum surface according to a fifth embodiment, FIG. 48b shows an artificial acetabulum surface according to the fifth embodiment in its folded state.

FIG. 57 shows the filling of a sealed area inside of a hip joint using an instrument that operates through the pelvic bone, FIG. 58 shows the filling of a mould inside of a hip joint using an instrument that operates through the femur bone.

DETAILED DESCRIPTION

Figure 1:
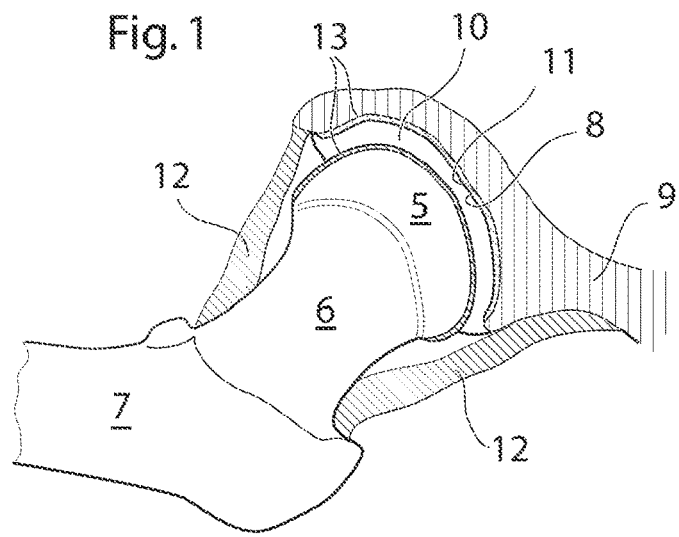
FIG. 1 shows a hip joint in section.

In the following a detailed description of embodiments will be given. In the drawing figures, like reference numerals designate identical or corresponding elements throughout the several figures. It will be appreciated that these figures are for illustration only and are not in any way restricting the scope. Thus, any references to direction, such as "up" or "down", are only referring to the directions shown in the figures. Also, any dimensions etc. shown in the figures are for illustration purposes.

External portion is to be understood as a portion of the pelvic drill being adapted to remain on the outside of the patient when the pelvic drill is in use. The external portion could comprise the operating device and at least a portion of the driving member. In other embodiments it is conceivable that the external portion only comprises a handling portion and/or a power supply portion for powering the operating device.

Internal portion is to be understood as a portion of the pelvic drill being adapted to be inserted into the body of the patient, when in use. The internal portion could comprise the bone contacting organ and at least a portion of the driving member.

The pelvic drill disclosed herein is a surgical instrument, and is sometimes referred to as surgical instrument, i.e. the expression pelvic drill and surgical instrument is sometimes used alternating and for the purpose of this application these expressions are to be considered as equivalent.

FIG. 1 shows a hip joint of a human patient in section. The hip joint comprises a caput femur 5 placed at the very top of collum femur 6 which is the top part of the femur bone 7. The caput femur is in connection with the acetabulum 8 which is a bowl shaped part of the pelvic bone 9. Both the caput femur surface 10 and the acetabulum surface 1 is covered with articular cartilage 13 which acts as a cushion in the hip joint. In patients with hip joint osteoarthritis, this articular cartilage 13 is abnormally worn down due to a low grade inflammation. The hip joint is surrounded by the hip joint capsule 12 which provides support for the joint and hinders luxation. After conventional hip joint surgery, penetrating the hip joint capsule 12, the capsule 12 is dramatically weakened due to the limited healing possibilities of its ligament tissue. By performing hip joint surgery without damaging the hip joint capsule 12 the patient can fully recover and place equal amount of strain on an artificial joint as is possible on a natural one.

Figure 2:
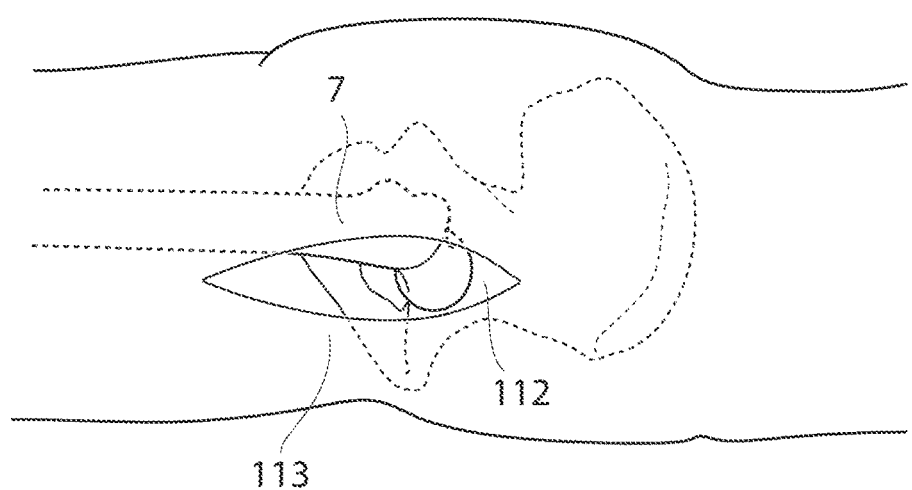
FIG. 2 shows a lateral view of a conventional hip joint surgery.

FIG. 2 shows a lateral view of a conventional hip joint surgery where an incision 112 is made in the tight 113 enabling the surgeon to reach the femur bone 7 on which the caput femur 5 is located. In a conventional hip joint surgery the hip joint is accessed through the hip joint capsule.

Figure 3:
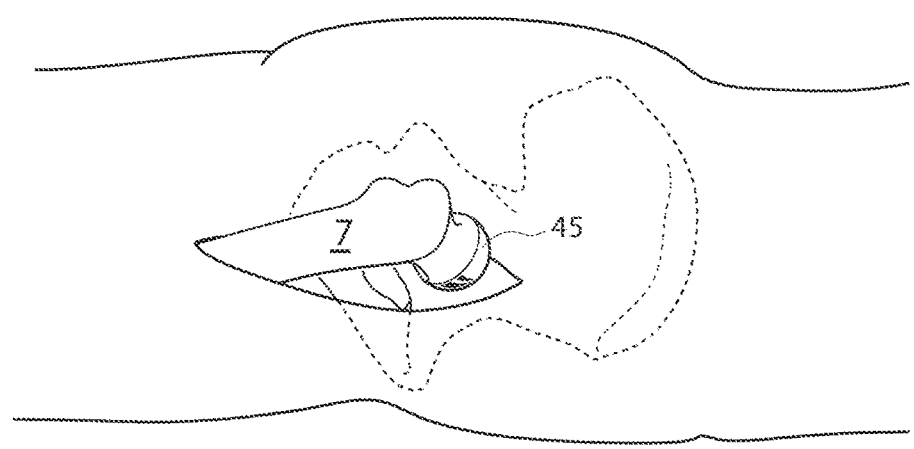
FIG. 3 shows an artificial caput femur being used in conventional surgery.

FIG. 3 shows the placing of an artificial caput femur surface 45 on the caput femur 5 in conventional surgery.

Figure 4:
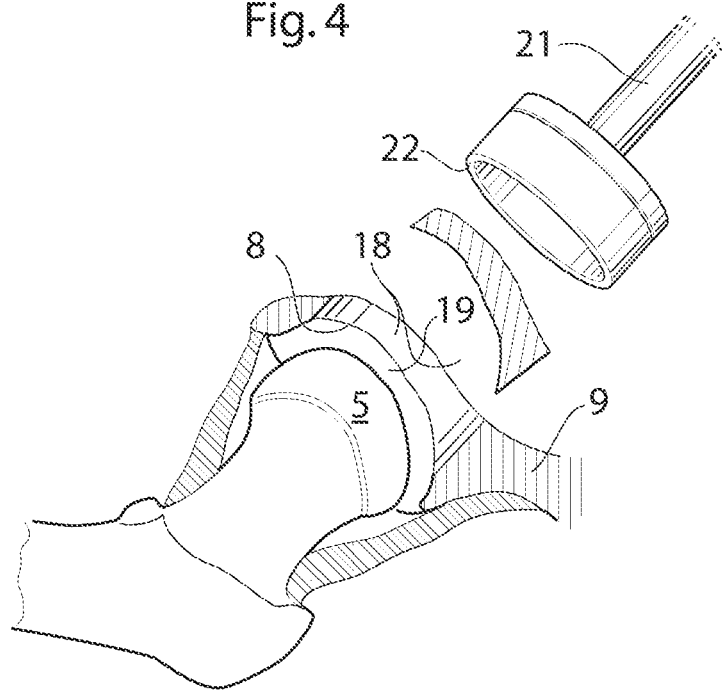
FIG. 4 shows a hip joint in section when a hole is created in the pelvic bone.

FIG. 4 shows an instrument for creating a hole 18 in the pelvic bone 9 according to a first embodiment. The instrument comprises a driving member 21*a, b*. The driving member 21*a,b* could be a shaft, a rod, a belt, a chain or any other element suitable for transferring force or torque. The instrument also comprises a bone contacting organ 22 which is adapted to create the hole 18 in the pelvic bone 9. The bone contacting organ 22 could have a sawing, drilling or milling effect using sharp objects; it is furthermore conceivable that said bone contacting organ 22 creates a hole using water, abrasive fluids, laser or radiation. The instrument also comprises an operating device 23a (shown in FIGS. 6-8) adapted to operate the driving member 21a,b. The operating device could comprise an electrical, hydraulic, mechanical, pneumatic or magnetic engine and it could be adapted to create a rotating, oscillating, vibrating or repetitive movement.

Figure 5:
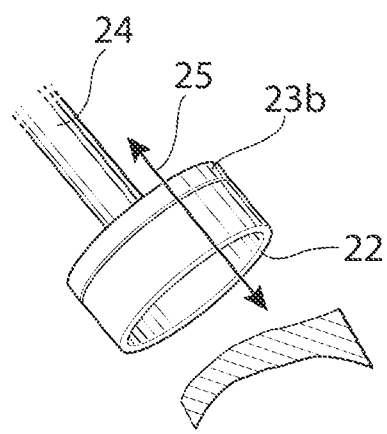
FIG. 5 shows an instrument according to a second embodiment.

FIG. 5 shows an instrument according to a second embodiment in which the operating device 23b is placed in direct connection with the bone contacting organ 22. In this case the operating device 23b also serves as driving member. In this construction a handle portion 24 could be attached to the instrument, facilitating the surgeons handling of said surgical instrument. To improve the reach of the surgical instrument the handle portion 24 could be attached perpendicular to the hole-creating direction 25 of the surgical instrument, it is furthermore conceivable that the handle portion 24 is bent by means of a parallel displaced part or section, a fixed angle, an adjustable angle or a flexible part or section.

Figure 6A:
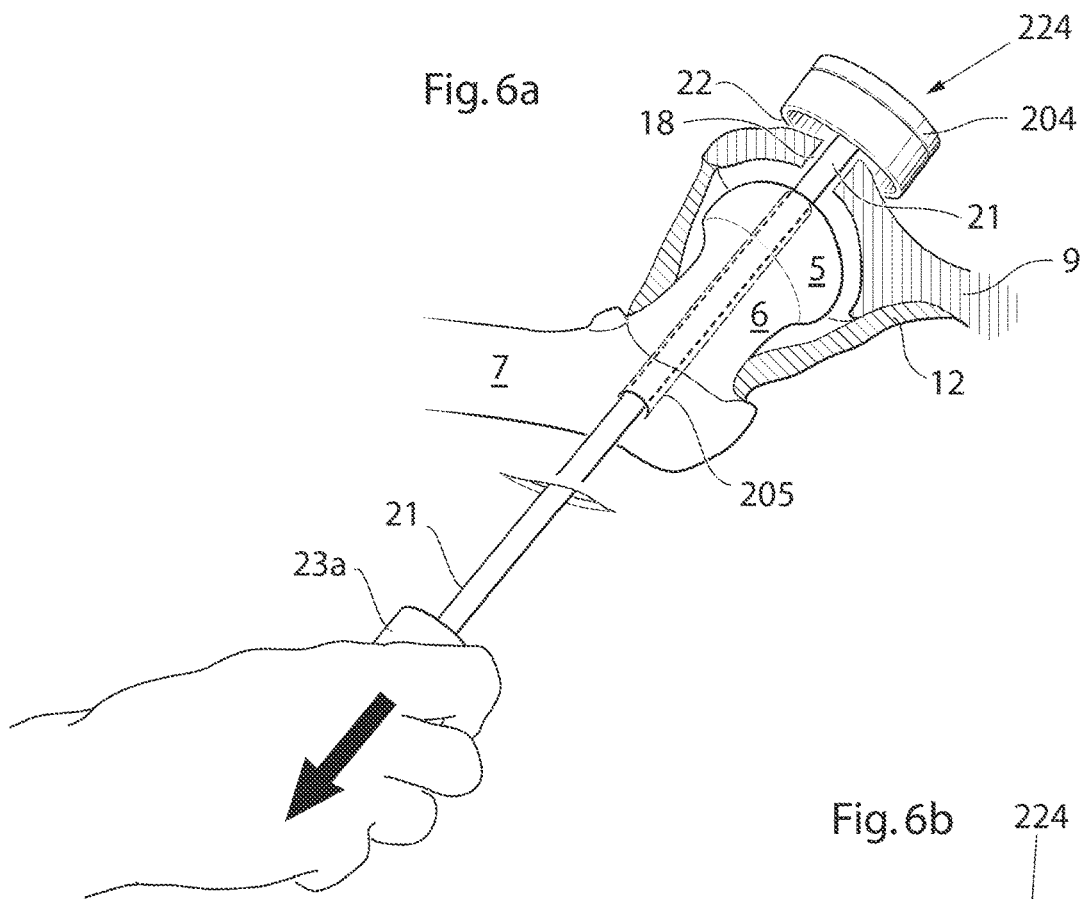
FIG. 6a shows the creation of a hole from the thigh region.

FIG. 6a shows an instrument according to a second embodiment in which the instrument comprises a tool 224 for creating a hole 18 in the pelvic bone 9 is fixated to the tool fixating the driving member 21. The driving member 21 is placed in a hole 205 in the femoral bone 7, the collum femur 6 and the caput femur 5 enabling the operating device to be placed outside of the thigh region of the patient, thereby enabling the surgeon to generate a large force in a length axis of the driving member 21. When the tool 224 for creating a hole 18 in the pelvic bone 9 is applied to the driving member 21, the driving member 21 is preferably operated using an operating device 23a, which could be an electrical, hydraulic or pneumatic operating device 23a. The tool 224 for creating a hole in the pelvic bone 9 comprises a bone contacting organ 22 which is adapted to create the hole 18 in the pelvic bone 9 through a sawing, drilling or milling process powered by a rotating, vibrating or oscillating movement of the driving member 206.

Figure 6B:
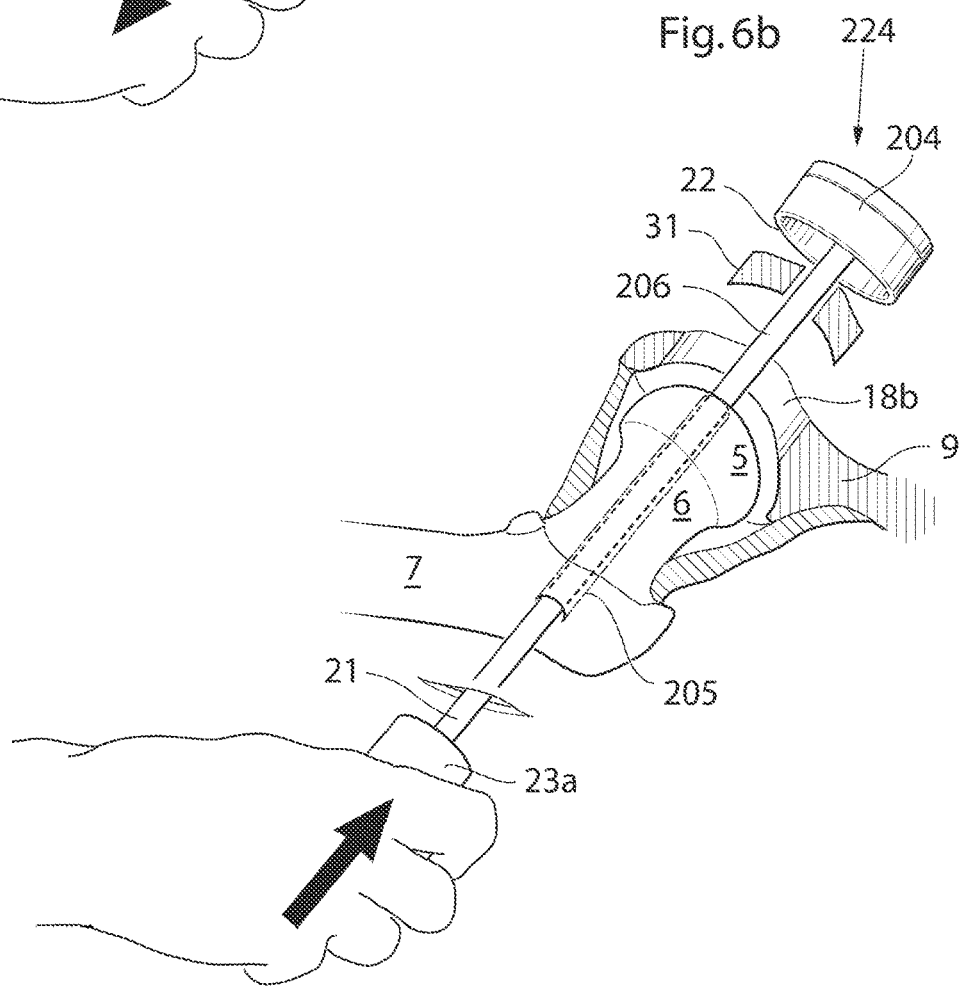
FIG. 6b shows the creation of a hole from the thigh region, in further detail.

FIG. 6b shows the hip joint in section when a hole 18b in the pelvic bone 9 has been created. According to the embodiment shown the hole 18b is created through the creation of a bone plug 31 which can be adapted to be replaced after the steps of the operation performed through the hole 18b in the pelvic bone 9 has been concluded.

Figure 7A:
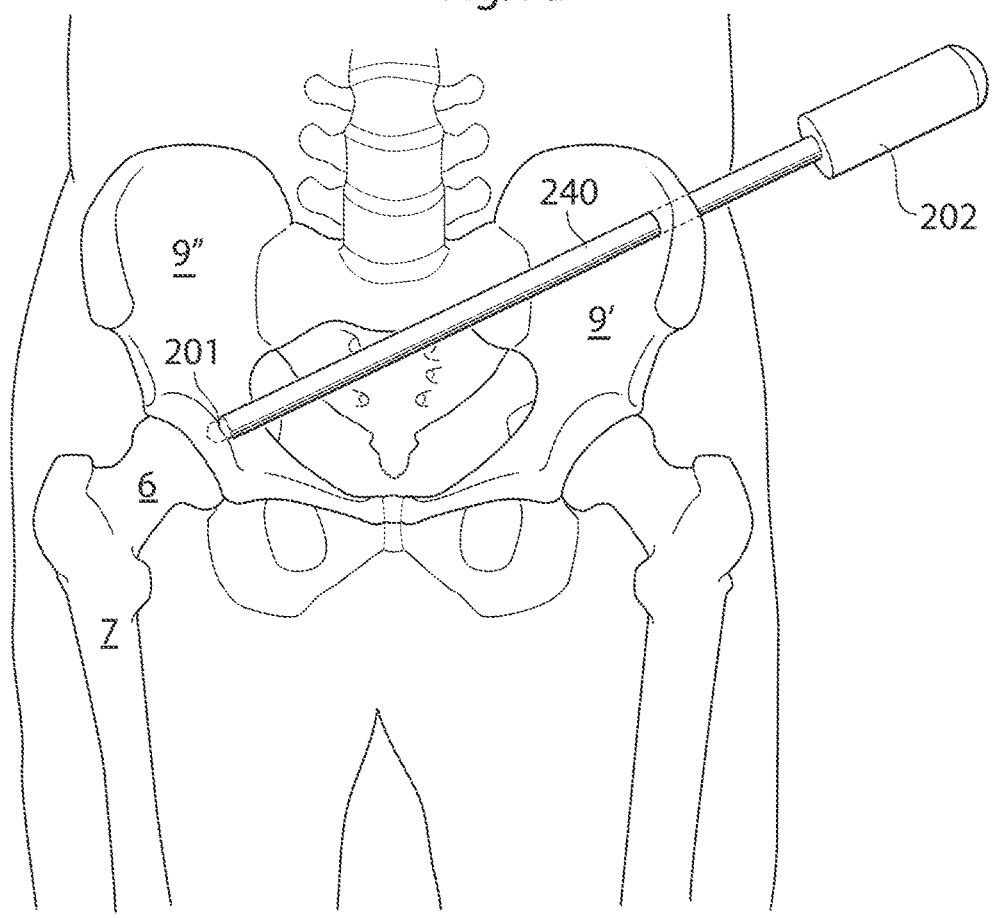
FIG. 7a shows the creation of a hole from the opposite side.

FIG. 7a shows an embodiment in which a hole is created in two different parts of the pelvic bone 9. A drilling member 201 is first brought to the left part of the pelvic bone 9' for creating a hole in the left part of the pelvic bone 9. The drilling member thereafter continues through the abdominal and/or pelvic region and reaches the right part of the pelvic bone 9" where a second hole is created reaching into the hip joint. The drilling member 201 is powered by an operating device 202, which could be a powered operating device, such as an electrical, hydraulic or pneumatic motor. According to another embodiment the drilling member 201 is manually operated. The drilling member further comprises a protective sleeve 240 adapted to protect the organs and tissue of the body from the drilling member 201 when advancing the drilling member through the abdominal and/or the pelvic region. The creation of two holes enables a very stable position of an elongated member which could be placed through the two holes for delivering an action to the hip joint or its surroundings.

Figure 7B:
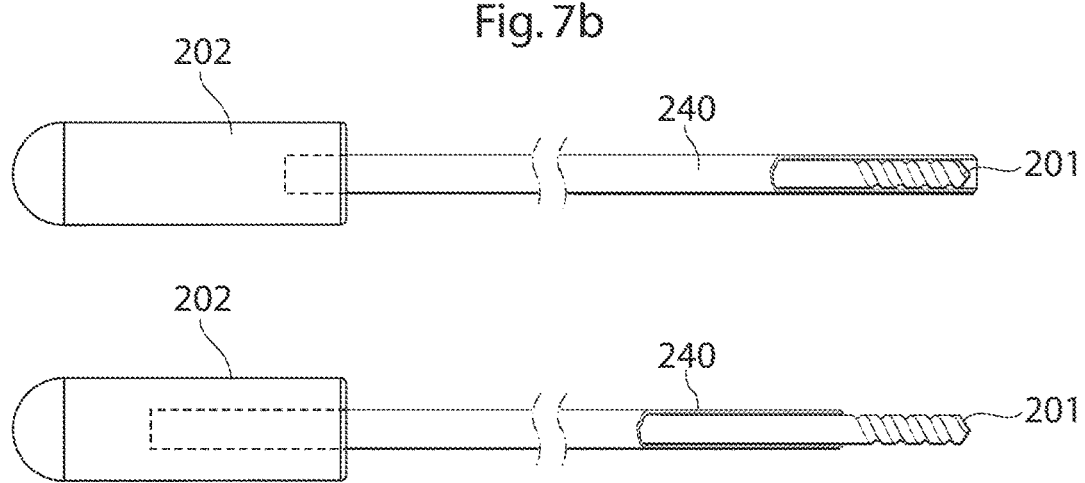
FIG. 7b shows the tool for creating a hole from the opposite side.

FIG. 7b shows the drilling member in further detail, first in a state in which the protective sleeve 240 is advanced for covering the drilling member 201 and thereby protecting the organs and tissue of the human body from the drilling member. Below, the drilling member is shown in a second state, in which the protective sleeve 240 is retracted and thereby exposing the drilling member 201 and enabling the drilling member 201 to create a hole in bone.

After the hole has been created along a force transferring member or elongated member, according to any of the embodiments herein, could be inserted through the holes for delivering an action to the hip joint or its surroundings. The force transferring member could be a tubular or solid shaft, or a flexible member such as a wire.

Figure 8A:
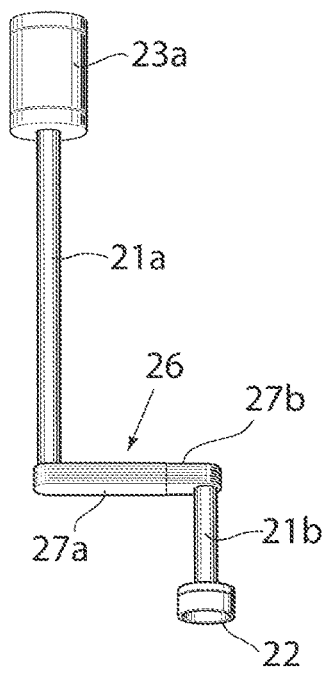
FIG. 8a shows an instrument according to a third embodiment.

FIG. 8a shows an instrument according to a third embodiment wherein the instrument further comprises a parallel displaced part or section 26. The parallel displaced part or section 26 improves the reach of the instrument and enables the creation of a hole 18 in the pelvic bone 9 from the opposite side from acetabulum 8. According to the embodiment shown in FIG. 6 the parallel displaced part or section 26 has a telescopic function by means of the parallel displaced part or section 26 being divided in to a first and second part 27a, b, wherein the second part 27b can slide in and out of the first part 27a.

Figure 8B:
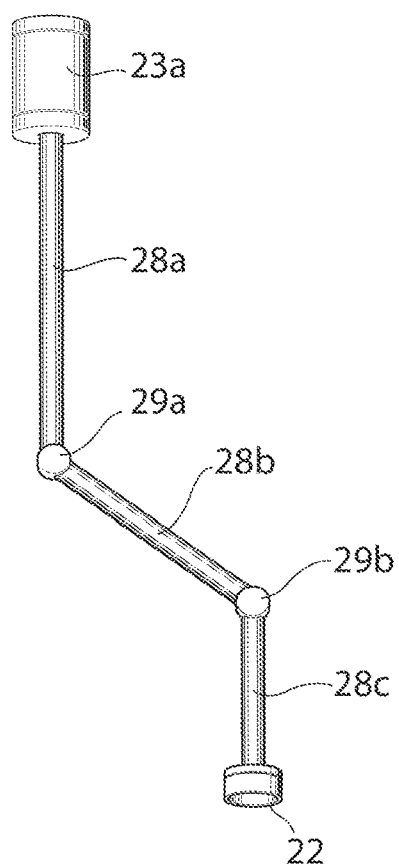
FIG. 8b shows an instrument according to a fourth embodiment.

FIG. 8b shows an instrument according to a fourth embodiment wherein said instrument comprises a driving member 28a,b,c with two angle adjusting members 29a,b. The angle adjusting members 29a,b could be adjustable for varying the angle of said driving member 28a,b,c or fixed in an angle suitable for creating a hole in the pelvic bone 9 from the opposite side from acetabulum 8. In another embodiment (not shown) the part of the driving member 28c in connection with the bone contacting organ 22 could be very short enabling the instrument to operate very close to the pelvic bone 9 when creating a hole 18 in the pelvic bone 9.

Figure 8C:
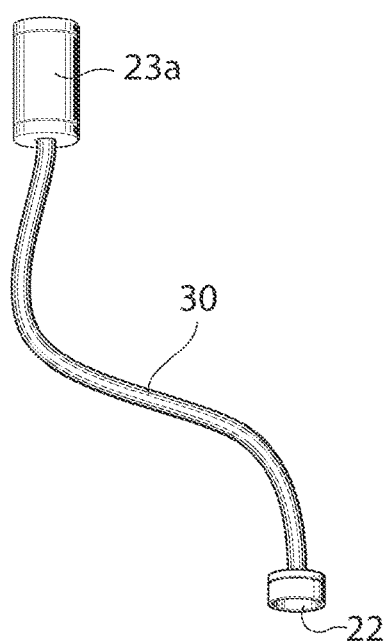
FIG. 8c shows an instrument according to a fifth embodiment.

FIG. 8c shows an instrument according to a fifth embodiment wherein the driving member 30 is flexible, enabling said driving member 30 to be very precisely adjusted to create a hole 18 in the pelvic bone 9 of the patient. The stiffness of said driving member 30 could range from completely flexible to essentially stiff to fit the surroundings of the particular operation.

Figure 9A:
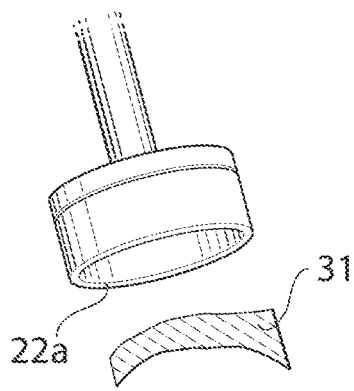
FIG. 9a shows an instrument when creating a bone plug.

FIG. 9a shows a bone contacting organ according to an embodiment wherein the bone contacting organ 22a is adapted to create a bone plug 31. The bone plug 31 could be adapted to be replaced into said hole 18 after the surgical or laparoscopic/arthroscopic steps performed in the hip joint has been concluded.

Figure 9B:
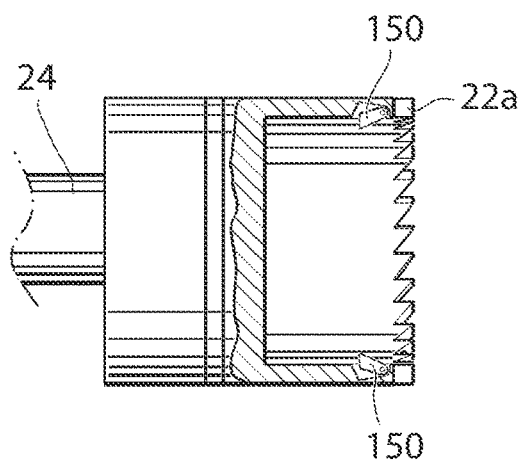
FIG. 9b shows the instrument creating a bone plug in section.

FIG. 9b shows the bone contacting organ according to the first embodiment in section wherein the bone contacting organ 22a is adapted to create a bone plug 31. According to this embodiment the instrument further comprises two holding member 150 for holding said bone plug in place after it has been removed from the pelvic bone of the human patient.

Figure 10:
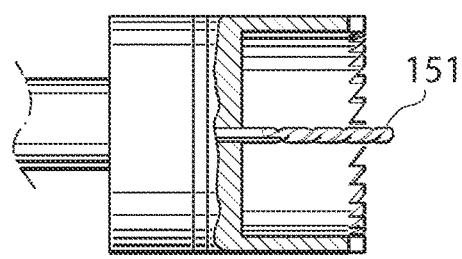
FIG. 10 shows an instrument according to a sixth embodiment.

FIG. 10 shows an instrument according to a sixth embodiment wherein said instrument comprises a stabilizing drill 151 adapted to stabilize the instrument when creating said hole in the pelvic bone from the opposite side from acetabulum.

Figure 11:
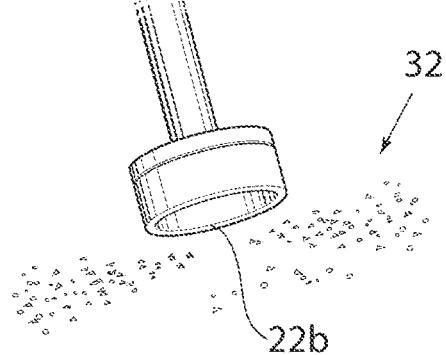
FIG. 11 shows a bone contacting organ according to a second embodiment.

FIG. 11 shows the bone contacting organ according to a second embodiment wherein the bone contacting organ 22b is adapted to create pieces of bone 32 smaller than one cubic cm. when creating said hole 18 in the pelvic bone 9. The small pieces of bone 32 could be transported from the area and out of the body using vacuum power or a hydraulic transport system.

Figure 12:
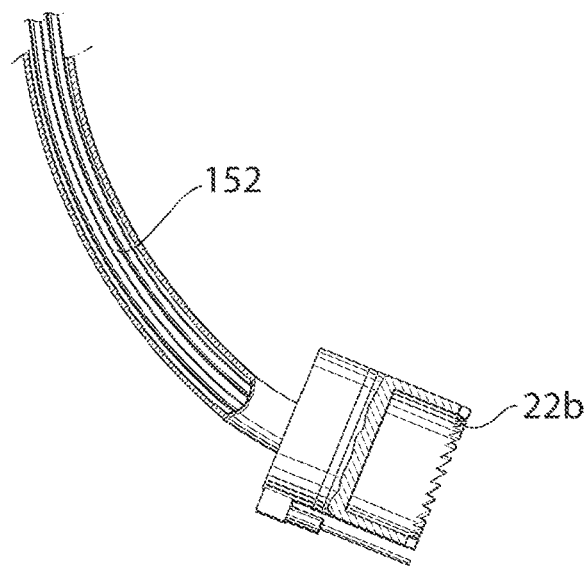
FIG. 12 shows a pneumatic, vacuum powered or a hydraulic transport system.

FIG. 12 shows a pneumatic, vacuum powered or hydraulic transport system 152 for transport of said small pieces of bone. The same system 152 or an additional one could be for rinsing or cooling purposes when creating said hole in the pelvic bone 9.

Figure 13:
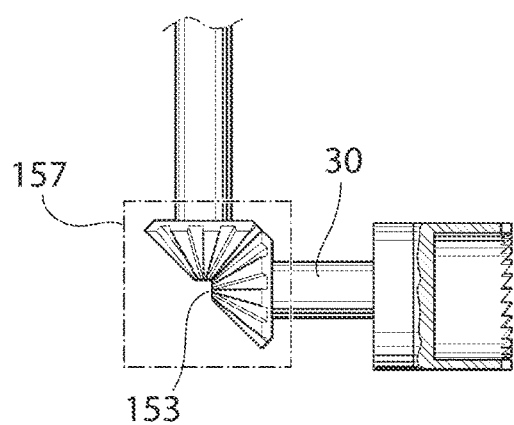
FIG. 13 shows an instrument according to a seventh embodiment.

FIG. 13 shows an instrument according to a seventh embodiment, wherein the driving member 30 comprises at least one worm gear 153 which enables the driving member 30 to be angled. It is also conceivable that said angle could be adjustable in which case said worm gear has a radius (not shown).

Figure 14:
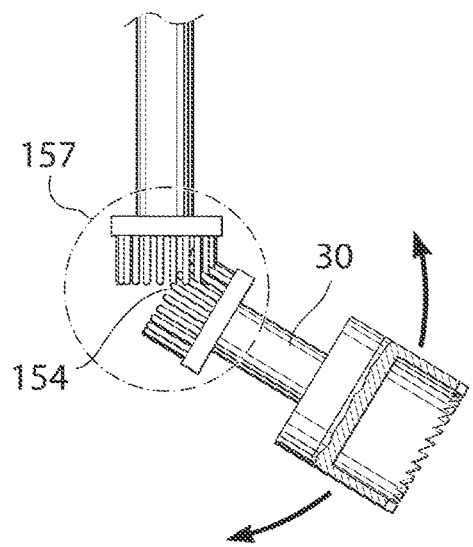
FIG. 14 shows an instrument according to an eight embodiment.

FIG. 14 shows an instrument according to an eight embodiment, wherein the driving member 30 comprises at least one gear wheel 154. In the embodiment shown the two gear wheels 154 is constructed to enable the adjusting of an angle of the driving member 30.

Figure 15:
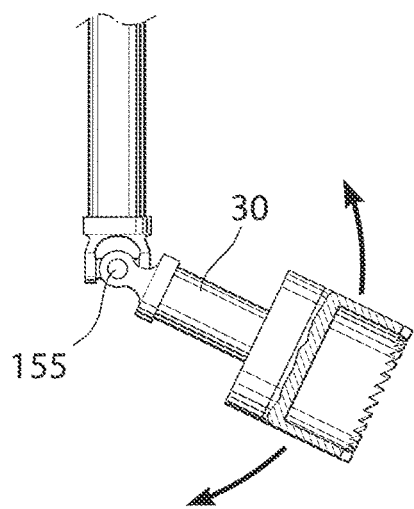
FIG. 15 shows an instrument according to a ninth embodiment.

FIG. 15 shows an instrument according to a ninth embodiment, wherein the driving member 30 comprises at least one universal joint 155, said universal joint enabling the adjusting of an angle of said driving member 30.

Figure 16:
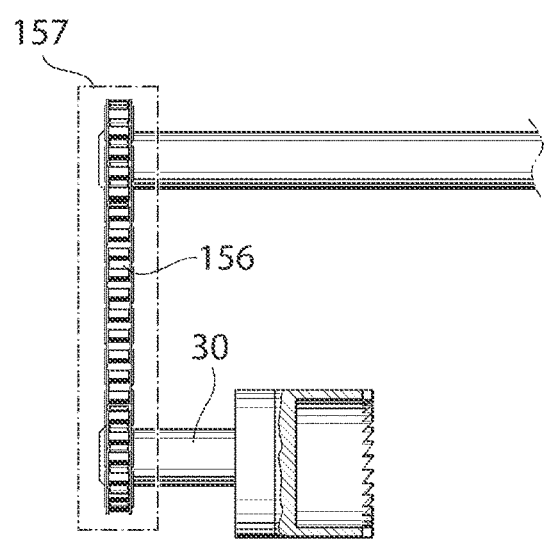
FIG. 16 shows an instrument according to a tenth embodiment.

FIG. 16 shows an instrument according to a tenth embodiment, wherein the driving member 30 comprises at least one chain 156.

According the any of the embodiments above the driving member could comprise a housing 157 shown in FIGS. 13, 14 and 16. Said housing could be adapted to hold a lubricating fluid for lubricating at least a part of said driving member. Said lubricating fluid is preferably a biocompatible lubricating fluid, such as hyaluronic acid.

Figure 17:
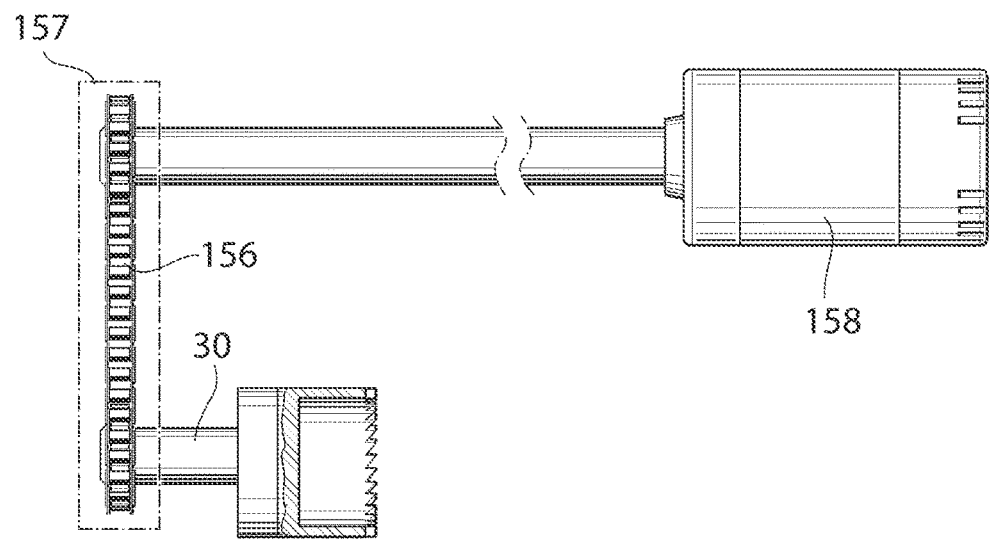
FIG. 17 shows an instrument according to an embodiment where said operating device comprises an electrical motor.

FIG. 17 shows an instrument according to an embodiment where said operating device comprises an electrical motor 158. Said electrical motor is connected to the driving member 30.

Figure 18A:
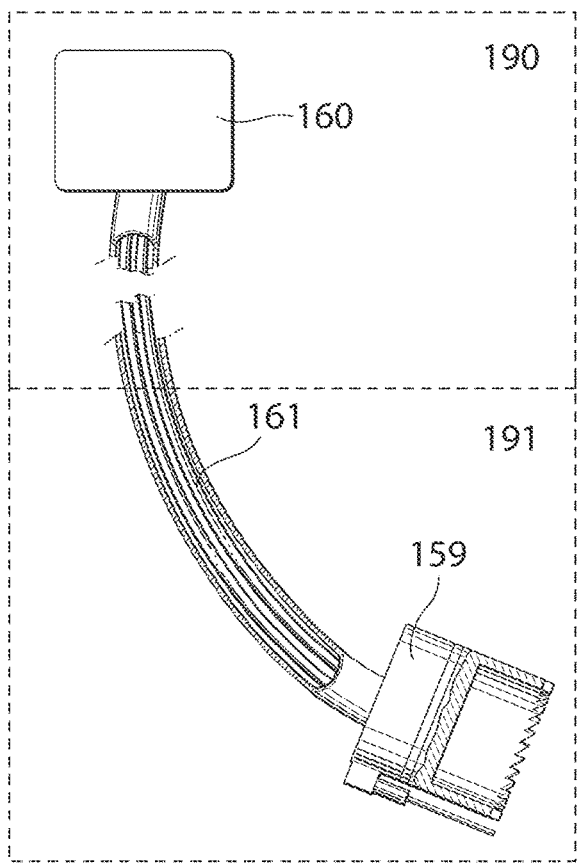
FIG. 18a shows an instrument according to an embodiment wherein said operating device comprises a hydraulic motor.

FIG. 18a shows an instrument being a pelvic drill according to an embodiment wherein said operating device comprises a hydraulic motor 159, hydraulically connected to a hydraulic power source 160 by means of a hydraulic power transport system 161. The hydraulic power source 160 is a portion of the external portion of the pelvic drill adapted to remain outside the body of the patient, whereas the hydraulic motor 159 is a portion of the internal portion adapted to be placed inside the body of the patient when in use.

Figure 18B:
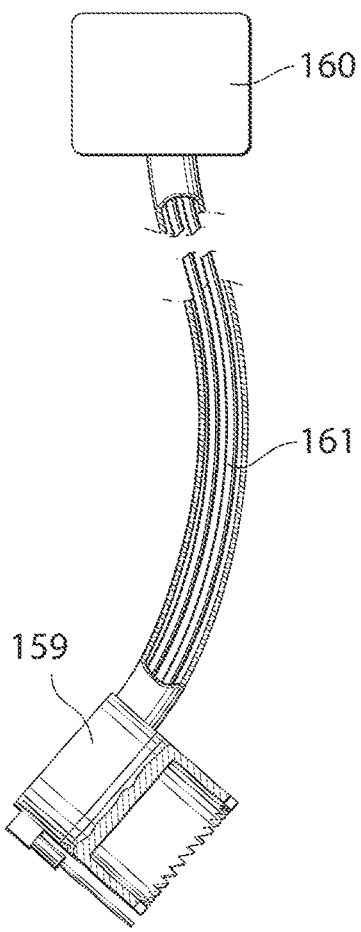
FIG. 18b shows an instrument according to an embodiment wherein said operating device comprises a hydraulic motor according to a second embodiment.

FIG. 18b shows an instrument being a pelvic drill according to an embodiment wherein said operating device comprises a hydraulic motor, but wherein the hydraulic power transport system 161 extends substantially perpendicularly to the hole creation direction.

FIG. 18c shows an embodiment of the instrument being a pelvic drill, wherein the pelvic drill comprises an internal portion 191 adapted to be inserted into the body of the patient, and an external portion 190 adapted to be kept outside the body of the patient when in use. The internal portion 191 comprises a plurality of connectable parts, here being a portion of the driving member 21b and the bone contacting organ 22, which is adapted to be connected to the driving member 21b after insertion of the pelvic drill into the patient. The driving member according to the embodiment shown in FIG. 18c comprises a first elongated portion 21a being partially in the internal portion 191 and partially in the external portion 190, and a connecting portion 21b adapted to connect to the bone contacting organ 22. According to other embodiments the internal portion of the pelvic drill can be divided into further parts making the parts smaller and thus possible to introduce into the body of a patient through a smaller hole, which is needed if the drill is to be used in a key-hole procedure, in which case it could be necessary to insert the parts through a trocar which for example could have a diameter of 18, 20 or 22 mm. The embodiment with multiple connectable parts are applicable to any of the embodiments of the pelvic drill disclosed herein.

FIGS. 18d and 18e shows an embodiment of the instrument being a pelvic drill in which the pelvic drill further comprises a covering member 180 adapted to cover the bone contacting organ 22 such that the bone contacting organ 22 do not damage the tissue of the patient when inserted into the abdominal cavity through an incision in the abdominal region. In the embodiment shown in FIGS. 18d and 18e the covering member 180 are adapted to go on the outside of the bone contacting organ such that the bone contacting organ 22 is retractable into the driving member 21b comprising the covering member. The retractable bone contacting organ 22 also enables the internal portion 191 to be flat in the hole-creation direction, along a length axis of the bone contacting organ 22. The internal portion could for example be as flat as 10 mm, or as flat as 20 mm, or as flat as 30 mm, or as flat as 40 mm, such that internal portion can be moved along the abdominal side of the pelvic bone, close to the pelvic bone, outside of the peritoneum, without entering the abdominal cavity. The retractable bone contacting organ 22 disclosed with reference to FIGS. 18d and 18e can be used in combination with the pelvic drills disclosed in any of the embodiments herein and is not in any way limited to the hydraulic embodiments disclosed with reference to FIGS. 18d and 18e. For example can the retractable bone contacting organ 22 be equipped with the torque meter disclosed with reference to FIG. 19 which for example could be adapted to stop the driving member 21 and/or operating device 23 when the bone contacting organ 22 penetrates the pelvic bone such that no further damage is made to the area of the hip joint.

Figure 19:
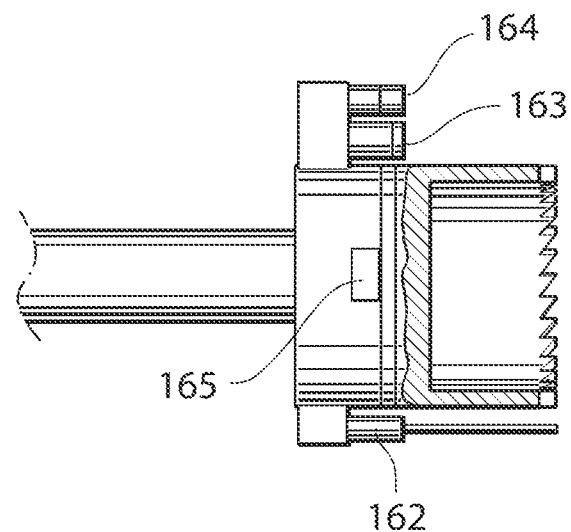
FIG. 19 shows an instrument according to an eleventh embodiment.

FIG. 19 shows an instrument according to an eleventh embodiment wherein said instrument further comprises at least one of: at least one camera 163, at least one light source 164, at least one measurement device 162 for measuring the depth of said hole in the pelvic bone and/or at least one torque meter 165 for sensing the torque exerted on the driving member 30 from the connection with the bone contacting organ 22 and the operating device 23.

Figure 20:
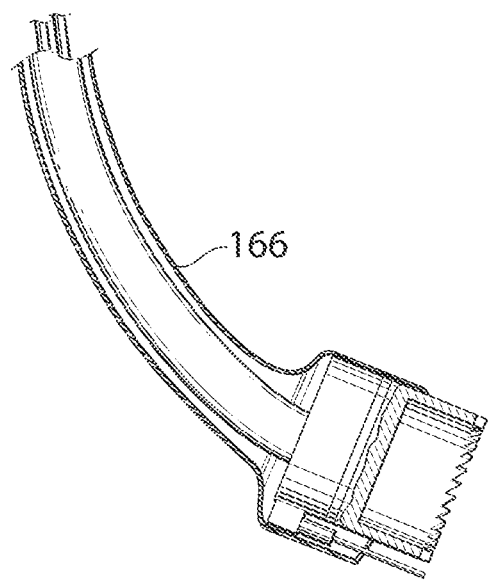
FIG. 20 shows an instrument according to a twelfth embodiment.

FIG. 20 shows an instrument according to a twelfth embodiment in which the part of said instrument adapted to be inserted in the human body is covered with a housing 166 for protecting the human body from the parts of the surgical instrument. The housing 166 could be made of a stiff or flexible material and could have an antibacterial surface.

According to a thirteenth embodiment the bone contacting organ of any of the embodiments could be changed to a bone contacting organ adapted to ream the acetabulum and/or the caput femur.

Figure 21:
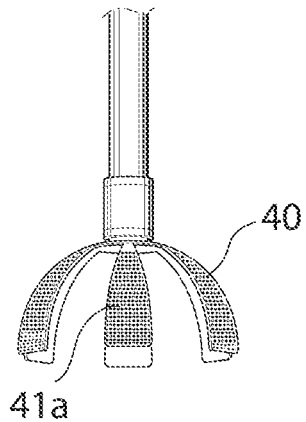
FIG. 21 shows a reamer according to a first embodiment.

FIG. 21 shows an instrument according to an embodiment wherein a reamer is adapted to ream the acetabulum 8 or the caput femur 5. The reamer could be adapted to be expandable. The expandable reamer comprises at least one reaming blade 40 which comprises a reaming surface 41a,b. Said expandable reamer could be adapted to ream the acetabulum 8, the caput femur 5 or both. In the embodiment where said expandable reamer is adapted to ream the acetabulum 8 said reaming surface 41a is located on the exterior part of the at least one reaming blade 40, whereas in the embodiment when said expandable reamer is adapted to ream the caput femur 5, said reaming surface 41b is located on the interior part of the at least one reaming blade 40. According to a second embodiment said expandable reamer is adapted to ream both the acetabulum and the caput femur, in which case the reamer has reaming surfaces 41a,b both on the exterior and the interior part of the at least one reaming blade 40.

Figure 22:
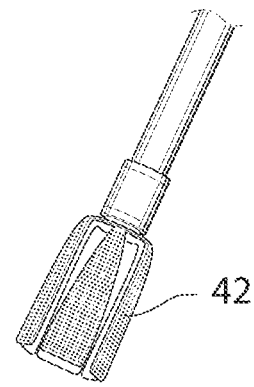
FIG. 22 shows an expandable reamer, according to any of the embodiments.

FIG. 22 shows the expandable reamer, according to any of the embodiments, wherein the reaming blades 40 can be folded towards a center of the semi-sphere that the expandable reamer produces in its expanded state, shown in FIG. 21. The folding of the reaming blades 40 enables the expandable reamer to be introduced into a hip joint through a hole smaller than the area possible to ream using said expandable reamer.

Figure 23:
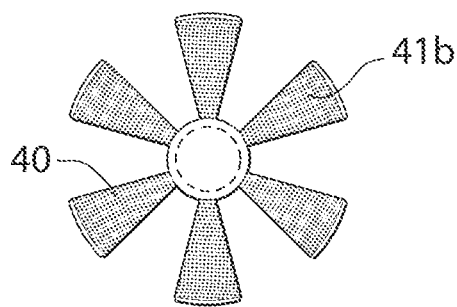
FIG. 23 shows the interior side of the expandable reamer.

FIG. 23 shows the interior side of the expandable reamer with the reaming blades 40. In the embodiment when the expandable reamer is adapted to ream the caput femur said interior side of the at least one reaming blade 40 comprises a reaming surface 41b.

Figure 24:
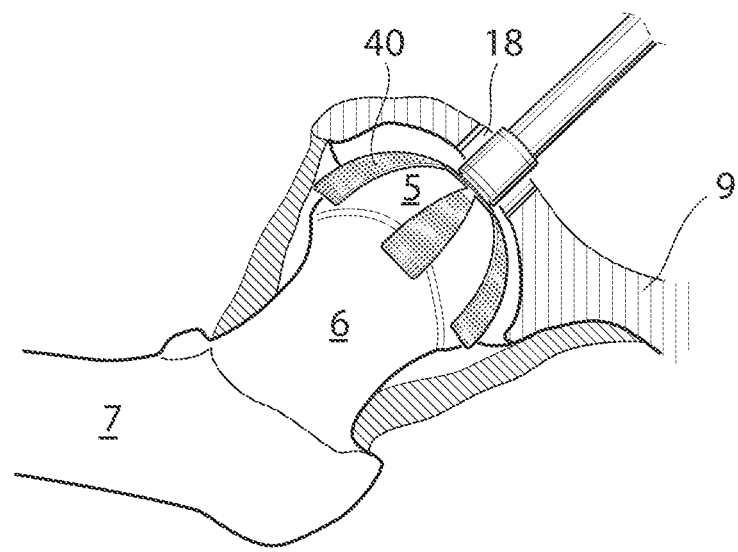
FIG. 24 shows the expandable reamer according to any of the embodiments when reaming the acetabulum and/or the caput femur.

FIG. 24 shows the expandable reamer according to any of the embodiments when reaming the acetabulum 8 and/or the caput femur 5 through the hole 18 in the pelvic bone 9. The reamer can be adapted to be operated manually or by means of a rotating, vibrating or oscillating operating device.

Figure 25A:
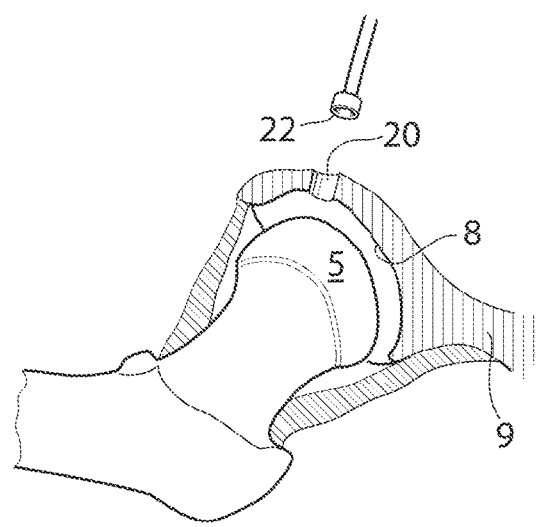
FIG. 25a shows an instrument according to a fourteenth embodiment.

FIG. 25a shows an instrument according to a fourteenth embodiment in which the instrument is adapted to make a small hole 20 in the pelvic bone 9. A small hole could be used on its own or in combination with a larger hole 18, in which case it is conceivable that the small hole is used to provide a camera to the hip joint.

When the hole in the pelvic bone is created at least one hip joint surface is provided to the hip joint, through the hole in the pelvic bone 18.

Figure 25B:
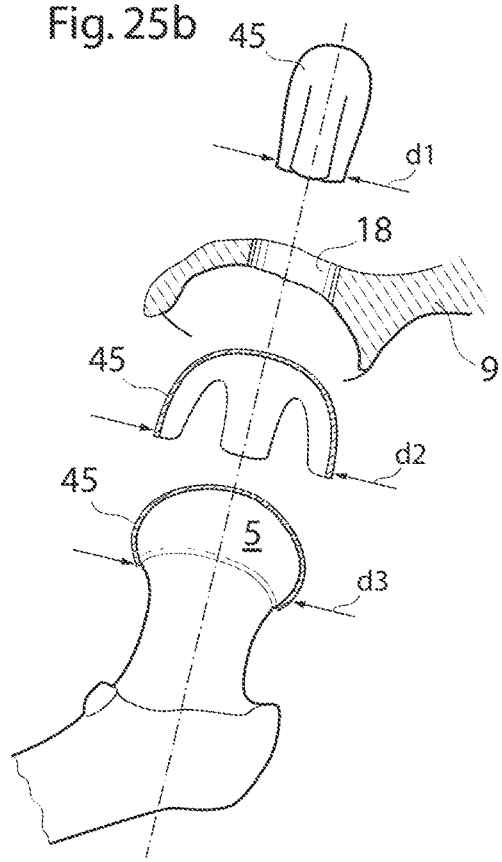
FIG. 25b shows a hip joint in section when an artificial caput femur surface is provided.

FIG. 25b shows the hip joint in section when an artificial caput femur surface 45 is provided. Said artificial caput femur surface 45 having a first distance d1 adapted to enable said artificial caput femur surface 45 to be provided through a hole 18 in the pelvic bone 9. After the insertion through a hole in the pelvic bone said distance is expanded to a second distance d2 to enable the artificial caput femur surface 45 to be able to pass over the caput femur 5. When the artificial caput femur surface 45 has passed over the caput femur 5 it is securely placed on caput femur 5 and said distance is contracted to a distance d3 smaller than the maximum cross sectional distance of the caput femur 5. This enables the artificial caput femur surface 45 to be fixedly attached to the caput femur 5 by means of its mechanical shape.

Figure 26A:
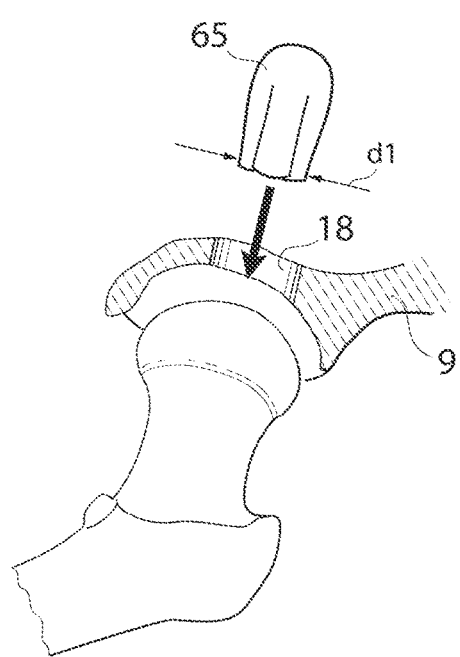
FIG. 26a shows the placing of an artificial acetabulum surface in the acetabulum bowl.

FIG. 26a shows the placing of an artificial acetabulum surface 65 in the acetabulum bowl of a human patient. Said artificial acetabulum surface 65 is introduced into the hip joint through a hole in the pelvic bone 9 in its folded state with a first distance d1.

Figure 26B:
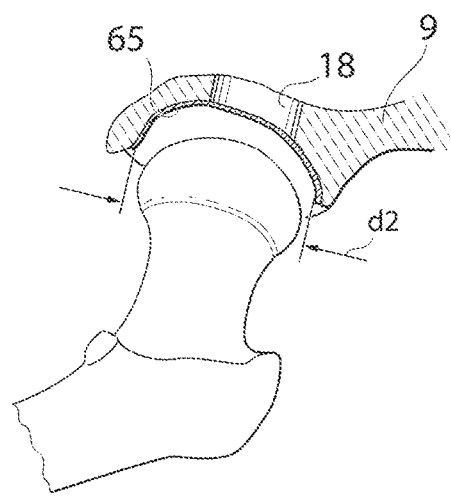
FIG. 26b shows the hip joint in section when the artificial acetabulum surface has been provided.

FIG. 26b shows the artificial acetabulum surface 65 in its expanded state having a second distance d2, hindering said artificial acetabulum surface 65 from passing through said hole 18 in the pelvic bone 9.

FIG. 27 shows an artificial caput femur surface 45 in section having a greatest cross-sectional distance 52 adapted to travel over and beyond the maximum diameter of the caput femur 5. The maximum diameter of the caput femur 5 being positioned at a corresponding largest cross sectional distance 61 of the artificial caput femur surface A second distance 62 is the distance that the artificial caput femur surface 45 travels beyond the maximum diameter of the caput femur 5. Said distance 62 is the beyond part of the artificial caput femur surface and is a part of the mechanical fixation of the artificial caput femur surface 45 to the caput femur 5.

FIG. 28a shows an artificial caput femur surface according to a first embodiment, the artificial caput femur surface 45 is adapted to pass beyond the maximum diameter of the caput femur 5. This enables a mechanical fixation using the form of said artificial caput femur surface 45. In this embodiment the artificial caput femur surface 45 comprises at least two slits 49 adapted to make said artificial caput femur surface 45 flexible for traveling over and beyond the maximum diameter of the caput femur 5. The construction could further be made flexible so that the size of the artificial caput femur surface 45 can vary to become smaller for insertion through a hole 18 in the pelvic bone 9 smaller than the full functional size of the artificial caput femur surface 45. It is also conceivable that the artificial caput femur surface 45 comprises two or more artificial caput femur surface arms 50 which have a cross sectional distance 52 between each other. This cross sectional distance 52 is according to one embodiment shorter than the maximum diameter of the caput femur 5 enabling the mechanical fixation of the artificial caput femur surface 45 by means of said artificial caput femur surface arms 50. For further fixation a band, cord or wire 59 can be placed around the artificial caput femur surface 45 beyond the maximum diameter of the caput femur 5. The band, cord or wire can be mechanically connected using a self locking member 60 for forming a ring-shaped element able to assist in the fixation of the artificial caput femur surface 45 to the caput femur 5.

FIG. 28b shows the artificial caput femur surface 45 when fixated to the caput femur with the supporting band, cord or wire placed around the artificial caput femur surface 45 beyond the maximum diameter of the caput femur 5.

Figure 29:
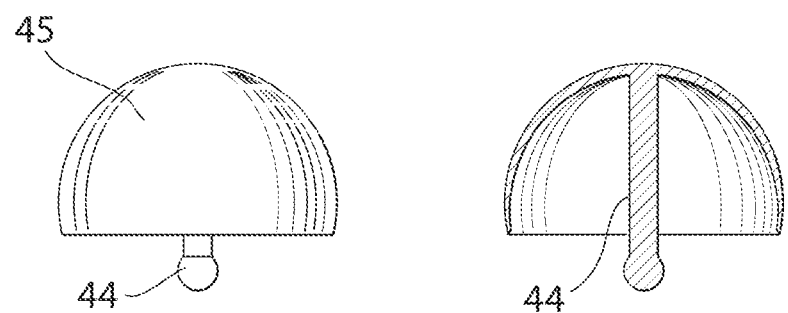
FIG. 29 shows an artificial caput femur surface 45 according to a second embodiment.

FIG. 29 shows an artificial caput femur surface 45 according to a second embodiment. The shaft or screw placed in the middle of the artificial caput femur surface 45 serves as a mechanical attachment 44 penetrating the cortex of the caput femur 5 and fixating the artificial caput femur surface 45 to the caput femur 5. However it is also conceivable that said shaft or screw is assisted or replaced with screws, welding, sprints, band, adhesive or some other mechanical connecting member.

Figure 30:
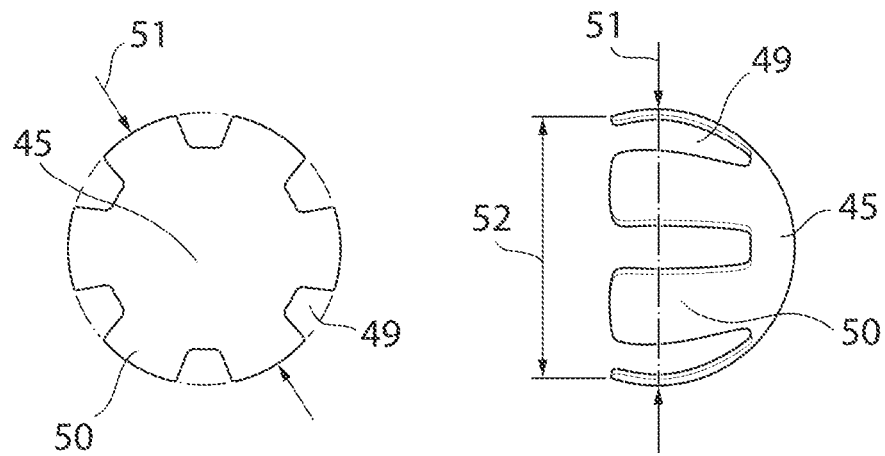
FIG. 30 shows an artificial caput femur surface 45 according to a third embodiment, FIG. 31a,b,c,d,e shows an artificial caput femur surface 45 according to a fourth embodiment.

FIG. 30 shows an artificial caput femur surface 45 according to a third embodiment, in which said artificial caput femur surface 45 comprises at least one slit 49 enabling the construction of the artificial caput femur surface 45 to be flexible, thus enabling the largest diameter 51 to vary for insertion of said artificial caput femur surface 45 through a hole in the pelvic bone 9 smaller than the full functional size of said artificial caput femur surface 45. According to this embodiment the artificial caput femur surface 45 further comprises artificial caput femur surface arms 50 located on the sides of said at least one slit 49. The caput femur surface arms 50 can be made of a flexible material enabling the insertion through a hole 18 in the pelvic bone 9 smaller than the largest diameter 51 of said artificial caput femur surface 45 when in its full functional size.

According to one embodiment the artificial caput femur surface 45 could be adapted to pass beyond the maximum diameter of the caput femur 5. This enables a mechanical fixation using the form of said artificial caput femur surface 45. In the embodiment where the artificial caput femur surface 45 travels beyond the maximum diameter of the caput femur 5 the construction can be made flexible so that the size of the artificial caput femur surface 45 can vary to become smaller for insertion through a hole 18 in the pelvic bone smaller than the full functional size of the artificial caput femur surface 45, and have an opening adapter to travel over the caput femur 5 that can be larger that the same opening is in the full functional size of the artificial caput femur surface 45 enabling the artificial caput femur surface 45 to at least partly cover an area beyond the maximum diameter of caput femur 5 from the direction of the acetabulum 8. According to another embodiment the artificial caput femur surface 45 comprises two or more artificial caput femur surface arms 50 which have a cross sectional distance 52 between each other. This cross sectional distance 52 is according to one embodiment shorter than the maximum diameter of the caput femur 5 enabling the mechanical fixation of the artificial caput femur surface 45 by means of said artificial caput femur surface arms 50.

FIGS. 31a,b,c,d,e show an artificial caput femur surface 45 according to a fourth embodiment, in which said artificial caput femur surface 45 comprises a first 53a and a second 53b section, as shown in FIG. 31b. The first and second sections are displaceable in relation to each other. According to a first embodiment said first section 53a can be rotated in relation to said second section 53b so that said second section 53b travels underneath said first section 53a to create a displaced artificial caput femur surface 54, as shown in FIG. 31c, which is possible to insert into a hip joint of a human patient through a hole 18 being oval, or at least having an area smaller than the cross sectional area of the artificial caput femur surface 45 when in its full functional size 45, as shown in FIG. 31a. According to this embodiment the two sections are connected to each other when the artificial caput femur surface 45 is returned to its full functional size using a mechanical form fitting 55, as shown in FIG. 31e. However it is also conceivable that said connection is assisted or replaced with screws, welding, sprints, band, adhesive or some other mechanical connecting member.

FIGS. 32a,b shows the artificial caput femur surface 45 according to a fifth embodiment, in which said artificial caput femur surface 45 comprises four slits. The artificial caput femur surface 45 is flexible in its construction allowing the four artificial caput femur arms 50 to be folded towards the center axis of the artificial caput femur surface 45 thus allowing the artificial caput femur surface 45 to be inserted into a hip joint through a hole smaller than the full functional size of the artificial caput femur surface 45. The artificial caput femur surface 45 according to this embodiment can be constructed to go beyond the maximum diameter of the caput femur 5, in which case the construction with the slits 49 allows the artificial caput femur surface 45 to change to both a smaller and a larger size than said full functional size.

FIG. 32b shows the artificial caput femur surface 45 in section when said artificial caput femur surface arms 50 are folded for insertion through a hole 18 with an area smaller than the largest area of the artificial caput femur surface 45 when in its full functional size.

FIG. 33a shows the artificial caput femur surface 45 according to a sixth embodiment, in which said artificial caput femur surface 45 comprises multiple ring-shaped artificial caput femur surface parts 63. Said multiple ring-shaped artificial caput femur surface parts 63 are adapted to be connected to each other to form an artificial caput femur surface 45, shown in FIG. 33b. According to one embodiment said artificial caput femur surface parts 63 are adapted to be connected to each other using mechanical connecting members 64a,b. In FIG. 33c, 64a shows how an individual ring-shaped artificial caput femur surface part 63 can be connected to itself to form a continuous ring shape. 64b shows how an individual ring-shaped artificial caput femur surface part 63 connects to other ring-shaped artificial caput femur surface parts 63 to form an artificial caput femur surface 45. The artificial caput femur surface 45 according to this embodiment can further be adapted to go beyond the maximum diameter of the caput femur 5.

FIG. 34a,b,c shows the artificial caput femur surface 45 according to a sixth embodiment, in which said artificial caput femur surface 45 comprises multiple artificial caput femur surface parts 46. Said multiple artificial caput femur surface parts 46 are adapted to be connected to an interconnecting artificial caput femur surface part 56 after insertion into a hip joint. The interconnecting artificial caput femur surface part 56 comprises self locking connecting members 57, shown in FIG. 34b, that fits with corresponding self locking members 58 of the artificial caput femur surface parts 46. The artificial caput femur surface parts 46 creates an artificial caput femur surface 45 when connected to each other, shown in FIG. 11c. The self locking members 57,58 can be assisted or replaced with screws, welding, sprints, band, adhesive or some other mechanical connecting member. The artificial caput femur surface 45 according to this embodiment can further be adapted to go beyond the maximum diameter of the caput femur 5.

Figure 35:
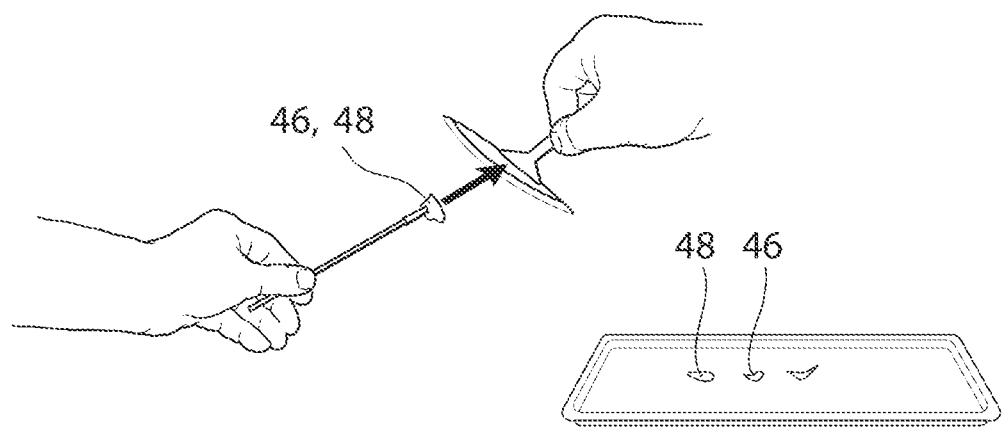
FIG. 35 shows an artificial hip joint surface part, according to any of the embodiments, being inserted through an incision according to a surgical method.

FIG. 35 shows the artificial hip joint surface parts 48 according to any of the embodiments being inserted through an incision according to a surgical method. According to a first embodiment the artificial hip joint surface parts 48 are artificial caput femur surface parts 46, adapted to be connected to each other after the insertion to form an artificial caput femur surface 45.

Figure 36:
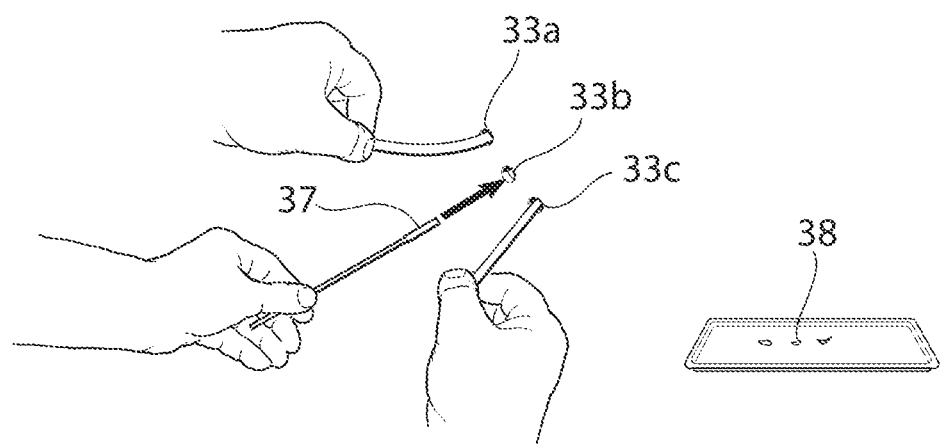
FIG. 36 shows an artificial hip joint surface part, according to any of the embodiments, being inserted through an incision according to a laparoscopic/arthroscopic method.

FIG. 36 shows the artificial hip joint surface parts 48 according to any of the embodiments being inserted through laparoscopic/arthroscopic trocars 33a,b,c, through a small incision according to a laparoscopic/arthroscopic method. According to a first embodiment the artificial hip joint surface parts 48 are artificial caput femur surface parts 46, adapted to be connected to each other after the insertion to form an artificial caput femur surface 45.

A surgical and laparoscopic/arthroscopic method of treating hip joint osteoarthritis by providing a hip joint surface through the pelvic bone of a human patient from the opposite side from acetabulum is further provided. Said method will now be described in further detail.

Figure 37:
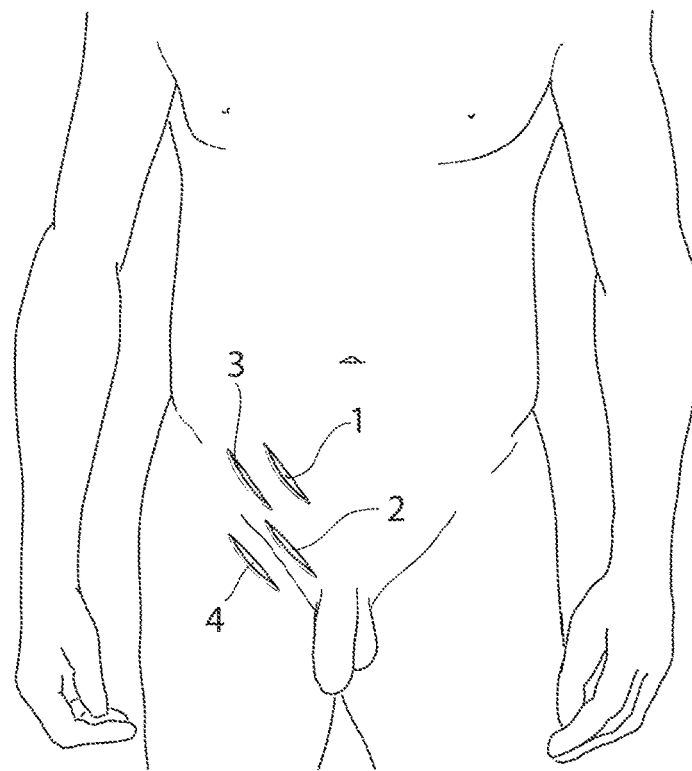
FIG. 37 shows a frontal view of the body of a human patient.

FIG. 37 shows a frontal view of the body of a human patient. A surgical method of operating the hip joint from the opposite side from acetabulum, is according to a first embodiment performed starting with an incision 1 in the abdominal wall of the human patient. The incision 1 passes through the rectus abdominis and peritoneum in to the abdomen of the human patent. In a second preferred embodiment the incision 2 is conducted through the rectus abdominis and in to the pelvic area, below peritoneum. According to a third embodiment the incision 3 is performed just between Illium and the surrounding tissue, an incision 3 which could enable the pelvic bone to be dissected with very little penetration of fascia and muscular tissue. According to a fourth embodiment the incision 4 is made in the inguinal channel. In all of the four embodiments the tissue surrounding the pelvic bone 9 in the area opposite to acetabulum is removed or penetrated which enables the surgeon to reach the pelvic bone 9.

Figure 38:
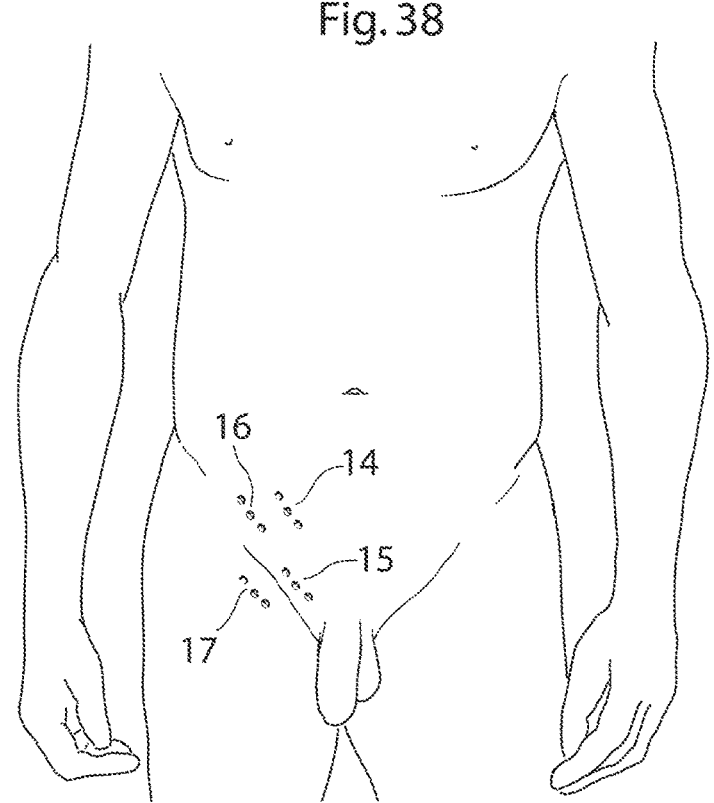
FIG. 38 shows a frontal view of the body of a human patient.

FIG. 38 shows a frontal view of the body of a human patient. A laparoscopic/arthroscopic method of operating the hip joint, from the opposite side from acetabulum, is according to a first embodiment performed starting with making small incisions 14 in the abdominal wall of the human patient. The small incisions enable the surgeon to insert laparoscopic/arthroscopic trocars into the abdomen of the human patient. According to the first embodiment the incisions 14 passes through the rectus abdominis and peritoneum in to the abdomen of the human patent. According to a second preferred embodiment the small incisions 15 is conducted through the rectus abdominis and in to the pelvic area, below peritoneum. According to a third embodiment the small incisions 16 is performed just between Illium and the surrounding tissue, an incision 16 which could enable the pelvic bone to be dissected with very little penetration of fascia and muscular tissue. According to a fourth embodiment the incision 17 is made in the inguinal channel. In all of the four embodiments the tissue surrounding the pelvic bone 9 in the area opposite to acetabulum 8 is removed or penetrated which enables the surgeon to reach the pelvic bone 9.

Figure 39:
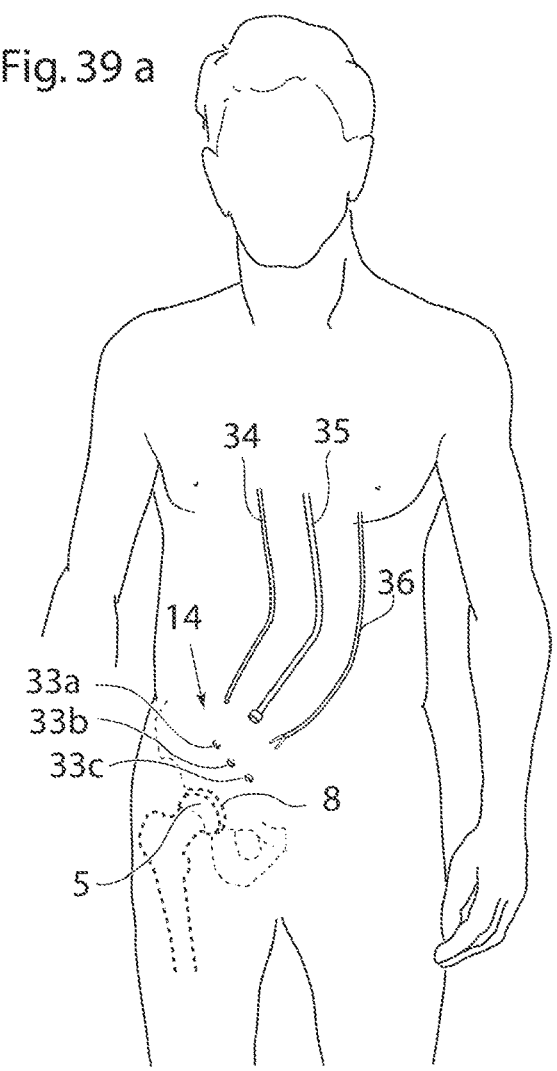
FIG. 39a shows a frontal view of the body of a human patient.
FIG. 39b shows a lateral view of the body of a human patient in section.
Figure 39:
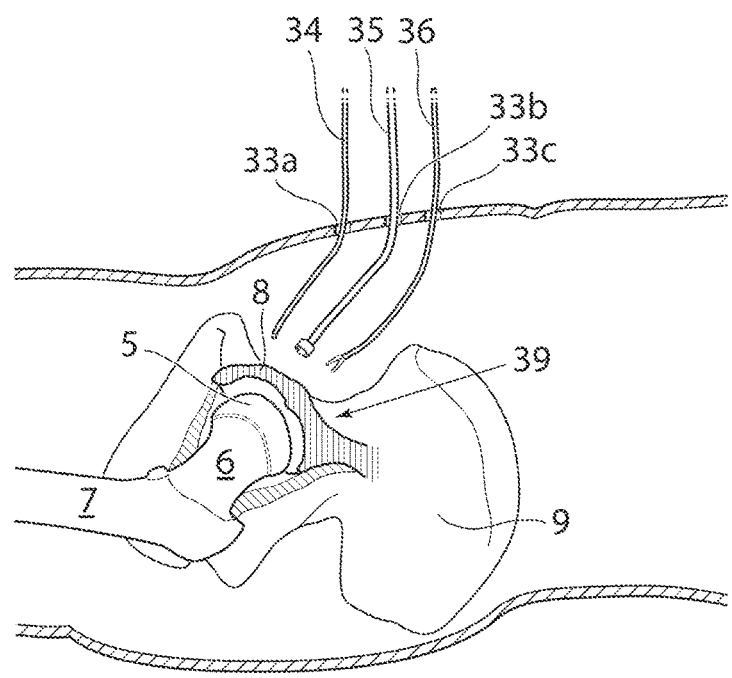

FIG. 39*a* shows a frontal view of the body of a human patient, illustrating the laparoscopic/arthroscopic method of operating the hip joint from the opposite side from acetabulum 8. The hip joint comprising the acetabulum 8 and the caput femur 5. The small incisions 14 in the abdominal wall of the human patient allows the insertion of laparoscopic/arthroscopic trocars 33*a,b,c* into the body of the patients. Whereafter one or more camera 34, a surgical instrument adapted to create a hole in the pelvic bone 35, or instruments 36 for introducing, placing, connecting, attaching, creating or filling prosthesis or prosthetic parts, can be inserted into said body through said laparoscopic/arthroscopic trocars 33*a,b,c*.

FIG. 39*b* shows a lateral view of the body of a human patient, with the hip joint shown in section in further detail. The hip joint comprises a caput femur 5 placed at the very top of collum femur 6 which is the top part of the femur bone 7. The caput femur is in connection with the acetabulum 8 which is a bowl shaped part of the pelvic bone 9.

Laparoscopic/arthroscopic trocars 33*a,b,c* is being used to reach the hip joint 39 with one or more camera 34, a surgical instrument adapted to create a hole in the pelvic bone 35, or instruments 36 for introducing, placing, connecting, attaching, creating or filling prosthesis or prosthetic parts.

Figure 40:
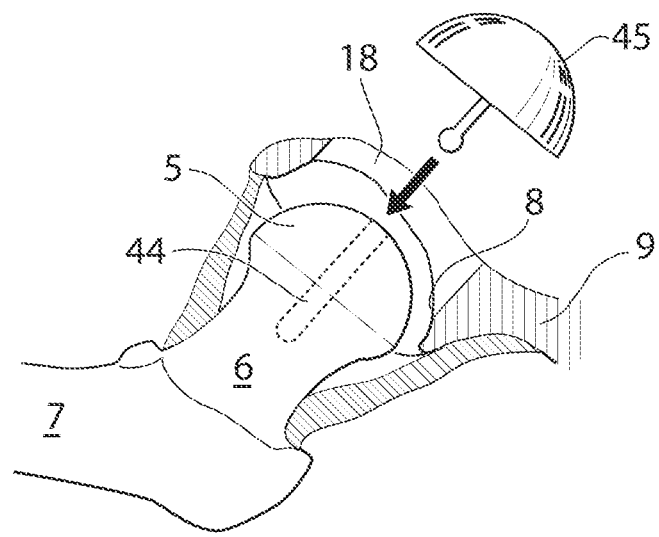
FIG. 40a shows the step of providing an artificial caput femur surface.
FIG. 40b shows the a section of a hip joint after the artificial caput femur surface has been provided.
Figure 40:
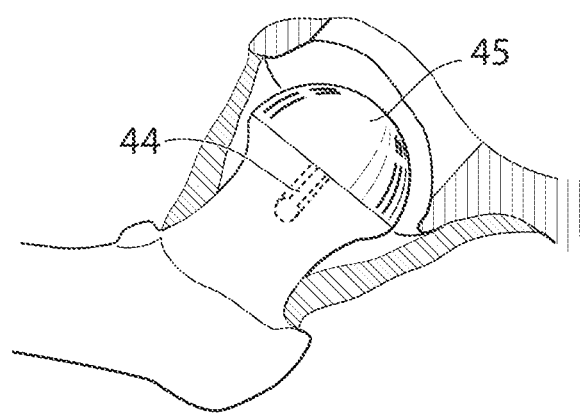

FIG. 40*a,b* shows the hip joint in section with the caput femur 5 placed at the very top of collum femur 6 which is the top part of the femur bone 7. The caput femur is in connection with the acetabulum 8 which is a bowl shaped part of the pelvic bone 9. According to a first embodiment the hole 18 created in the pelvic bone 9 from the opposite side from acetabulum 8, is larger than said artificial caput femur surface 45, enabling the insertion of said artificial caput femur surface 45 in its full functional size. Said insertion of said artificial caput femur surface 45 could be performed as a step of the surgical method, as well as a step of the laparoscopic/arthroscopic method. After the insertion, the artificial caput femur surface 45 is attached to the caput femur 5, the attaching is performed by means of a mechanical attachment 44 comprising a shaft or screw penetrating the cortex. It is however also conceivable that the mechanical attachment 44 is assisted or replaced by bone cement or adhesive placed between caput femur 5 and the artificial caput femur surface 45, or in connection with said shaft or screw 44. Alternative ways of attaching the artificial caput femur surface 45 includes: form fitting, welding, sprints, band or some other mechanical connecting member.

FIG. 40*b* shows the hip joint in section with the artificial caput femur surface 43 attached to the caput femur 5.

Figure 41:
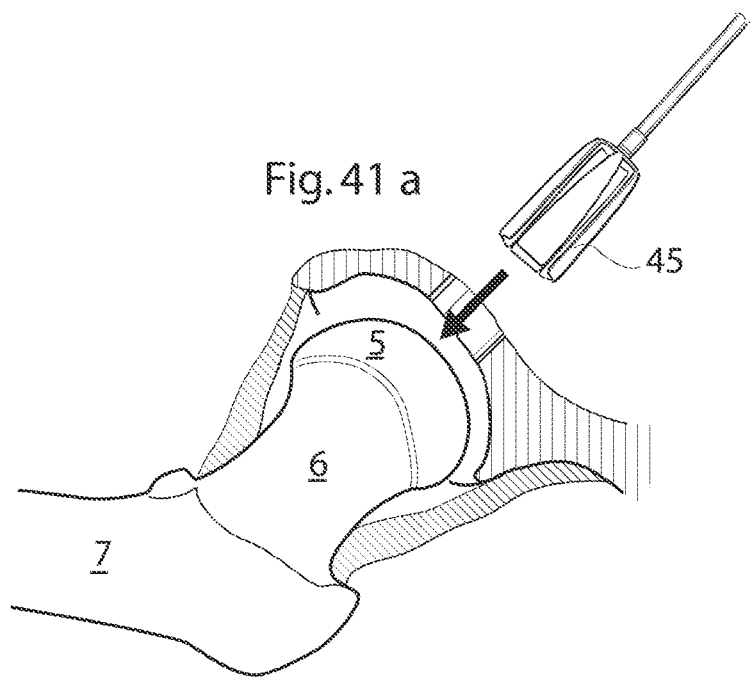
FIG. 41a shows an expandable artificial caput femur surface, according to the second embodiment, when traveling through a hole in the pelvic bone.
FIG. 41b shows an expandable artificial caput femur surface, according to the second embodiment, when being placed on the caput femur.
FIG. 41c shows an expandable artificial caput femur surface, according to the second embodiment, when placed on the caput femur.
Figure 41:
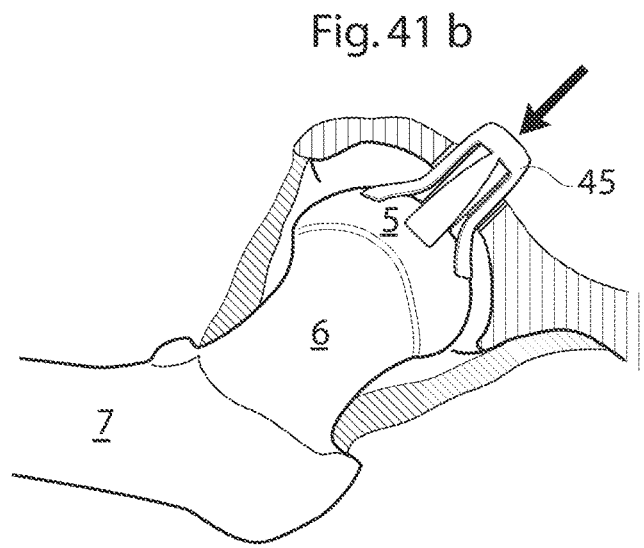
Figure 41:
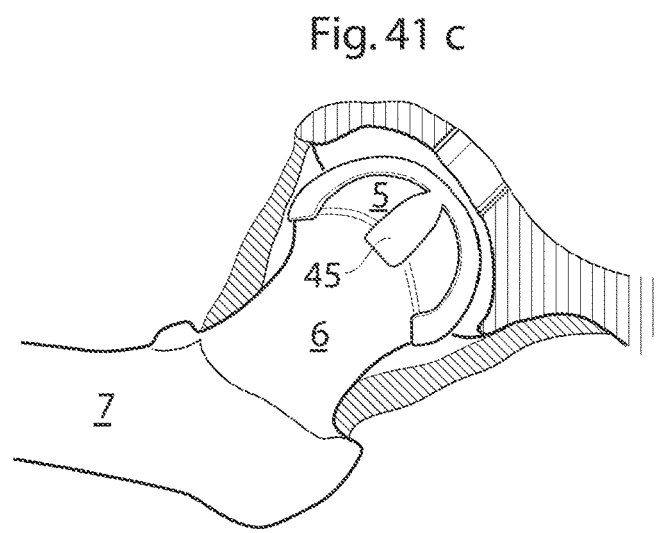

FIG. 41*a* shows how an expandable artificial caput femur surface 45 is being inserted through a hole 18 in the pelvic bone 9.

FIG. 41*b* shows how an expandable artificial caput femur surface 45 goes through the hole 18 in the pelvic bone 9 and travels over caput femur 5.

FIG. 41*c* shows an expandable artificial caput femur surface 45 is after it has been placed on the caput femur 5.

Figure 42:
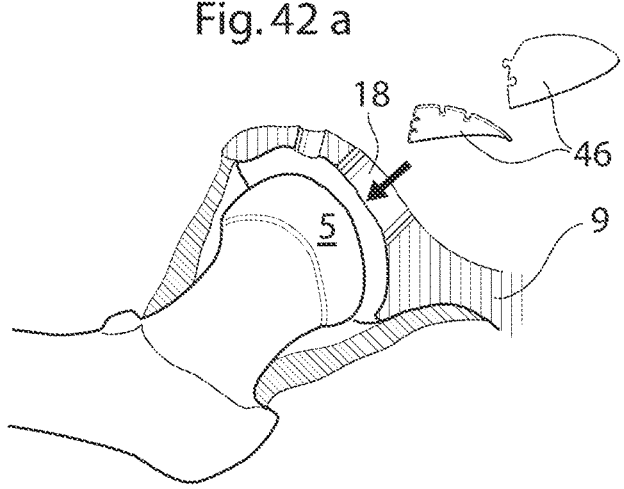
FIG. 42a show the insertion of artificial caput femur surface parts into the hip joint.
FIG. 42b shows the artificial caput femur surface parts after they have been connected inside of the hip joint forming an artificial caput femur surface.
FIG. 42c shows how the form of the artificial caput femur surface parts enables the connection of the artificial caput femur surface parts to form an artificial caput femur surface.
FIG. 42d shows a camera being inserted into the hip joint.
Figure 42:
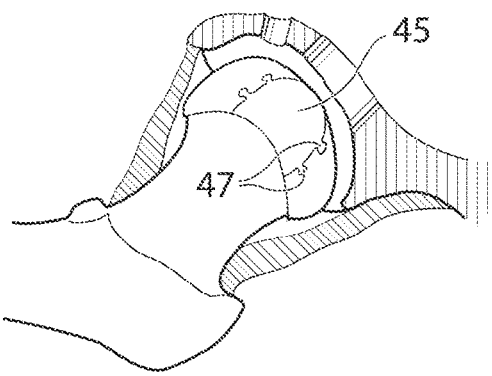
Figure 42:
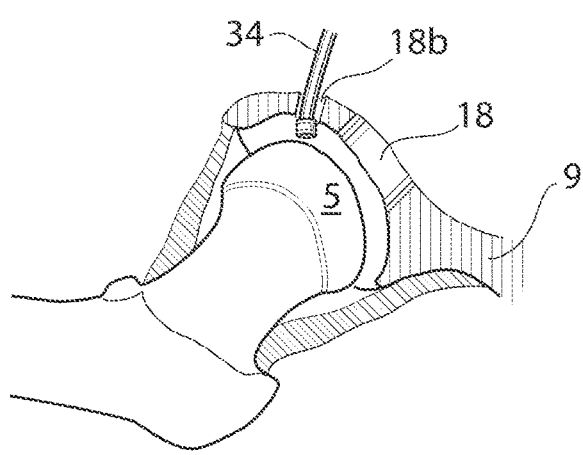
Figure 42:
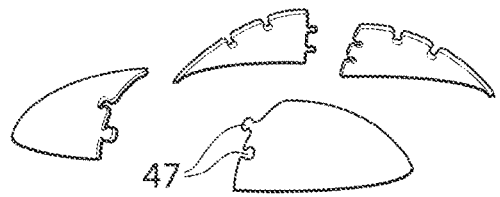

FIG. 42*a* shows the hip joint in section according to a second embodiment in which the hole 18 in the pelvic bone 9 is smaller than the artificial caput femur surface 45 in its full functional size. According to this embodiment the artificial caput femur surface 45 is introduced into the hip joint through the hole 18 in the pelvic bone 9 form the opposite side from acetabulum 8. The artificial caput femur surface parts 46 are connected to each other after insertion into the hip joint to form the artificial caput femur surface 45.

FIG. 42*b* shows the hip joint in section when the artificial caput femur surface parts 46 are connected to each other using form fitting 47, however it is conceivable that the form fitting is assisted or replaced with adhesive or bone cement. After the artificial caput femur surface parts 46 have been introduced and connected in the hip joint, they are mechanically fixated to the caput femur 5, the mechanical fixation could be done by means of screws, form fitting, welding, sprints, band, adhesive or some other mechanical attachment member.

FIG. 42*c* shows the artificial caput femur surface parts 46 with the parts supplying the form fitting 47.

FIG. 42*d* shows the hip joint in section wherein a second hole 18*b* in the pelvic bone 9 enables the surgeon to place a camera 34 into the hip joint, preferably used in the laparoscopic/arthroscopic method.

After the step of providing an artificial caput femur surface the surgical and laparoscopic/arthroscopic methods could further comprises the step of providing an artificial acetabulum surface.

According to a first embodiment the artificial acetabulum surface 65 is provided through a hole 18 in the pelvic bone 9 from the opposite side from acetabulum 8.

Figure 43:
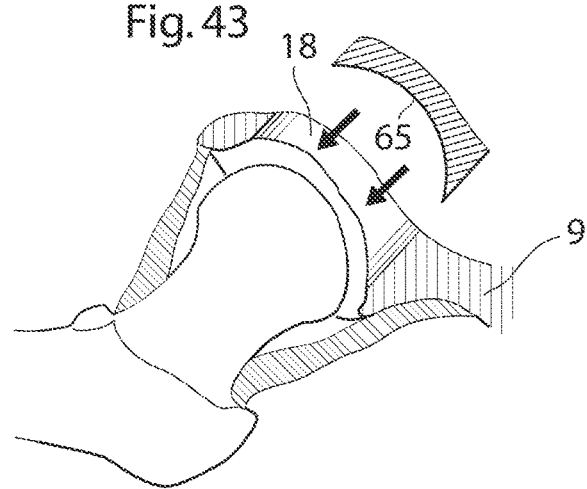
FIG. 43 shows an artificial acetabulum surface when being inserted into a hip joint.

FIG. 43 shows an artificial acetabulum surface 65 in its full functional size as it is being inserted through a hole 18 in the pelvic bone 9.

FIG. 44 shows an artificial acetabulum surface 65 according to a second embodiment in which the artificial acetabulum surface 65 comprises at least one slit 66 enabling the artificial acetabulum surface 65 to vary in size for insertion through a hole 18 in the pelvic bone 9 smaller than the full functional size of the artificial caput femur surface 45. The slits are placed between one or more artificial caput femur surface arms 67 which are flexible by means of the material or by means of a joint affecting said artificial caput femur surface arms 67.

FIG. 45*a,b,c* shows an artificial acetabulum surface 65 according to a second embodiment in which the artificial acetabulum surface 65 comprises multiple artificial acetabulum surface parts 68. Said multiple artificial acetabulum surface parts 68 are adapted to be connected to an interconnecting artificial acetabulum surface part 69 after insertion into a hip joint. The interconnecting artificial caput femur surface part 69 comprises self locking connecting members 70*a*, shown in FIG. 45*b*, that fits with corresponding self locking members 70*b* of the artificial acetabulum surface parts 68. The artificial acetabulum surface parts 68 creates an artificial acetabulum surface 65 when connected to each other, shown in FIG. 45*c*. The self locking members 70*a,b* can be assisted or replaced with screws, welding, sprints, band, adhesive or some other mechanical connecting member.

FIG. 46*a,b,c* shows an artificial acetabulum surface 65 according to a third embodiment in which the artificial acetabulum surface 65 comprises multiple ring-shaped artificial acetabulum surface parts 71. Said multiple ring-shaped artificial acetabulum surface parts 71 are adapted to be connected to each other to form an artificial acetabulum surface 65 after insertion in a hip joint. According to one embodiment said artificial acetabulum surface parts 71 are adapted to be connected to each other using mechanical connecting members 72a,b. FIG. 46c shows how an individual ring-shaped artificial acetabulum surface part 72a can be connected to itself using the mechanical connecting member 70a to form a continuous ring shape. Further 46c shows how an individual ring-shaped artificial acetabulum surface part 71 connects to other ring-shaped artificial acetabulum surface parts 71 using the mechanical connecting member 72b to form an artificial acetabulum surface 65.

FIG. 47a,b,c,d, shows an artificial acetabulum surface 65 according to a fourth embodiment in which the artificial acetabulum surface 65 comprises a first 73a and a second 73b section, shown in FIG. 47b. The first and second sections are displaceable in relation to each other. According to a first embodiment said first section 73a can be rotated in relation to said second section 73b so that said second section 73b travels underneath said first section 73a to create a displaced artificial acetabulum surface 74, as shown in FIG. 47c, which is possible to insert into a hip joint of a human patient through a hole being oval, or at least having an area smaller than the cross sectional area of the artificial acetabulum surface 65 when in its full functional size 65. According to this embodiment the two sections 73a,b are connected to each other when the artificial acetabulum surface is returned to its full functional size using a mechanical form fitting 75, as shown in FIG. 47d. However it is also conceivable that said connection is assisted or replaced with screws, welding, sprints, band, adhesive or some other mechanical connecting member.

FIG. 48a shows an artificial acetabulum surface 65 according to a fifth embodiment in which the artificial acetabulum surface 65 comprises four slits 66. The artificial acetabulum surface 65 is flexible in its construction allowing the four artificial acetabulum arms 67 to be folded towards the center axis of the artificial acetabulum surface 65 thus allowing the artificial acetabulum surface to be inserted into a hip joint through a hole smaller than the full functional size of the artificial acetabulum surface 65.

FIG. 48b shows the artificial acetabulum surface 65 according to the fifth embodiment in its folded state.

Figure 49:
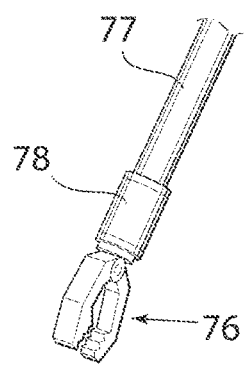
FIG. 49a shows an instrument for inserting parts into a hip joint according to a first embodiment.
FIG. 49b shows an instrument for inserting parts into a hip joint according to a second embodiment.
FIG. 49c shows an instrument for inserting parts into a hip joint according to a third embodiment.
Figure 49:
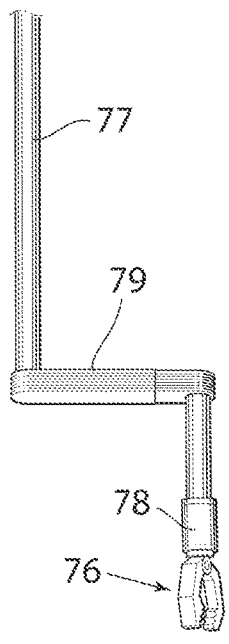
Figure 49:
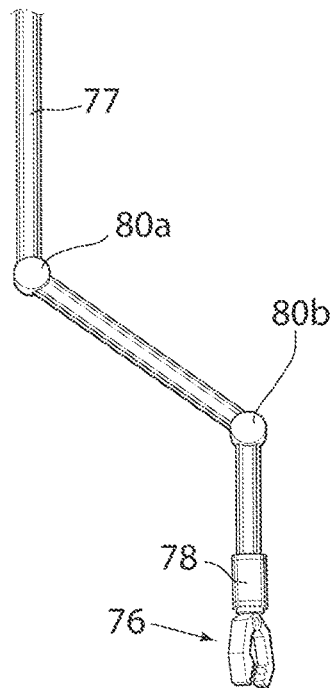

FIG. 49a shows a surgical instrument adapted to insert a prosthesis, prosthetic parts or parts needed to create or provide a hip joint surface, according to a first embodiment. The surgical instrument comprises a gripping portion 76 and a handling portion 77. According to the embodiments shown in FIG. 49a,b,c the instrument further comprises a rotation element 78 that enables the gripping part 76 to rotate in relation to the handling part 77, however it is equally conceivable that the surgical instrument lacks this rotation element 78.

FIG. 49b shows the surgical instrument adapted to insert a prosthesis, prosthetic parts or parts needed to create or provide a hip joint surface, according to a second embodiment. According to this embodiment the surgical instrument further comprises a parallel displaced section 79, which increases the reach of the instrument and facilitates the reaching of the hip joint through a hole 18 in the pelvic bone 9 from the opposite side from acetabulum.

FIG. 49c shows the surgical instrument adapted to insert a prosthesis, prosthetic parts or parts needed to create or provide a hip joint surface, according to a third embodiment. According to this embodiment the surgical instrument further comprises two angle adjusting members 80a,b. The angle adjusting members could be adjustable for varying the angle of said gripping part 76 in relation to the handling portion 77, or fixed in an angle suitable for creating operating in a hip joint through a hole in the pelvic bone from the opposite side from acetabulum 8.

Figure 50:
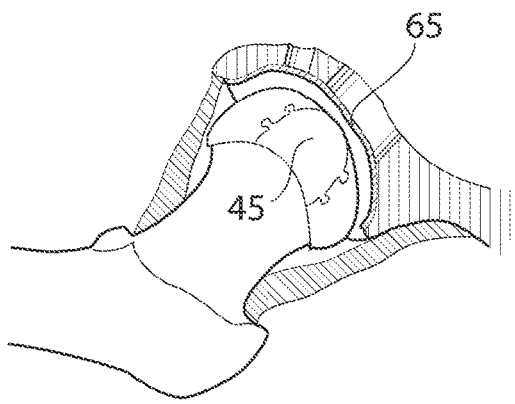
FIG. 50 shows a hip joint in section after an artificial caput femur surface and an artificial acetabulum surface has been provided.

FIG. 50 shows the hip joint in section after the artificial caput femur surface 45, and the artificial acetabulum surface 65 have been provided.

A different approach to the step of providing an artificial hip joint surface will now be described. This approach comprises the steps of casting an artificial hip joint surface inside of the hip joint. These steps can be performed by means of a mould, or without.

Figure 51:
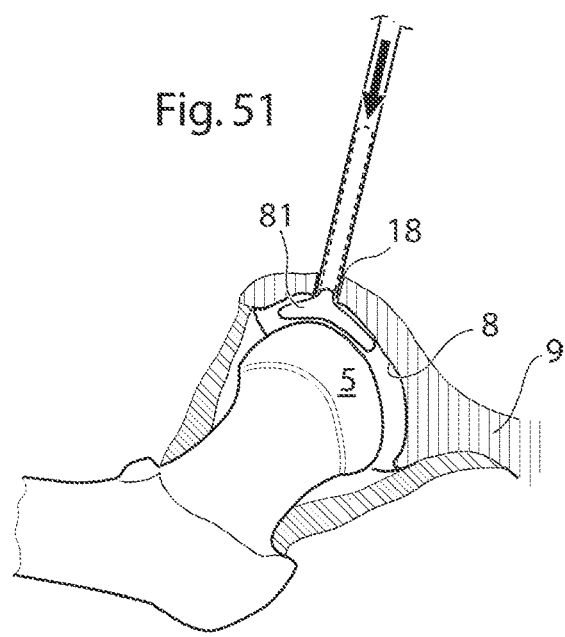
FIG. 51 shows a hip joint in section when a mould is being inserted.

FIG. 51 shows the step of placing a mould 81 inside of the hip joint of a human patient through a hole 18 in the pelvic bone 9. The step of placing said mould 81 can be performed in the surgical, or in the laparoscopic/arthroscopic method.

Figure 52:
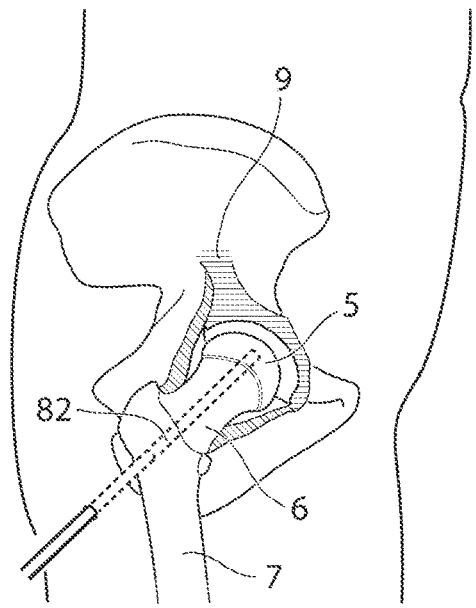
FIG. 52*a* shows the creation of a hole in the femur bone.
FIG. 52*b* shows an instrument able to introduce objects into a hip joint through the femur bone.
FIG. 52*c* shows the placing of a mould inside of the hip joint using an instrument that operates through the femur bone.
FIG. 52*d* shows a hip joint in section after the placing of a mould inside of the hip joint using an instrument that operates through the femur bone.
Figure 52:
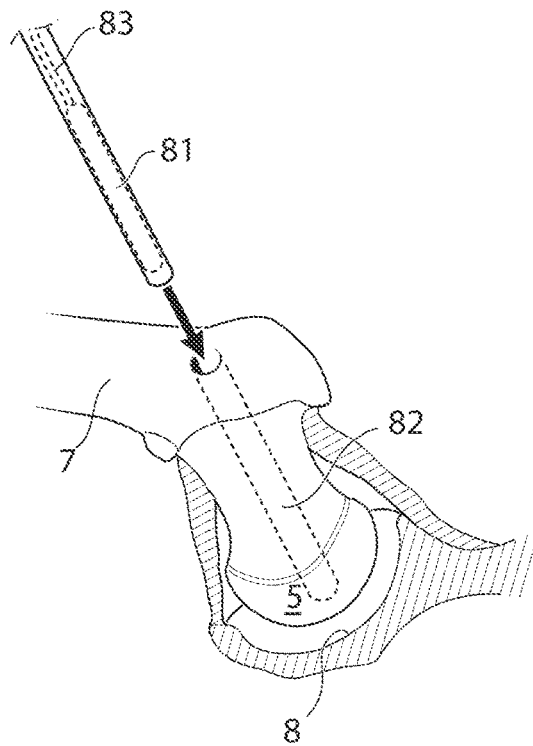
Figure 52:
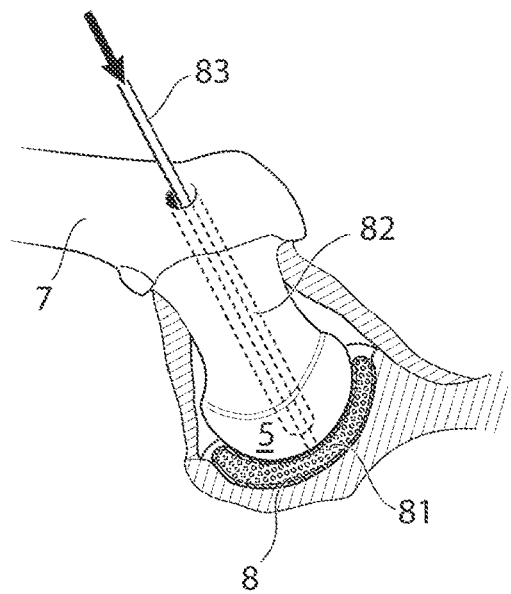
Figure 52:
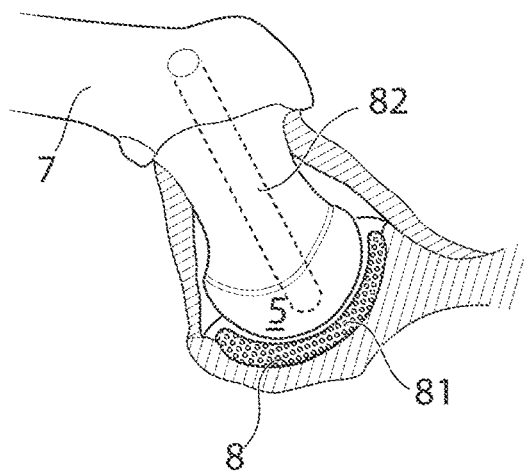

FIG. 52a,b,c,d shows an alternative approach to placing said mould 81 in the hip joint of a human patient. Said alternative approach comprises the steps of creating a hole 82 in the femur bone 7 following a length axis of the collum femur 6, said hole starting from the lateral side of the thigh, penetrating the cortex of the femur bone 7 and eventually reaching the cortex of the caput femur 5 from the inside thereof, penetrating said cortex and entering into the hip joint. After the creation of the hole 82 in the femur bone 7 the mould 81 is inserted into the hip joint through the hole 82 using a surgical instrument 83 adapted therefor, shown in FIG. 52b.

FIG. 52c shows the mould 81 when being inserted into the hip joint using the surgical instrument 83 adapted therefor.

FIG. 52d shows the mould 81 after insertion into the hip joint, the surgical instrument used to place said mould 81 in the hip joint is retracted after the insertion is completed.

It is also conceivable that the hip joint surface is provided by casting the hip joint surface inside of the hip joint without the use of a mould 81.

Figure 53:
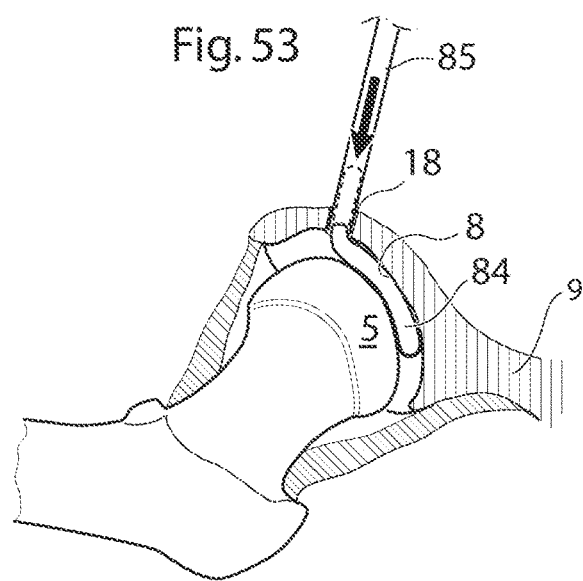
FIG. 53 shows the insertion of a first sealing member into a hip joint.

FIG. 53 shows the hip joint in section wherein a first sealing member 84 is inserted through a hole 18 in the pelvic bone 9 using an instrument adapted therefor 85. The step of placing said first sealing member 84 can be performed in the surgical, or in the laparoscopic/arthroscopic method.

Figure 54:
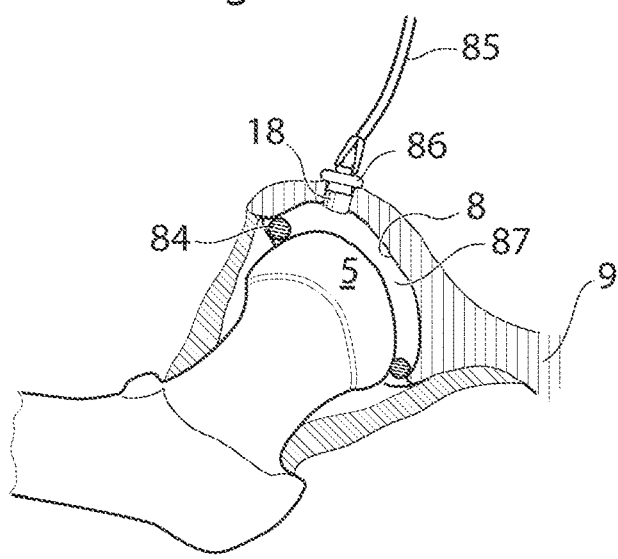
FIG. 54 shows the insertion of a second sealing member.

FIG. 54 shows the hip joint in section wherein a second sealing member 86 is inserted through the surgical or laparoscopic/arthroscopic method. The first 84 and second 86 sealing members creates a sealed space 87 between the acetabulum 8 and the caput femur 5 adapted to be used as a mould for providing an artificial acetabulum 65 and/or a caput femur surface 45.

Figure 55:
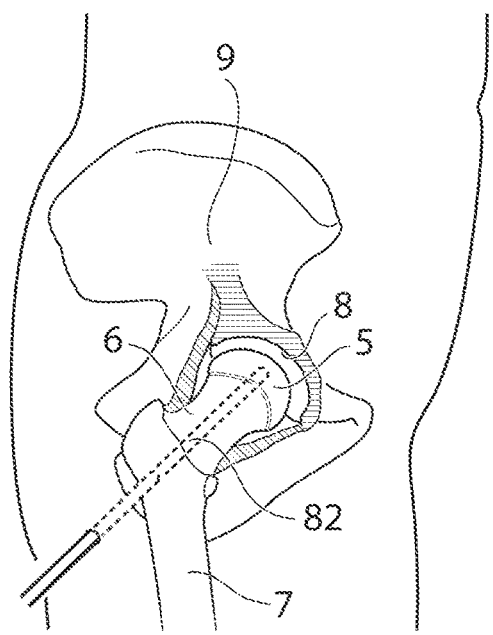
FIG. 55*a* shows the creation of a hole in the femur bone.
FIG. 55*b* shows an instrument able to introduce objects into a hip joint through the femur bone.
FIG. 55*c* shows the placing of a sealing member inside of a hip joint using an instrument that operates through the femur bone.
Figure 55:
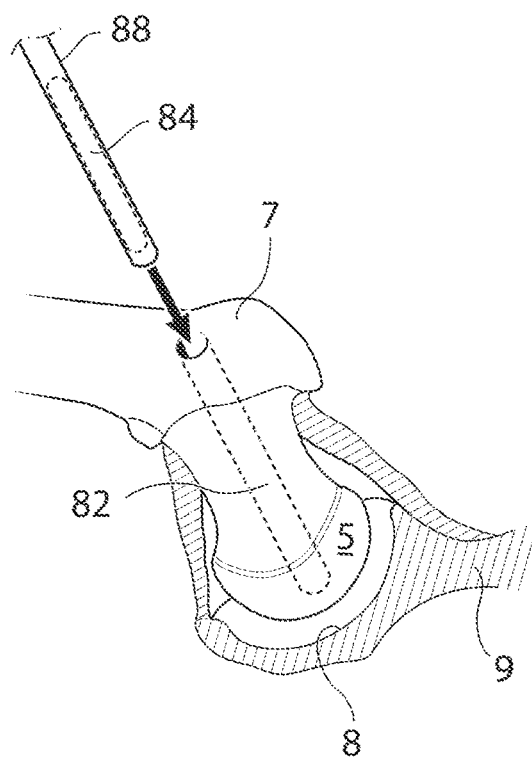
Figure 55:
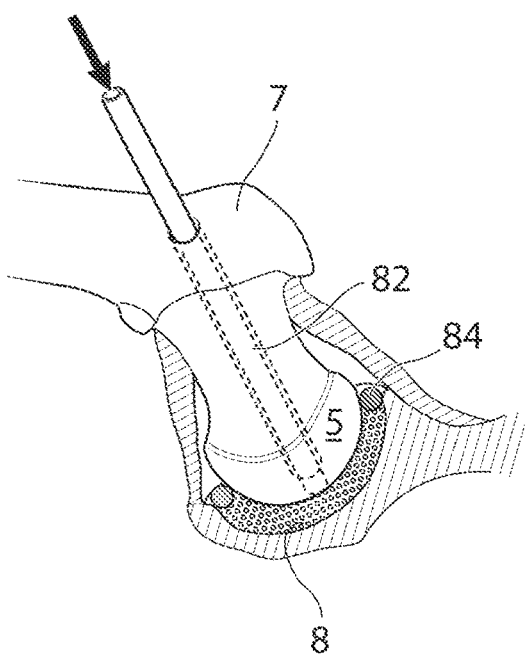

FIG. 55a,b,c shows an alternative approach to placing said first sealing member 84 in the hip joint of a human patient. Said alternative approach comprises the steps of creating a hole 82 in the femur bone 7 following a length axis of the collum femur 6, as shown in FIG. 55a, said hole starting from the lateral side of the thigh, penetrating the cortex of the femur bone 7 and eventually reaching the cortex of the caput femur 5 from the inside thereof, penetrating said cortex and entering into the hip joint. After the creation of the hole 82 in the femur bone 7 the first sealing member 84 is inserted into the hip joint through the hole 82 using a surgical instrument 88 adapted therefor, as shown in FIG. 55c.

Figure 56:
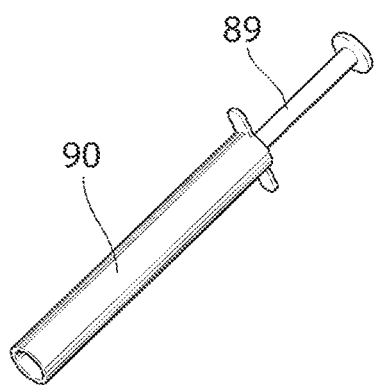
FIG. 56*a* shows an instrument for insertion of a mould or a sealing member into a hip joint.
FIG. 56*b* shows the instrument for insertion of a mould or a sealing member into a hip joint in section.
FIG. 56*c* shows an instrument for insertion of a mould or a sealing member into a hip joint according to a second embodiment.
Figure 56:
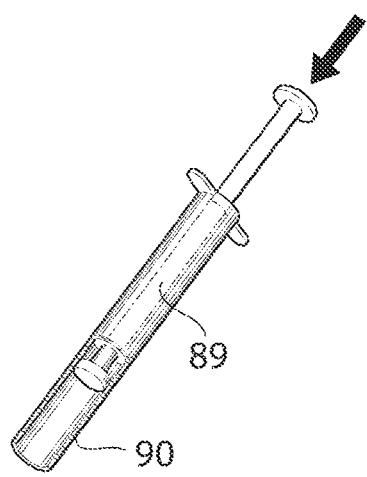
Figure 56:
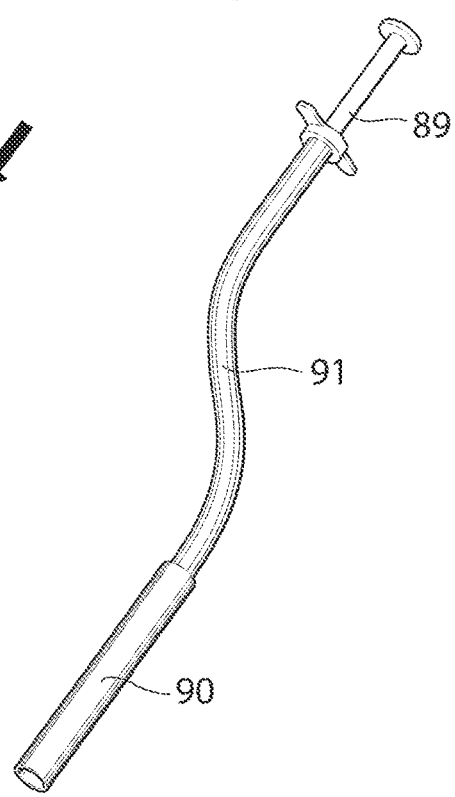

FIG. 56a,b,c shows the surgical instrument adapted to insert a mould 81 and/or a first and second sealing member 84,86 into the hip joint of a human patient through a hole 18 in the pelvic bone 9 or a hole 82 in the femur bone 9.

FIG. 56b shows a section of the surgical instrument 83,85,88 comprising a tube like element for housing of the mould 81 and/or said first and second sealing members 84,86. A piston 89 used to transport said mould 81 and/or first and second sealing members 84,86 into the hip joint of a human patient is also shown.

FIG. 56c shows a the surgical instrument 83,85,88 adapted to insert a mould 81 and/or a first and second sealing member 84,86 into the hip joint of a human patient, the second embodiment further comprises a flexible or bent part 91 improving the reach of the surgical instrument.

After the steps of providing a mould 81 or a sealed space 87, fluid is injected into said mould 81 or into said sealed space 87 through the hole 18 in the pelvic bone 9 or the hole 82 in the femur bone 7.

FIG. 57 shows the hip joint in section wherein an injecting member 92 injects a fluid 93 into a sealed area 87 in the hip joint through a hole 18 in the pelvic bone 9 from the opposite side from acetabulum 8. Said sealed area 87, being sealed by a first 84 and second 86 sealing member. The injecting member 92 comprises a piston 94 that pushes said fluid 93 into the sealed area 87.

FIG. 58 shows the hip joint in section wherein an injecting member 92 injects a fluid 93 into a mould 81 in the hip joint through a hole 82 in the femur bone 7. The injecting member 92 comprises a piston 94 that pushes said fluid 93 into the mould 81.

Figure 59:
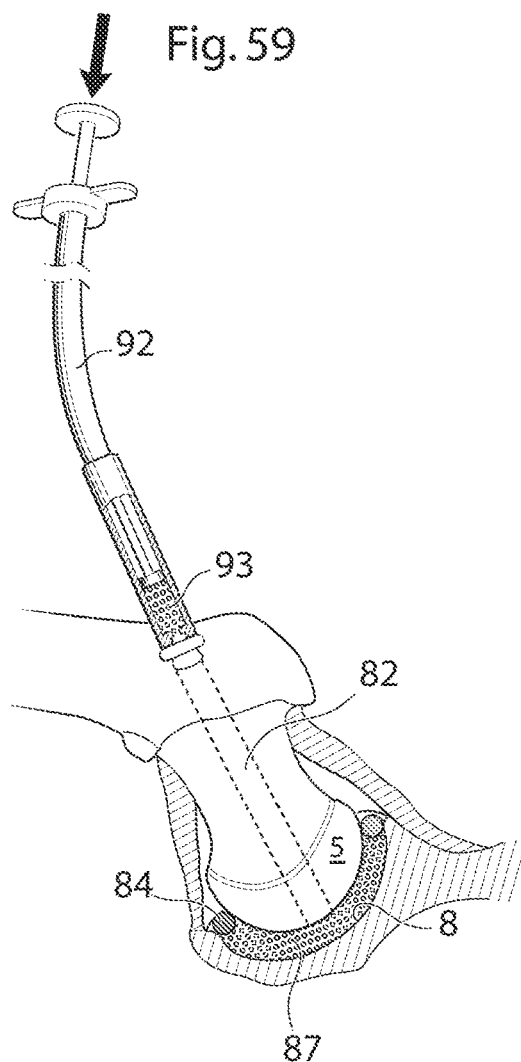
FIG. 59 shows the filling of a sealed area inside of the hip joint using an instrument that operates through the femur bone.

FIG. 59 shows the hip joint in section wherein an injecting member 92 injects a fluid 93 into a sealed area 87 in the hip joint through a hole 82 in the femur bone 7. Said sealed area 87, being sealed by at least a first 84 sealing member. The injecting member 92 comprises a piston 94 that pushes said fluid 93 into the sealed area 87.

Figure 60:
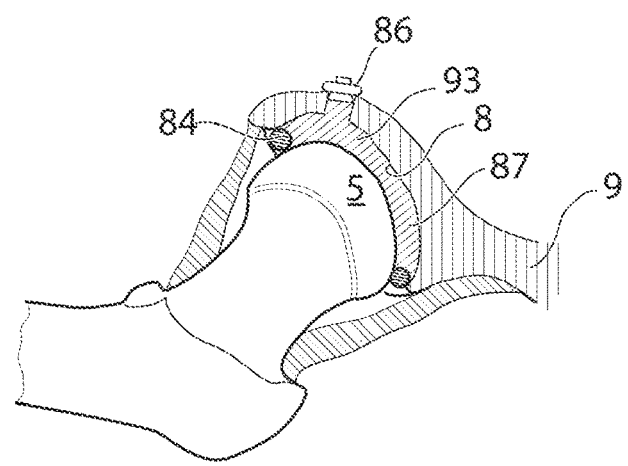
FIG. 60 shows a hip joint in section after a sealed area in the hip joint has been filled with a fluid.

FIG. 60 shows the sealed area 87, sealed by the first 84 and second 86 sealing member together with the caput femur 5 and the pelvic bone 9. A fluid adapted to harden 93 has been injected into said sealed area, and after the hardening of said fluid it provides at least one hip joint surface.

Figure 61:
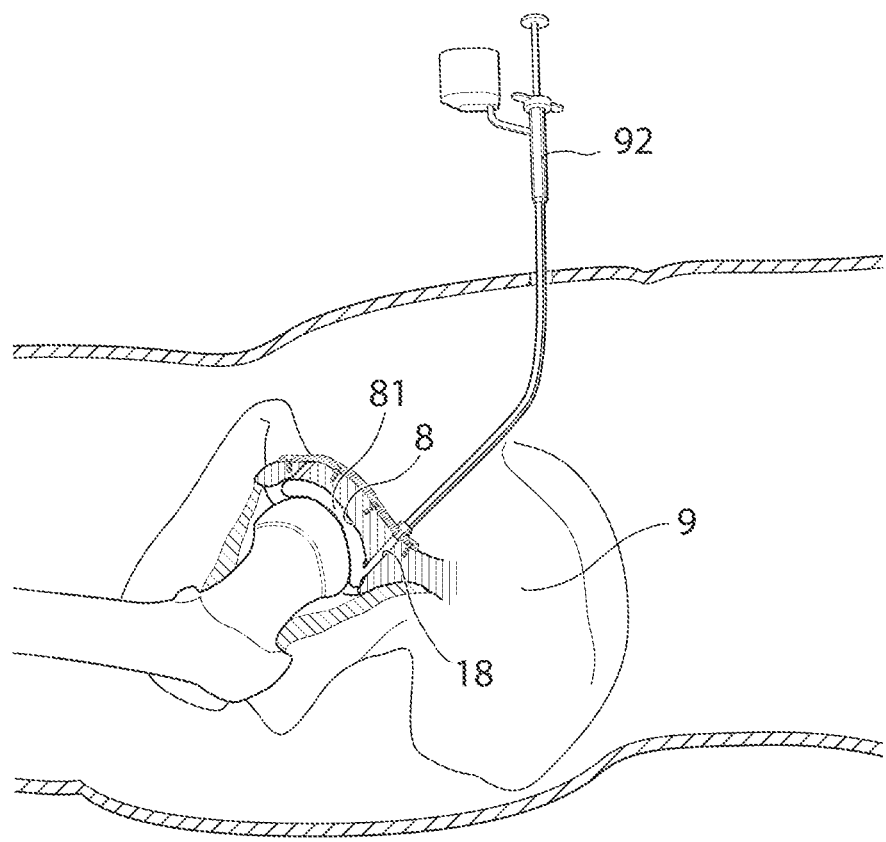
FIG. 61 shows the insertion of fluid into an area of a hip joint.

FIG. 61 shows a lateral section of the human body wherein an injecting member 92 injects a fluid into a mould 81 in the hip joint through a hole 18 in the pelvic bone 9 from the opposite side from acetabulum 8.

After the injecting member 92 has injected a fluid 93 into a mould 81 or a sealed are 87 it is being retracted from the area.

The mould 81 and the first and second sealing members 84,86 according to any of the embodiments can further be adapted to be resorbable by the human body or to melt after they have served their purpose.

After at least one hip joint surface has been provided through a hole 18 in the pelvic bone 9, in accordance with any of the embodiment above, said hole 18 needs to be closed.

Figure 62:
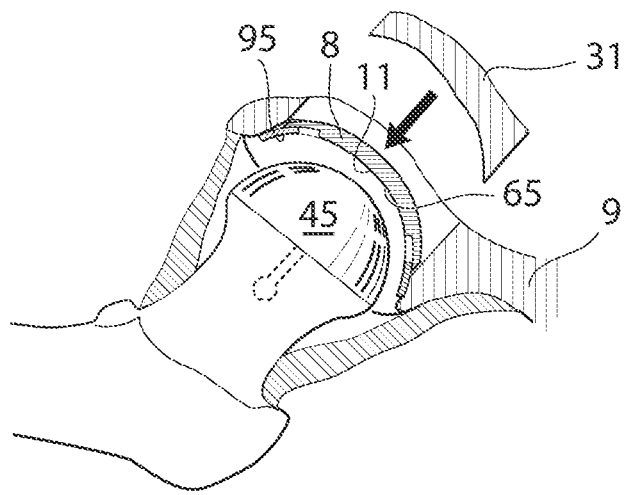
FIG. 62 shows the closing of a hole in the hip joint using a bone plug.

FIG. 62 shows the hip joint of a human patient in section wherein a bone plug 31 is placed in the hole 18 in the pelvic bone 9 to close said hole 18. According to a first embodiment the artificial acetabulum surface 65 comprises supporting members 94 which carries the load placed on the acetabulum 8 from weight of the human patient through the contact with the caput femur 5. Said supporting members can be adapted to be displaceable 97 supporting members. The bone plug 31 can be attached to the artificial acetabulum surface 11 and/or the pelvic bone 9 by means of bone cement, adhesive, screws, form fitting, welding, sprints, band or some other mechanical connecting member.

Figure 63:
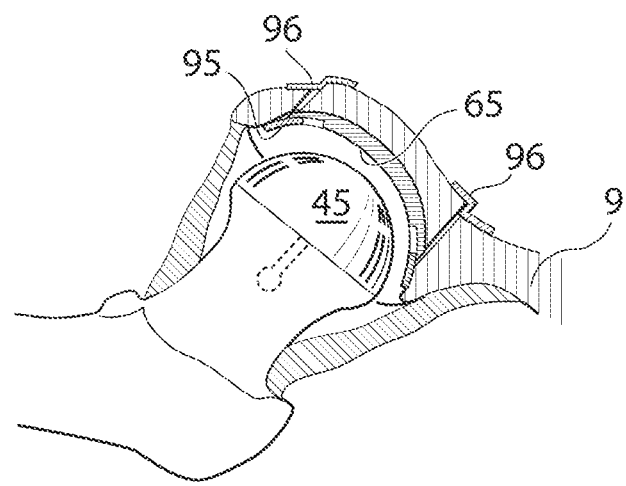
FIG. 63 shows the fixation of a bone plug in the pelvic bone.

FIG. 63 shows the hip joint of a human patient in section wherein the bone plug 31 placed in the hole 18 in the pelvic bone 9 is further supported by supporting means 96 placed between the bone plug 31 and the pelvic bone 9 on the opposite side from acetabulum 8 using at least one of: bone cement, adhesive, screws, form fitting, welding, sprints, band or some other mechanical connecting member.

Figure 64:
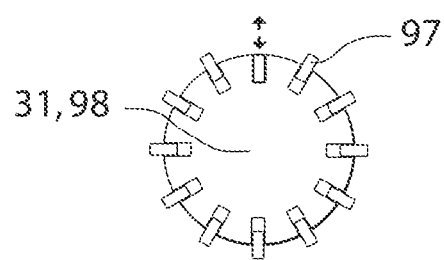
FIG. 64 shows a part for closing a hole in a pelvic bone having displaceable supporting members.

FIG. 64 shows a bone plug 31 or a prosthetic part 98 comprising several displaceable supporting members adapted to carry the load placed on the acetabulum 8 from weight of the human patient through the contact with the caput femur 5. The displaceable parts 97 are displaced into a corresponding part in or at the edge of the hole 18 in the pelvic bone 9.

Figure 65:
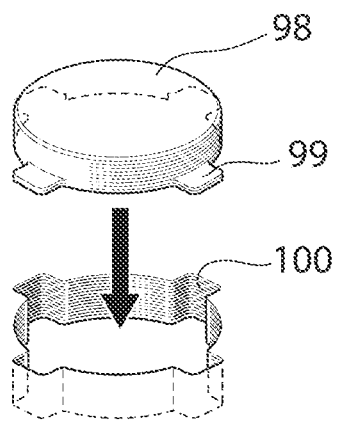
FIG. 65*a* shows a prosthetic part being used to close a hole in a pelvic bone.
FIG. 65*b* shows how sections of a prosthetic part is used as support against the edges of the hole in a pelvic bone.
FIG. 65*c* shows the insertion of a prosthetic part in a hole in a pelvic bone.
Figure 65:
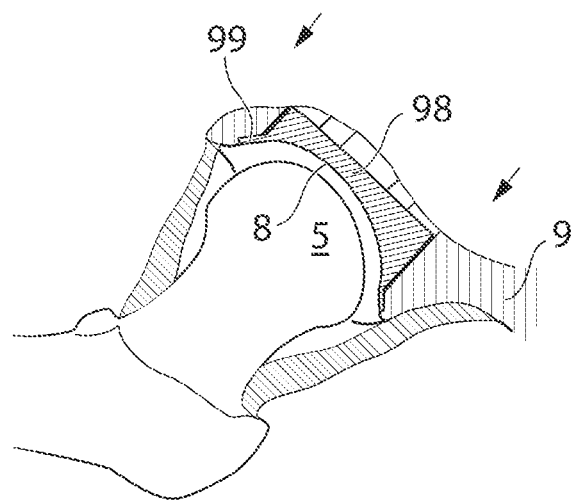
Figure 65:
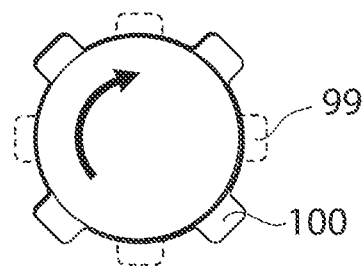

According to a second embodiment the closing of the hole 18 in the pelvic bone is done by means of a prosthetic part 98. FIG. 65a shows the prosthetic part 98 being inserted into a hole 18 in the pelvic bone 9 from the opposite side from acetabulum 8. According to one embodiment the prosthetic part 98 comprises supporting members 99 adapted to correspond with sections 100 of the hole 18 in the pelvic bone 9. After the prosthetic part 98 has been inserted into said hole 18 in the pelvic bone 9 it is rotated so that the supporting members 99 comes in contact with the pelvic bone 9 and can carry the load placed on the acetabulum 8 from weight of the human patient through the contact with the caput femur 5. Said prosthetic part 98 could also be adapted to serve as artificial acetabulum surface 65 according to any of the above mentioned embodiments.

FIG. 65b shows the prosthetic part 98 when rotated to carry the load placed on the acetabulum 8 from weight of the human patient through the contact with the caput femur 5.

FIG. 65c shows the hip joint of a human patient in section wherein the prosthetic part 98 closes the hole 18 in the pelvic bone 9 and carries the load placed on the acetabulum 8 from weight of the human patient through the contact with the caput femur 5 by means of the supporting members 99. The prosthetic part 98 can further be fixated to the pelvic bone 9 by means of bone cement, adhesive, screws, form fitting, welding, sprints, band or some other mechanical connecting member.

Figure 66:
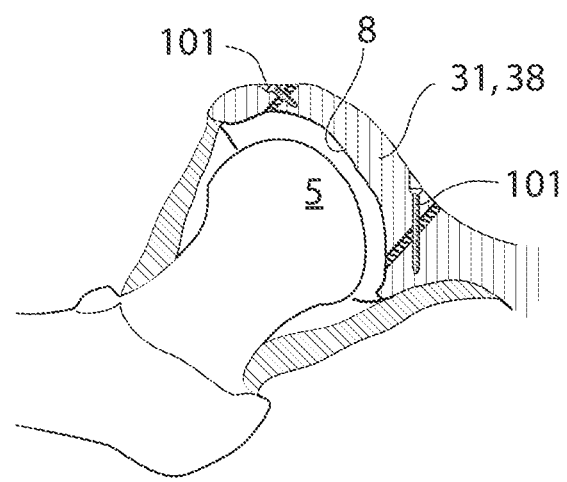
FIG. 66*a* shows how screws are being used to fixate a bone plug or a prosthetic part in a hole in a pelvic bone of a human patient.
FIG. 66*b* shows how a supporting plate is being used to fixate a bone plug or a prosthetic part in a hole in a pelvic bone of a human patient.
FIG. 66*c* shows two bone plugs or prosthetic parts being fixated using a supporting plate.
FIG. 66*d* shows a section of the hip joint after two holes in the pelvic bone have been filled with a fluid.
Figure 66:
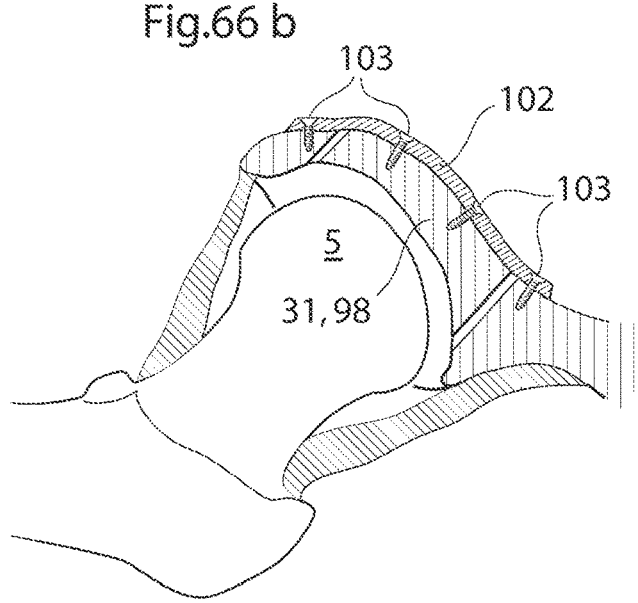
Figure 66:
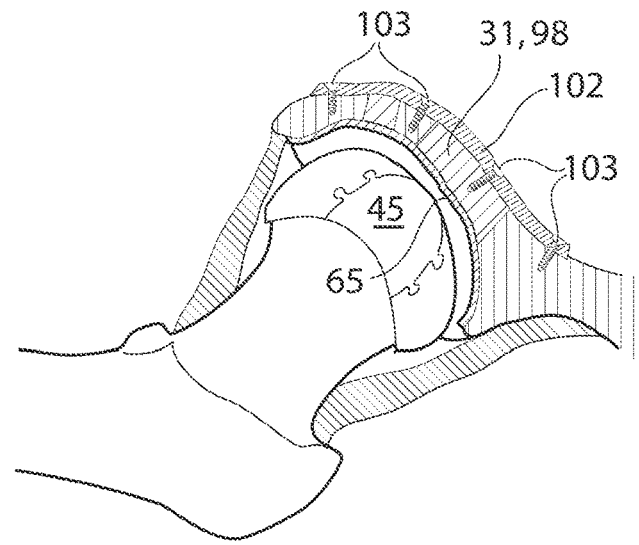
Figure 66:
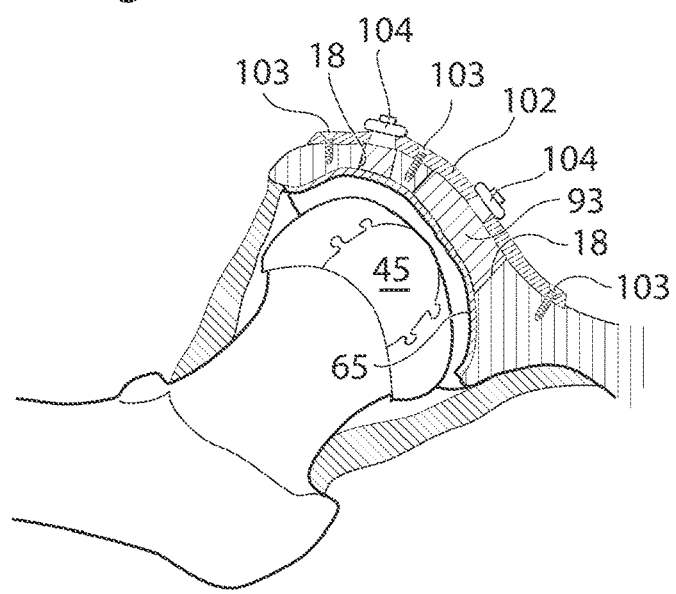

FIG. 66a shows the hip joint of a human patient in section wherein bone plug 31 or prosthetic part 98 is attached to the pelvic bone 9 by means of screws 101 placed from the opposite side from acetabulum 8. The screws 101 are possible to place in different angles depending on reach or need for support.

FIG. 66b shows the hip joint of a human patient in section wherein bone plug 31 or prosthetic part 98 is attached to the pelvic bone 9 by means of a plate 102 at least partly covering said bone plug 31 or prosthetic part 98. According to a first embodiment the plate 102 is attached to the pelvic bone 9 by means of screws 103 placed from the opposite side from acetabulum 8. However it is also conceivable that said screws 103 can be replaced or assisted by bone cement, adhesive, form fitting, welding, sprints, band or some other mechanical connecting member.

FIG. 66c shows the hip joint of a human patient in section wherein two bone plugs 31 or prosthetic parts 98 are attached to the pelvic bone 9 by means of a plate 102 at least partly covering said bone plugs 31 or prosthetic parts 98. According to a first embodiment the plate 102 is attached to the pelvic bone 9 by means of screws 103 placed from the opposite side from acetabulum 8. However it is also conceivable that said screws 103 can be replaced or assisted by bone cement, adhesive, form fitting, welding, sprints, band or some other mechanical connecting member. FIG. 66c also shows the provided artificial acetabulum surface 65.

FIG. 66d shows the hip joint of a human patient in section wherein two holes 18 in the pelvic bone has been covered by means of a fluid injected into said holes 18, through sealing members 104, said fluid 93 being adapted to harden. Furthermore a plate 102 has been provided at least partly covering said holes 18. According to a first embodiment the plate 102 is attached to the pelvic bone 9 by means of screws 103 placed from the opposite side from acetabulum 8. However it is also conceivable that said screws 103 can be replaced or assisted by bone cement, adhesive, form fitting, welding, sprints, band or some other mechanical connecting member. FIG. 66d also shows the provided artificial acetabulum surface 65, and the provided artificial caput femur surface 45.

Figure 67:
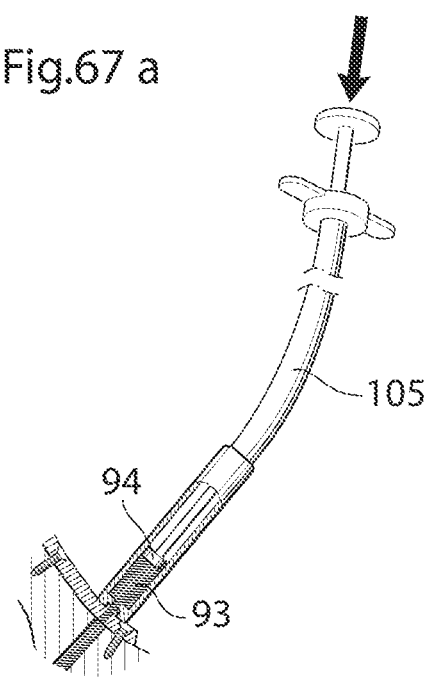
FIG. 67*a* shows an injecting member adapted to inject a fluid into an area of a hip joint.
FIG. 67*b* shows an injecting member adapted to inject a fluid into an area of a hip joint when injecting a fluid.
Figure 67:
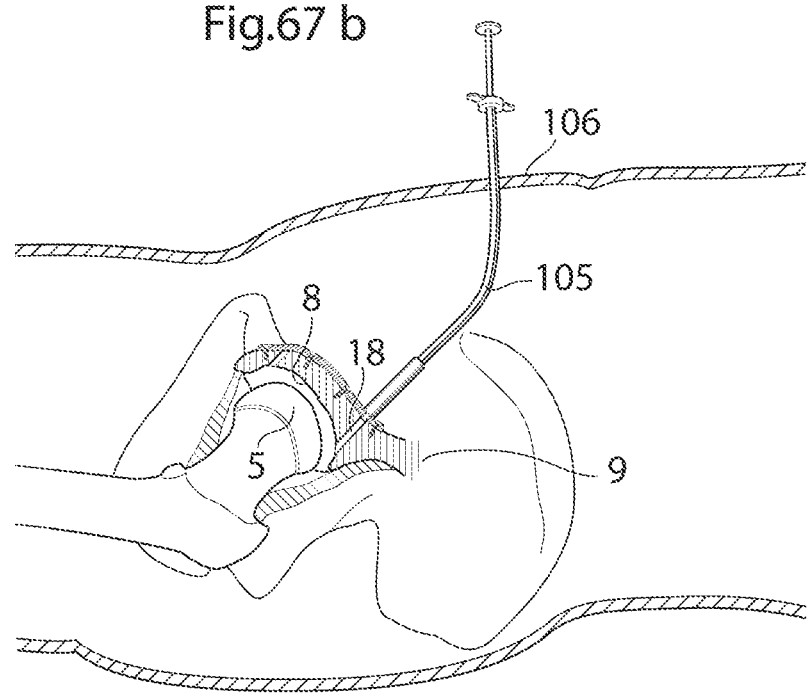

FIG. 67a shows an injecting member 105 for injecting a fluid adapted to harden 93, preferably bone cement or adhesive to be used as support in the closing of the hole 18 in the pelvic bone 9. The injecting member 105 comprises a piston 94 that pushes said fluid 93 the area where it is wanted.

FIG. 67b shows the injecting member 105 as it is inserted through the skin 106 of a human patient in the surgical or laparoscopic/arthroscopic method, and is further placed in connection with the hip joint through the hole 18 in the pelvic bone 9. The injecting member 105 is adapted to inject a fluid 93 adapted to harden.

Figure 68:
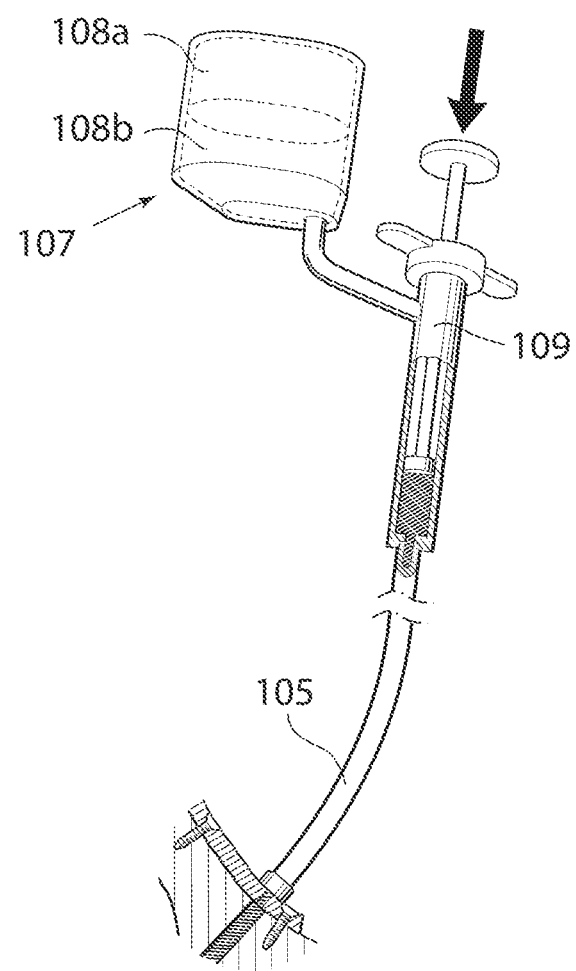
FIG. 68 shows an injecting member in further detail.

FIG. 68 shows the injecting member 105 according to any of the embodiments above, adapted to inject fluid 93 into a mould 81, a sealed area 87 or a connecting area between the pelvic bone 9 and a prosthetic part, the pelvic bone 9 and a bone plug 31 or the caput femur 5 and a prosthetic part. Said injecting member comprises a container 107 adapted to hold a fluid for injection. According to a first embodiment said container comprises two compartments 108a,b adapted to hold two different fluids, said fluids being adapted to harden when mixed. In the embodiment when the container 107 is adapted to hold two fluids, it is conceivable that the injecting member 105 further comprises a mixing member 109 wherein said two fluids are being mixed before injection. According to a second embodiment (not shown) said container 107 is adapted to keep said fluid sterile. According to a third embodiment (not shown) said container 107 is adapted to keep said fluid cold and according to a fourth embodiment (not shown) said container 107 is adapted to keep said fluid in a dark environment. Furthermore a combination of the above mentioned embodiments is conceivable.

After the step of closing the hole in the pelvic bone of the human patient is concluded all instruments are retracted and the final step of the surgical or laparoscopic/arthroscopic method is performed. The final step comprises suturing or stapling the affected tissue and finally suturing or stapling the skin of the human patient.

Figure 69:
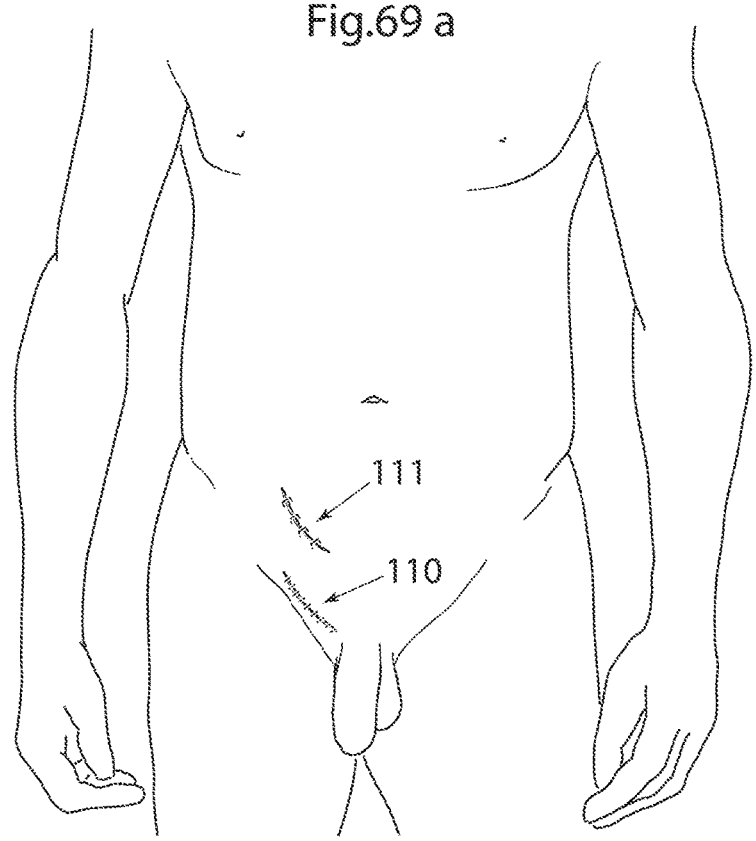
FIG. 69*a* shows the step of suturing or stapling in the surgical method.
FIG. 69*b* shows the step of suturing or stapling in the laparoscopic/arthroscopic method.
Figure 69:
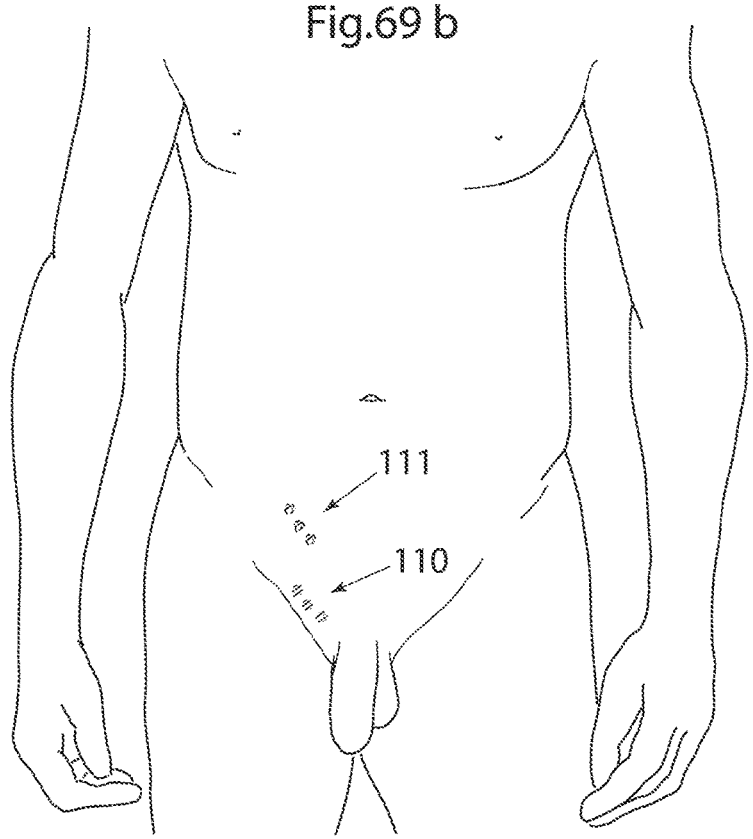

FIG. 69a shows the step of suturing 110 or stapling 111 the skin 106 of the human patient in the surgical method, whereas FIG. 69b shows the step of suturing 110 or stapling 111 the skin 106 of the human patient in the laparoscopic/arthroscopic method.

Please note that any embodiment or part of embodiment as well as any method or part of method could be combined in any way. All examples herein should be seen as part of the general description and therefore possible to combine in any way in general terms.

The invention claimed is:

1. A method of treating a hip joint of a human patient using a pelvic drill comprising a driving member, a bone contacting member and an operating device for operating said driving member, the hip joint comprising a caput femur and an acetabulum, said method comprising the steps of:
   cutting the skin of the human patient,
   dissecting an area of a pelvic bone on an opposite side from the acetabulum,
   creating a hole in said dissected area using said pelvic drill, said hole passing through the pelvic bone and into the hip joint of the human patient, and
   providing at least one hip joint surface to the hip joint, through said hole in the pelvic bone of the human patient.

2. A method of treating a hip joint of a human patient using a pelvic drill comprising a driving member, a bone contacting member and an operating device for operating said driving member, the hip joint comprising a caput femur and an acetabulum, said method comprising the steps of:
   inserting a needle or tube like instrument into the patient's body,
   using the needle or tube like instrument to fill a part of the patient's body with gas and thereby expanding a cavity within the patient's body,
   placing at least two laparoscopic/arthroscopic trocars in said cavity,
   inserting a camera through one of the laparoscopic/arthroscopic trocars into said cavity,
   inserting at least one dissecting tool through one of said at least two laparoscopic/arthroscopic trocars,
   dissecting an area of the pelvic bone on the opposite side from the acetabulum,
   creating a hole in said dissected area using said pelvic drill, said hole passing through the pelvic bone and into the hip joint of the human patient, and
   providing at least one hip joint surface to the hip joint, through said hole in the pelvic bone of the human patient.

3. The method of treating a hip joint of a human patient according to any one of claims 1 and 2, further comprising the step of reaming the acetabulum or the caput femur.

4. The method of treating a hip joint of a human patient according to any one of claims 1 and 2, further comprising the step of fixating the hip joint surface to the caput femur or to the pelvic bone by means of mechanical fixating members, bone cement or adhesive.

5. The method of treating a hip joint of a human patient according to any one of claims 1 and 2, further comprising the step of closing said hole in the pelvic bone by means of any one of: bone cement, a bone plug, and a prosthetic part.

6. The method of treating a hip joint of a human patient according to any one of claims 1 and 2, further comprising the step of placing a mould inside of the hip joint of the human patient and subsequently injecting a fluid into said mould placed inside of the hip joint of the human patient.

7. The method of treating a hip joint of a human patient according to any one of claims 1 and 2, further comprising the steps of:
   a. placing at least one sealing member between the acetabulum and the caput femur, thus creating a sealed area between the acetabulum and the caput femur, and
   b. injecting a fluid into said sealed area.

8. The method of treating a hip joint of a human patient according to any one of claims 1 and 2, wherein the step of dissecting the area of the pelvic bone comprises dissecting least one of the areas selected from the group consisting of:
   a. an area between the peritoneum and the pelvic bone,
   b. an area between the pelvic bone and the surrounding tissue,
   c. an area of the inguinal region, and
   d. an area of the abdominal cavity.

9. The method of treating a hip joint of a human patient according to claim 2, wherein said cavity is located in one of the areas selected from the group consisting of:
   a. the abdominal region,
   b. the inguinal region, and
   c. the pelvic region.

10. The method of treating a hip joint of a human patient according to claim 1, wherein the step of cutting the skin of the human patient is performed in one of the areas selected from the group consisting of:
   a. the abdominal wall,
   b. the inguinal area, and
   c. the pelvic region.

11. The method according to claim 1, wherein said driving member and said bone contacting member together form an elongated member, the method further comprising placing said elongated member in the hip joint such that the elongated member is supported at a first supporting point in a femoral bone for the bone contacting member and a second supporting point in the pelvic bone.

12. The method according to claim 11, further comprising connecting the operating device to said driving member and using the operating device to apply force to the elongated member from outside the patient's body, on the opposite side of said hip joint outside the pelvic bone.

13. The method according to claim 11, wherein said elongated member receives a force from the operating device in the abdomen or outside the patient's body, lateral to a proximal portion of the femoral bone.

* * * * *